(12) United States Patent
Harley et al.

(10) Patent No.: US 10,316,366 B2
(45) Date of Patent: Jun. 11, 2019

(54) MEASURES OF SHORT TELOMERE ABUNDANCE

(71) Applicant: TELOMERE DIAGNOSTICS, INC., Menlo Park, CA (US)

(72) Inventors: Calvin Harley, Murphys, CA (US); Jue Lin, Foster City, CA (US); Yajing Hu, San Jose, CA (US)

(73) Assignee: TELOMERE DIAGNOSTICS, INC., Menlo Park, CA (US)

( * ) Notice: Subject to any disclaimer, the term of this patent is extended or adjusted under 35 U.S.C. 154(b) by 531 days.

(21) Appl. No.: 14/892,395

(22) PCT Filed: May 22, 2014

(86) PCT No.: PCT/US2014/039110
§ 371 (c)(1),
(2) Date: Nov. 19, 2015

(87) PCT Pub. No.: WO2014/190138
PCT Pub. Date: Nov. 27, 2014

(65) Prior Publication Data
US 2016/0090630 A1     Mar. 31, 2016

Related U.S. Application Data

(60) Provisional application No. 61/826,484, filed on May 22, 2013.

(51) Int. Cl.
*C12Q 1/68* (2018.01)
*C12Q 1/6883* (2018.01)
*C12Q 1/686* (2018.01)

(52) U.S. Cl.
CPC ........... *C12Q 1/6883* (2013.01); *C12Q 1/686* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| | | |
|---|---|---|
| 4,280,992 A | 7/1981 | Sugiura et al. |
| 4,469,863 A | 9/1984 | Ts'o et al. |
| 4,683,195 A | 7/1987 | Mullis et al. |
| 4,683,202 A | 7/1987 | Mullis |
| 5,034,506 A | 7/1991 | Summerton et al. |
| 5,216,141 A | 6/1993 | Benner |
| 5,235,033 A | 8/1993 | Summerton et al. |
| 5,386,023 A | 1/1995 | Sanghvi et al. |
| 5,489,508 A | 2/1996 | West et al. |
| 5,602,240 A | 2/1997 | De Mesmaeker et al. |
| 5,637,684 A | 6/1997 | Cook et al. |
| 5,644,048 A | 7/1997 | Yau |
| 5,686,245 A | 11/1997 | West et al. |
| 5,741,677 A | 4/1998 | Kozlowski et al. |
| 5,741,678 A | 4/1998 | Ronai |
| 5,834,193 A | 11/1998 | Kozlowski et al. |
| 5,856,096 A | 1/1999 | Windle et al. |
| 5,910,122 A | 6/1999 | D'Angelo |
| 5,928,916 A | 7/1999 | Keogh |
| 5,945,319 A | 8/1999 | Keogh |
| 6,020,124 A | 2/2000 | Sorenson |
| 6,022,326 A | 2/2000 | Tatum et al. |
| 6,436,677 B1 | 8/2002 | Gu et al. |
| 6,444,261 B1 | 9/2002 | Plaksine et al. |
| 6,514,693 B1 | 2/2003 | Lansdorp |
| 6,919,200 B2 | 7/2005 | Ibrahim |
| 7,482,116 B2 | 1/2009 | Birnboim |
| 7,557,190 B2 | 7/2009 | Barbosa et al. |
| 7,601,521 B2 | 10/2009 | Sidransky |
| 7,695,904 B2 | 4/2010 | Cawthon |
| 8,025,849 B2 | 9/2011 | Baldwin et al. |
| 8,039,215 B2 | 10/2011 | Higuchi et al. |
| 8,048,631 B2 | 11/2011 | Cawthon |
| 8,221,381 B2 | 7/2012 | Muir et al. |

(Continued)

FOREIGN PATENT DOCUMENTS

| | | |
|---|---|---|
| AU | 2003208902 B2 | 8/2008 |
| AU | 2009329987 A1 | 7/2011 |
| AU | 2012362210 A1 | 8/2014 |
| CA | 2474468 A1 | 8/2003 |
| CA | 2513747 A1 | 8/2004 |
| CA | 2748265 A1 | 7/2010 |
| CN | 1639352 A | 7/2005 |
| CN | 201188066 Y | 1/2009 |
| CN | 102439171 A | 5/2012 |
| CN | 104105798 A | 10/2014 |

(Continued)

OTHER PUBLICATIONS

Heacock et al. (EMBO Journal, 2004, vol. 23, p. 2304-2313) (Year: 2004).*
Cawton et al. (Nuleic Acids Research, 2002, vol. 30, No. 10, e47, p. 1-6, IDS reference) (Year: 2002).*
Fitzpatrick et al. (Am J Epidemiol, 2007, 165(1):14-21) (Year: 2007).*
Bendix et al. (Journal of Gerontology: Medical Sciences, 2013, 69(2):231-239, IDS reference) (Year: 2013).*

(Continued)

*Primary Examiner* — Stephanie K Mummert
(74) *Attorney, Agent, or Firm* — Ballard Spahr LLP

(57) ABSTRACT

This invention provides methods and materials for measuring telomere abundance from chromosomes in a sample having telomeres within a pre-determined length range, e.g., short telomeres up to a certain length. The methods can involve a first step of performing a time-limited extension reaction calibrated to produce extension products from a double-stranded chromosomal DNA template of no more than a defined length, and a second step of amplifying, from the extension products, sequences bounded by a sub-telomeric sequence and the anchor sequence, to produce a length-limited telomere sequence product. The abundance of telomeric sequences in this product can be measured, and the measures can be correlated to a variety of indices.

29 Claims, 8 Drawing Sheets

Specification includes a Sequence Listing.

(56) References Cited

U.S. PATENT DOCUMENTS

| | | | |
|---|---|---|---|
| 8,318,911 | B2 | 11/2012 | Anastasi et al. |
| 9,169,516 | B2 | 10/2015 | Cawthon |
| 2003/0162209 | A1 | 8/2003 | Martin |
| 2003/0162266 | A1 | 8/2003 | Cawthon |
| 2004/0175733 | A1 | 9/2004 | Andersen et al. |
| 2004/0265815 | A1 | 12/2004 | Baird |
| 2005/0009097 | A1 | 1/2005 | Better et al. |
| 2006/0141492 | A1 | 6/2006 | Sowers et al. |
| 2006/0210980 | A1 | 9/2006 | Cawthon |
| 2007/0161031 | A1 | 7/2007 | Trinklein et al. |
| 2007/0274982 | A1 | 11/2007 | Peters et al. |
| 2008/0063628 | A1 | 3/2008 | Davis et al. |
| 2009/0142408 | A1 | 6/2009 | Lin et al. |
| 2010/0010064 | A1 | 1/2010 | Moore et al. |
| 2010/0151477 | A1 | 6/2010 | Cawthon |
| 2010/0273675 | A1 | 10/2010 | Balis et al. |
| 2010/0311954 | A1 | 12/2010 | Chamberlain et al. |
| 2011/0182862 | A1 | 7/2011 | Green et al. |
| 2011/0207128 | A1 | 8/2011 | Cawthon et al. |
| 2011/0212002 | A1 | 9/2011 | Curry et al. |
| 2011/0244462 | A1 | 10/2011 | Bendix et al. |
| 2011/0294676 | A1 | 12/2011 | Cawthon |
| 2011/0296543 | A1 | 12/2011 | Chang et al. |
| 2012/0252014 | A1 | 10/2012 | Loeffert et al. |
| 2013/0011918 | A1 | 1/2013 | West et al. |
| 2014/0248622 | A1 | 9/2014 | Wang et al. |
| 2014/0370505 | A1 | 12/2014 | Harley |
| 2016/0186250 | A1 | 6/2016 | Harley et al. |
| 2016/0194705 | A1 | 7/2016 | Cawthon |
| 2017/0023451 | A1 | 1/2017 | Harley |

FOREIGN PATENT DOCUMENTS

| | | |
|---|---|---|
| EP | 0155747 A1 | 9/1985 |
| EP | 1476561 A2 | 11/2004 |
| EP | 1585974 A2 | 10/2005 |
| EP | 2325619 A1 | 5/2011 |
| EP | 2379747 | 10/2011 |
| EP | 2474822 A1 | 7/2012 |
| EP | 2798091 A1 | 11/2014 |
| HK | 1020259 | 4/2000 |
| HK | 1072275 A1 | 6/2012 |
| HK | 1169681 | 2/2013 |
| HK | 1169683 | 2/2013 |
| HK | 1173218 | 5/2013 |
| JP | H09-206081 | 5/1996 |
| JP | 2004-533801 A | 11/2004 |
| JP | 2005-027518 A | 2/2005 |
| JP | 2005515778 | 6/2005 |
| JP | 4515767 B2 | 8/2010 |
| JP | 2012-513215 A | 6/2012 |
| JP | 5686493 B2 | 3/2015 |
| TW | 201343919 A | 11/2013 |
| WO | WO-1996/041016 A1 | 12/1996 |
| WO | WO-97/12681 A1 | 4/1997 |
| WO | WO-99/46408 A1 | 9/1999 |
| WO | WO-00/30753 A1 | 6/2000 |
| WO | WO-01/40462 A1 | 6/2001 |
| WO | WO-01/66799 A2 | 9/2001 |
| WO | WO-2003/064615 | 8/2003 |
| WO | WO-2004/068110 A2 | 8/2004 |
| WO | WO-2006/110735 A2 | 10/2006 |
| WO | WO-2010/075413 A1 | 7/2010 |
| WO | WO-2013/102116 A1 | 7/2013 |
| WO | WO-2014/152676 | 9/2014 |
| WO | WO-2014/190138 A2 | 11/2014 |

OTHER PUBLICATIONS

Notice of Reasons for Rejection dated Oct. 12, 2017 by the Japanese Patent Office for Patent Application No. 2015-175362, which was filed on Sep. 7, 2015 and published as JP 2015-221053 on Dec. 10, 2015 (Inventor—Cawthon et al.; Applicant—University of Utah Research Foundation) (Original—3 pages // Translation—3 pages).

Non-Final Office Action dated Nov. 2, 2017 by the U.S. Patent and Trademark Office for U.S. Appl. No. 14/858,177, filed Sep. 18, 2015 and published as US 2016/0194705 on Jul. 7, 2016 (Inventor—Richard Cawthon; Applicant—University of Utah research Foundation) (9 pages).

Notice of Allowance dated Dec. 6, 2017 by the U.S. Patent and Trademark Office for U.S. Appl. No. 14/746,437, filed Jun. 22, 2015 and published as US 2016/0186250 on Jun. 30, 2016 (Inventor—Harley et al.; Applicant—Telomere Diagnostics, Inc.) (10 pages).

International Search Report and Written Opinion dated Oct. 28, 2015 by the International Searching Authority for International Patent Application No. PCT/US2015/036991, which was filed on Jun. 22, 2015 (Inventor—Harley et al.; Applicant—Telome Health, Inc.) (12 pages).

Brouilette, S.W. et al., Telomere Length, Risk of Coronary Heart Disease, and Stain Treatment in the West of Scotland Primary Prevention Study: A Nested Case-Control Study, Lancet, 369: 107-14 (2007).

Willeit, P. et al., Cellular Aging Reflected by Leukocyte Telomere Length Predicts Advanced Atherosclerosis and Cardiovascular Disease Risk, Arterioscler Thromb Vasc Biol, 30: 1649-56 (2010).

Canela, A. et al., High-Throughput Telomere Length Quantification by FISH and Its Application to Human Population Studies, Proc Natl Acad Sci USA, 104(13): 5300-5 (2007).

Heacock et al., Molecular Analysis of Telomere Fusions in *Arabidopsis*: Multiple Pathways for Chromosome End-Joining, EMBO J, 23(11): 2304-13 (2004).

Lin, K.W. et al: "The telomere length dynamic and methods of its assessment", Journal of Cellular and Molecular Medicine, (2005) 9(4): 977-989.

Sfeir, A.J., et al: "Telomere-End Processing: the Terminal Nucleotides of Human Chromosomes", Molecular Cell, (2005) 18(1):131-138.

Supplementary European Search Report and Written Opinion dated Dec. 2, 2016 by the European Patent Office for EP Application No. 14800611.7, which was filed on May 22, 2014 and published as 2999800 on Mar. 30, 2016 (Applicant—Telomere Diagnostics, Inc.; Inventor-Calvin Harvey et al.) (10 pages).

Adaikalakoteswari, A. et al., Association of Telomere Shortening with Impaired Glucose Tolerance and Diabetic Macroangiopathy. Atherosclerosis. 195: 83-9 (2007).

Alder, J.K. et al., Short Telomeres are a Risk Factor for Idiopathic Pulmonary Fibrosis. Proc Natl Acad Sci USA. 105(35): 13051-6 (2008).

Allshire, R.C. et al., Human Telomeres Contain at Least Three Types of G-Rich Repeat Distributed Non-Randomly. Nucleic Acids Res. 17(12): 4611-27 (1989).

Allsopp, R.C. et al., Telomere Length Predicts Replicative Capacity of Human Fibroblasts. Proc Natl Acad Sci USA. 89(21): 10114-8 (1992).

Almasy L, et al. (1998) Multipoint quantitative-trait linkage analysis in general pedigrees. Am J Hum Genet. 62: 1198-211.

Aps, J.K.M. et al., Flow Cytometry as a New Method to Quantify the Cellular Content of Human Saliva and Its Relation to Gingivitis. Clinica Chimica Acta. 321(1-2): 35-41 (2002).

Asai, A. et al., A Novel Telomerase Template Antagonist (GRN163) as a Potential Anticancer Agent. Cancer Res. 63: 3931-9 (2003).

Austriaco, Jr. et al., Changes of Telomere Length Cause Reciprocal Changes in the Lifespan of Mother Cells in *Saccharomyces cerevisiae*. Proc Natl Acad Sci USA. 94: 9768-72 (1997).

Baerlocher, G. and P. Lansdorp, Telomere Length Measurements in Leukocyte Subsets by Automated Multicolor Flow FISH. Cytometry. 55: 1-6 (2003).

Baerlocher, G. et al., Flow Cytometry and FISH to Measure the Average Length of Telomeres (flow FISH). Nature Protocols. 1(5): 2365-76 (2006).

Baerlocher, G. et al., Telomere Length Measurement by Fluorescence in Situ Hybridization and Flow Cytometry: Tips and Pitfalls. Cytometry. 47: 89-99 (2002).

Baird, D.M. et al., Extensive Allelic Variation and Ultrashort Telomeres in Senescent Human Cells. Nat Genet. 33(2): 203-7 (2003).

(56) References Cited

OTHER PUBLICATIONS

Baird, D.M. et al., Mechanisms Underlying Telomere Repeat Turnover, revealed by Hypervariable Variant Repeat Distribution Patterns in the Human Xp/Yp Telomere. EMBO J. 14(21): 5433-43 (1995).
Bakaysa, S.L. et al. (2007) Telomere length predicts survival independent of genetic influences. Aging Cell. 6(6): 769-74.
Baldino, F.J. et al., High-Resolution in situ Hybridization Histochemistry. Methods Enzymology. 168: 761-77 (1989).
Beaucage, S.L. and P.I. Radhakrishnan, The Functionalization of Oligonucleotides Via Phosphoramidite Derivatives. Tetrahedron. 49(10): 1925-63 (1993).
Bechter, O.E. et al., Telomere Length and Telomere Activity Predict Survival in Patients with B Cell Chronic Lymphocytic Leukemia. Cancer Res. 58(21): 4918-22 (1998).
Beekman, M. et al., (2006) Chromosome 4q25, microsomal transfer protein gene, and human longevity: novel data and a meta-analysis of association studies. J Gerontol A Biol Sci Med Sci. 61(4): 355-62.
Bendix et al., Longitudinal Changes in Leukocyte Telomere Length and Mortality in Humans. J Gemotol A Biol Sci Med Sci. 69(2): 231-9 (2014).
Bessler, M. et al., Dysfunctional Telomeres and Dsykeratosis Congenita. Haematologica. 92(8): 1009-12 (2007).
Blasco, M.A. et al. (1997) Telomere shortening and tumor formation by mouse cells lacking telomerase RNA. Cell. 91(1): 25-34.
Boulay, J.L. et al. (1999) Gene dosage by quantitative real-time PCR. Biotechniques. 27(2): 228-30, 232.
Bray, P. et al., Human cDNA Clones for Four Species of Ga Signal Tranduction Protein. Proc Natl Acad Sci USA. 83(23): 8893-7 (1986).
Brill, W.K.D. et al., Synthesis of Oligodeoxynucleoside Phosphorodithioates via Thioamidites. J Am Chem Soc. 111(6): 2321-2 (1989).
Brouilette, S.W. et al., White Cell Telomere Length and Risk of Premature Myocardial Infarction. Arterioscler Throm Vasc Biol. 23: 842-6 (2003).
Brown, M.D. et al. (2006) IQGAP1 in cellular signaling: bridging the GAP. Trends Cell Biol. 16(5): 242-9.
Brummendorf et al., Telomere Length in Leukocyte Subpopulations of Patients with Aplastic Anemia. Blood. 97(4): 895-900 (2001).
Calado, R.T. and N.S. Young, Telomeres, telomerase, and Human Disease. The Hematologist. 7(1): 7 (2010).
Capezzone, M. et al., Short Telomeres, Telomerase Reverse Transcriptase Gene Amplification, and Increased Telomerase Activity in the Blood of Familial Papillary Thyroid Cancer Patients. J Clin Endocrinol Metab. 93(10): 3950-7 (2008).
Cariello, N.F. et al., Fidelity of Thermococcus litoralis DNA Polymerase (Vent) in PCR Determined by Denaturing Gradient Gel Electrophoresis. Nucleic Acids Res. 19(15): 4193-8 (1991).
Carlsson, C. et al., Screening for Genetic Mutations. Nature. 380(6571): 207 (1996).
Cawthon, R.M. et al., Association between telomere length in blood and mortality in people aged 60 years or older. Lancet. 361: 393-5 (2003).
Cawthon, R.M., Telomere measurement by quantitative PCR. Nucleic Acids Res. 30(10): e47 (2002).
Cawthon, R.M., Telomere length measurement by a novel monochrome multiplex quantitative PCR method. Nucleic Acids Res. 37(3): e21 (2009).
Challacombe, S.J. and J.R. Naglik, The Effects of HIV Infection on Oral Mucosal Immunity. Adv Dental Res. 19: 29-35 (2006).
Chang et al., Telomere Length and Replicative Aging in Human Vascular Tissues, Proc Natl Acad Sci USA, 92: 11190-4 (1995).
Cherif et al., Ageing and Telomeres: A Study into Organ and Gender-Specific Telomere Shortening. Nucleic Acids Res. 31(5): 1576-83 (2003).
Cheung, V.G. et al., The genetics of variation in gene expression. Nat Genet. 32 Suppl: 522-5 (2002).
Cheung, V.G. et al., Natural variation in human gene expression assessed in lymphoblastoid cells. Nat Genet. 33: 422-5 (2003).
Cheung, V.G. et al., Mapping determinants of human gene expression by regional and genome-wide association. Nature. 437(7063): 1365-9 (2005).
Chien, A. et al., Deoxyribonucleic Acid Polymerase from the Extreme Thermophile Thermus aquaticus. J Bacteriol. 127(3): 1550-7 (1976).
Christensen, K. et al., The Quest for Genetic Determinants of Human Longevity: Challenges and Insights. Nature Reviews Genetics. 7: 436-48 (2006).
Cohen, S. et al., A Global Measure of Perceived Stress. J Health Soc Behav. 24(4): 385-96 (1983).
Cronkhite, J.T. et al., Telomere Shortening in Familial and Spradic Pulmonary Fibrosis. Am J Resp Crit Care Med. 178: 729-37 (2008).
D'Aquila, R.T. et al., Maximizing sensitivity and specificity of PCR by pre-amplification heating. Nucleic Acid Research. 19(13): 3749 (1991).
Dai, M. et al., Evolving gene/transcript definitions significantly alter the interpretation of GeneChip data. Nucleic Acids Res. 33(20): e175 (2005).
Dausset, J. et al., Centre d'etude du polymorphisme humain (CEPH): collaborative genetic mapping of the human genome. Genomics. 6(3): 575-577 (1990).
De Mesmaeker, A. et al., Comparison of Rigid and Flexible Backbones in Antisense Oligonucleotides. Bioorg Med Chem Lett. 4(3): 395-8 (1994).
Dempcy, R.O. et al., Synthesis of a Thymidyl Pentamer of Deoxyribonucleic Guanidine and Bunding Studies with DNA Homopolynucleotides. Proc Natl Acad Sci USA. 92(13): 6097-101 (1995).
Diaz, R.S. and E.C. Sabino, Accuracy of Replication in the Polymerase Chain Reaction. Comparison Between Thermotoga maritima DNA Polymerase and Thermus aquaticus DNA Polymerase. Braz J Med Res. 31(10): 1239-42 (1998).
Dixon, A.L. et al., A genome-wide association study of global gene expression. Nat Genet. 39(10): 1202-7 (2007).
Don, R.H. et al., 'Touchdown' PCR to circumvent spurious priming during gene amplification. Nucleic Acid Research. 19(14): 4008 (1991).
Dustin, M.L. (2006) Immunology. When F-actin becomes too much of a good thing. Science. 313(5788): 767-8.
Effros, R.B. et al., Shortened Telomeres in the Expanded CD28-CD8+ Cell Subset in HIV Disease Implicate Replicative Senescence in HIV Pathogenesis, AIDS, 10(8): F17-22 (1996).
Effros, R.B. et al., Telomere/Telomerase Dynamics Within the Human Immune System: Effect of Chronic Infection and Stress. Exp Gerontol. 46(2-3): 135-40 (2011).
Efron, B. et al., Least angle regression. Ann Statist. 32(2): 407-99 (2004).
Efron, B. et al., On testing the significance of sets of genes. Ann Appl Stat. 1(1): 107-29 (2007).
Egholm, M. et al., Peptide Nucleic Acids (PNA). Oligonucleotide Analogs with an Achiral Peptide Backbone. J Am Chem Soc. 114(5): 1895-7 (1992).
Egholm, M. et al., PNA Hybridizes to Complementary Oligonucleotides Obeying the Watson-Crick Hydrogen-Bonding Rules. Nature. 365(6446): 566-8 (1993).
Ehrlenbach, S. et al., Influences on the reduction of relative telomere length over 10 years in the population-based Bruneck study: introduction of a well-controlled high-throughput assay. Intl J Epidemol. (38): 1725-1734 (2009).
Epel, E.S. et al., Accelerated Telomere Shortening in Response to Life Stress. Proc Natl Acad Sci USA. 101(49): 17312-5 (2004).
Fan, J. et al., Detection of a Novel Avian Influenza A (H7N9) Virus in Humans by Multiplex One-Step Real-Time RT-PCR Assay. BMC Infectious Diseases. 14: 541 (9 pages) (2014).
Farzaneh-Far, R. et al., Telomere Length Trajectory and Its Determinants in Persons with Coronary Asrtery Disease: Longitudinal Findings from the Heart and Soul Study. PloS One. 5(1): e8612 (7 pages) (2010).
Fitzpatrick, A.L. et al., Leukocyte telomere length and mortality in the cardiovascular health study. J Gerontol A Biol Sci Med Sci. 66A(4): 421-9 (2011).

(56) References Cited

OTHER PUBLICATIONS

Föger, N. et al., Requirement for coronin 1 in T lymphocyte trafficking and cellular homeostasis. Science. 313: 839-42 (2006).
Frank, I.E. et al., A statistical view of some chemometrics regression tools (with discussion). Technometrics. 35: 109-48 (1993).
Frenck et al., The Rate of Telomere Sequence Loss in Human Leukocytes Caries with Age. Proc Natl Acad Sci USA. 95: 5607-10 (1998).
Fyhrquist, F. and O. Saijonma, Telomere Length and Cardiovascular Aging. Ann Med. 44(Suppl 1): S138-42 (2012).
Geesaman, B.J. et al., Haplotype-based identification of a microsomal transfer protein marker associated with the human lifespan. Proc Natl Acad Sci USA. 100(24): 14115-20 (2003).
Gertsch, J. et al., Relative quantification of mRNA levels in Jurkat T cells with RT-real time-PCR (RT-rt-PCR): New possibilities for the screening of anti-inflammatory and cytotoxic compounds. Pharm Res. 19(8): 1236-43 (2002).
Goring, H.H. et al., Discovery of expression QTLs using large-scale transcriptional profiling in human lymphocytes. Nat Genet. 39(10): 1208-16 (2007).
Griffith et al., Mammalian Telomeres End in a Large Duplex Loop. Cell. 97: 503-14 (1999).
Gudnason, H. et al., Comparison of Multiple DNA Dyes for Real-Time PCR: Effects of Dye Concentration and Sequence Composition on DNA Amplification and Melting Temperature. Nucleic Acids Res. 35(19): e127 (8 pages) (2007).
Hamilton, B. et al., A systematic RNAi screen for longevity genes in C. elegans. Genes Dev. 19(13): 1544-55 (2005).
Haraldsson, M.K. et al., The lupus-related Lmb3 locus contains a disease-suppressing Coronin-1A gene mutation. Immunity. 28: 40-51 (2008).
Harley, C.B. et al., A Natural Product Telomerase Activator as Part of a Health Maintenance Program, Rejuvenation Res, 14(1): 45-56 (2011).
Harley, C.B. et al., Telomeres shorten during ageing of human fibroblasts. Nature. 345(6274): 458-60 (1990).
Harris et al., The Association Between Telomere Length, Physical Health, Cognitive Ageing, and Mortality in Non-Demented Older People. Neuroscience Lett. 406: 260-4 (2006).
Harrison, D., Oxidative stress and coronary artery disease. Can J Cardiol. 14(suppl D): 30D-2D (1998).
Hemann, M.T. et al., The Shortest Telomere, Not Average Telomere Length, is Critical for Cell Viability and Chromosome Stability. Cell. 107(1): 67-77 (2001).
Henderson, S. et al., In situ analysis of changes in telomere size during replicative aging and cell transformation. J Cell Biol. 134(1): 1-12 (1996).
Herrera, E. et al., Disease states associated with telomerase deficiency appear earlier in mice with short telomeres. EMBO J. 18(11): 2950-2960 (1999).
Higuchi, R. et al., Kinetic PCR analysis: real-time monitoring of DNA amplification reactions. Biotechnology (NY). 11(9): 1026-1030 (1993).
Hoare, M. et al., CD4+ T-Lymphocyte Telomere Length is Related to Fibrosis Stage, Clinical Outcome and Treatement Response in Chronic Hepititis C Virus Infection. J Hepatol. 53(2): 252-60 (2010).
Hoerl, A.E. et al., Ridge regression: Biased estimation for nonorthogonal problems. Technometrics. 41: 80-86 (2000).
Hukezalie, K.R. et al., In Vitro and Ex Vivo Inhibition of Human Telomerase by Anti-HIV Nucleotide Reverse Transcriptase Inhibitors (NRTIs) but Not by Non-NRTIs. PLoS One. 7(11): e47505 (2012).
Hultdin, M. et al., Telomere analysis by fluorescence in situ hybridization and flow cytometry. Nucleic Acids Res. 26(16): 3651-3656 (1998).
Jeanclos, E. et al., Shortened telomere length in white blood cells of patients with IDDM. Diabetes. 47: 482-86 (1998).

Jeffs, P.W. and X. Gao, Unusual Conformation of a 3'-Thioformacetal Linkage in a DNA Duplex. J Biomolecular NMR. 4(1): 17-34 (1994).
Jenkins, G.N. and N.J. Turner, The Biosynthesis of Carbocyclic Nucleosides. Chem Soc Rev. 24: 169-76 (1995).
Johnson, M.R. et al., Quantitation of dihydropyrimidine dehydrogenase expression by real-time reverse transcription polymerase chain reaction. Anal Biochem. 278(2): 175-184 (2000).
Joneja, A. and X. Huang, Linear Nicking Endonuclease-Mediated Strand-Displacement DNA Amplification. Anal Biochem. 414(1): 58-69 (2011).
Jyonouchi, S. et al., Dyskeratosis congenita: a combined immunodeficiency with broad clinical spectrum—a single-center pediatric experience. Pediatr Allergy Immunol. 22(3): 313-9 (2011).
Kainz, P., The PCR plateau phase—towards an understanding of its limitations. Biochim Biophys Acta. 1494: 23-27 (2000).
Kerber, R.A. et al., Familial excess longevity in Utah genealogies. J Gerontol A Biol Sci Med Sci. 56: 6130-139 (2001).
Kerber, R.A. et al., Gene expression profiles associated with aging and mortality in humans. Aging Cell. 8(3): 239-250 (2009).
Kim, N.W. et al., Specific Association of Human Telomerase Activity with Immortal Cells and Cancer. Science. 266: 2011-5 (1994).
Kimura, M. et al., Telomere length and mortality: a study of leukocytes in elderly Danish twins. Am. J. Epidemol. 167(7): 799-806 (2008).
Kimura, M. et al., Measurement of telomere length by the Southern blot analysis of terminal restriction fragment lengths. Nature Proctocols. 5(9): 1596-607 (2010).
Kimura, M. and A. Aviv, Measurement of Telomere DNA Content by Dot Blot Analysis. Nucleic Acids Res. 39(12): e84 (2011).
Koppal, T., DNA Sequencing: Getting to the $1,000 Genome—DNA sequencing technologies strive for higher throughputs and lower costs. Lab Manager. 4(4): 46-47 (2009).
Kuniaki, A. et al., Two independent regions of human telomerase reverse transcriptase are important for its oligomerization and telomerase activity. J. Biol. Chem. 277(10): 8538-8544 (2002).
Kuramoto, M. et al., Identification and analyses of the Xenopus TERT gene that encodes the catalytic subunit of telomerase. Gene. 277: 101-110 (2001).
Lawyer, F. et al., High-level expression, purification, and enzymatic characterization of full-length Thermus aquaticus DNA polymerase and a truncated form deficient in 5' to 3' exonuclease activity. PCR Methods Appl. 2(4): 275-287 (1993).
Lecomte, Ph.J. and O.P. Doubleday, Selective Inactivation of the 3' to 5' Exonndease Activity of *Escherichia coli* DNA Polymerase I by Beat. Nucleic Acids Res. 11(21):7505 (1983).
Letsinger, R.L. and W.S. Mungall, Phosphoramidate Analogs of Oligonucleotides. J Org Chem. 35(11): 3800-3 (1970).
Letsinger, R.L. et al., Effects of Pendant Groups at Phosphorus on Binding Properties of d-ApA Analogues. Nucleic Acids Res. 14(8): 3487-99 (1986).
Letsinger, R.L. et al., Cationic Olgionucleotides. J Am Chem Soc. 110(13): 4470-1 (1988).
Letsinger, R.L. et al., Hybridization of Alternationg Cationic/Anionic Oligonucleotides to RNA Segments. Nucleosides and Nucleotides. 13(6-7): 1597-605 (1994).
Li, B. et al., Rap1 affects the length and heterogeneity of human telomeres. Mol Biol Cell. 14(12): 5060-8 (2003).
Lin, J. et al., Analyses and Comparisons of Telomerase Activity and Telomere Length in Human T and B Cells: Insights for Epidemiology of Telomere Maintenance. J Immunol Methods. 352(1-2): 71-80 (2010).
Liu, H. et al., AffyProbeMiner: a web resource for computing or retrieving accurately redefined Affymetrix probe sets. Bioinformatics. 23: 2385-90 (2007).
Liu, W.M. et al., Analysis of high density expression microarrays with signed-rank call algorithms. Bioinformatics. 18(12): 1593-9 (2002).
Liu, J. et al., Longer Leukocyte Telomere Length Predicts Increased Risk of Hepatitis B Virus-Related Hepatocellular Carcinoma: A Case-Control Analysis. Cancer. 117(18): 4247-56 (2011).

(56) References Cited

OTHER PUBLICATIONS

Loffert, D. et al., PCR optimization: primer design. Qiagen News. 5: 3-6 (1997).
Lundberg, K.S. et al., High-Fidelity Amplification Using a Thermostable DNA Polymerase Isolated from Pyrococcus fuiosus. Gene. 108(1): 1-6 (1991).
Lunetta, K.L. et al., Genetic correlates of longevity and selected age-related phenotypes: a genome-wide association study in the Framingham Study. BMC Med Genet. 8 Suppl 1: S13 (2007).
Ma, H. et al., Shortened Telomere Length Is Associated with Increased Risk of Cancer: A Meta-Analysis. PLoS ONE. 6(6): e20466, (2011).
Mag, M. et al., Synthesis and Slective Cleavage of an Oligodeoxynucleotide Containing a Bridged Internucleotide 5'-Phosphorothioate Linkage. Nucleic Acids Res. 19(7): 1437-41 (1991).
Marchant, J., Spit Test Offers Guide to Health. Nature News: Q&A. Published online May 28, 2011. doi:10.1038/news.2011.330.
Martin-Ruiz, C.M. et al., Reproducibility of Telomere Length Assessment: an International Collaborative Study. Int J Epidemiol. doi: 10.1093/ije/dyu191 (2014).
Marullo, M. et al., Expressed Alu Repeats as a Novel, Reliable Tool for Normalization of Real-Time Quantitative RT-PCR Data. Genome Biol. 11(1): R9 (1-12) (2010).
Masaki, Y. et al., Telomerase activity detected in eyed embryos of rainbow trout *Oncorhynchus mykiss*. Fisheries Science. 68: 132-7 (2002).
Mather, K.A. et al., Is telomere length a biomarker of aging? A review. J Gerontol A Biol Sci Med Sci. 66A(2): 202-13 (2010).
Mathers, J.C., Nutritional modulation of ageing: genomic and epigenetic approaches. Mech Ageing Dev. 127(6): 584-9 (2006).
Mecham, B.H. et al., Sequence-matched probes produce increased cross-platform consistency and more reproducible biological results in microarray-based gene expression measurements. Nucleic Acids Res. 32(9): e74 (2004).
Meier, C. and J.W. Engels, Peptide Nucleic Acids (PNAs)—Unusual Properties of Nonionic Oligonucleotide Analogues. Angew Chem Int Ed Engl. 31(8): 1008-10 (1992).
Merrill, R.M. et al., Impact of the LDS church's health doctrine on deaths from diseases and conditions associated with cigarette smoking. Ann Epidemiol. 13(10): 704-11 (2003).
Monks, S.A. et al., Genetic inheritance of gene expression in human cell lines. Am J Hum Genet. 75(6): 1094-105 (2004).
Morley, M. et al., Genetic analysis of genome-wide variation in human gene expression. Nature. 430(7001): 743-7 (2004).
Morrison, T.B. et al., Quantification of low-copy transcripts by continuous SYBR Green I monitoring during amplification. Biotechniques. 24(6): 954-8, 960, 962 (1998).
Mueller, P. et al., Regulation of T cell survival through coronin-1-mediated generation of inositol-1,4,5-trisphosphate and calcium mobilization after T cell receptor triggering. Nat Immunol. 9(4): 424-31 (2008).
Munoz-Jordan et al., T-Loops at Trypanosome Telomeres. EMBO J. 20: 579-88 (2001).
Myers, T.W. and D.H. Gelfand, Reverse Transcription and DNA Amplification by a Thermus Thermophilus DNA Polymerase. Biochem. 30(31): 7661-6 (1991).
Nakayama, J.I. et al., Stretch PCR Assay. Methods Mol Biol. 191: 125-36 (Mar. 2002).
Nebel, A. et al., No association between microsomal triglyceride transfer protein (MTP) haplotype and longevity in humans. Proc Natl Acad Sci USA. 102(22): 7906-9 (2005).
Nishita, D.M. et al., Clinical trial participant characteristics and saliva and DNA metrics. BMC Medical Research Methodology. 9: 71 (1-10) (2009).
Njajou, O.T. et al., Association between telomere length, specific causes of death, and years of healthy life in health, aging, and body composition, a population-based cohort study. J Gerontol A Biol Sci Med Sci. 64(8): 860-4 (2009).

Nordstrom, B. et al., Characterization of Bacteriophage T7 DNA Polymerase Purified to Homogeneity by Antithioredoxin Immunoadsorbent Chromatography. J Biol Chem. 256(6): 3112-7 (1981).
O'Callaghan, N. et al., A quantitative real-time PCR method for absolute telomere length. Biotechniques. 44(6): 807-9 (2008).
Paeschke, K. et al., Telomeres: Structures in Need of Unwinding. FEBS Lett. 584(17): 3760-72 (2010).
Palmer et al., Telomere Length, Telomerase Activity, and Replicative Potential in HIV Infection: Analysis of CD4+ and CD8+ T Cells from HIV-Discordant Monozygotic Twins, J Exp Med. 185(7): 1381-6 (1997).
Panossian, L.A. et al., Telomere shortening in T cells correlates with Alzheimer's disease status, Neurobiol. Aging. 24(1): 77-84 (2003).
Pommier, J.P. et al., Immunosenescence in HIV Pathogenesis. Virology. 231(1): 148-54 (1997).
Poon, S.S. et al., Telomere Length Measurements Using Digital Fluorescence Microscopy, Cytometry, 36(4): 267-78 (1999).
Powers, R.W. et al., Extension of chronological life span in yeast by decreased TOR pathway signaling. Genes Dev. 20(2): 174-84 (2006).
Puca, A.A. et al., A genome-wide scan for linkage to human exceptional longevity identifies a locus on chromosome 4. Proc Natl Acad Sci USA. 98(18): 10505-8 (2001).
Puterman, E. and E. Epel, An Intricate Dance: Life Experience, Multisystem Resiliency, and Rate of Telomere Decline Throughout the lifespan. Soc Personal Psychol Compass. 6(11): 807-25 (2012).
Rattan, S.I.S. et al., Increased Molecular Damage and Heterogeneity as the Basis of Aging. Biol Chem. 389(3): 267-72 (2008).
Reiner, A. et al., Identifying differentially expressed genes using false discovery rate controlling procedures. Bioinformatics. 19, 368-75 (2003).
Relative fluorescence unit (RFU), DNA.gov: Glossary, Apr. 2011 (found at http://web.archive.org/web/20110506061955/http://www.dna.gov/glossary#R; retrieved on Dec. 23, 2014) (1 page).
Ruchaud, S. et al., Chromosomal passengers: conducting cell division. Nat Rev Mol Cell Biol. 8(10): 798-812 (2007).
Rudolph, K.L. et al., Longevity, Stress Response, and Cancer in Aging Telomerase-Deficient Mice. Cell. 96(5): 701-12 (1999).
Rufer, N. et al., Telomere Length Dynamics in Human Lymphocyte Subpopulations Measured by Flow Cytometry. Nat Biotechnol. 16(8): 743-7 (1998).
Rufer, N. et al., Telomere fluorescence measurements in granulocytes and T lymphocyte subsets point to a high turnover of hematopoietic stem cells and memory T cells in early childhood. J Exp Med. 190(2): 157-67 (1999).
Ryder, M.I. et al., Alteration of gene expression profiles of peripheral mononuclear blood cells by tobacco smoke: implications for periodontal diseases. Oral Microbiol Immunol. 19(1): 39-49 (2004).
Rylander-Rudqvist, T. et al., Quality and quantity of saliva DNA obtained from the self-administrated oragene method—a pilot study on the cohort of Swedish men. Cancer Epidemiol Biomarkers Prev. 15(9): 1742-5 (2006).
Salpea, K. and S.E. Humphries, Telomere length in atherosclerosis and diabetes. Atherosclerosis. 209(1): 35-8 (2010).
Samani et al., Telomere Shortening in Atherosclerosis. Lancet. 358: 472-3 (2001).
Sampson, M.J. and D.A. Hughes, Chromosomal telomere attrition as a mechanism for the increased risk of epithelial cancers and senescent phenotypes in type 2 diabetes. Diabetologia. 49: 1726-31 (2006).
Sanders et al., Telomere Length in Epidemiology: A Biomarker of Aging, Age-Related Disease, Both, or Neither? Epidemiologic Review., 35: 112-31 (2013).
Satoh, M. et al., Effect of intensive lipid lowering therapy on telomere erosion in endothelial progenitor cells obtained from patients with coronary artery disease. Clin Sci. 116: 827-35 (2009).
Sawai, H. et al., Synthesis and Properties of Oligoadenylic Acids Conaining 2'-5' Phosphoramide Linkage. Chem Lett. 13(5): 805-8 (1984).
Schadt, E.E. et al., Genetics of gene expression surveyed in maize, mouse and man. Nature. 422(6929): 297-302 (2003).

(56) References Cited

OTHER PUBLICATIONS

Scheinberg, P. et al., Association of Telomere Length of Peripheral Blood Leukocytes With Hematopoietic Relapse, Malignant Transformation, and Survival in Severe Aplastic Anemia. JAMA. 304(12): 1358-64 (2010).
Segal, M.R., Microarray gene expression data with linked survival phenotypes: diffuse large-B-cell lymphoma revisited. Biostatistics. 7(2): 268-285 (2006).
Seong, K.H. et al., Application of the gene search system to screen for longevity genes in *Drosophila*. Biogerontology. 2(3): 209-17 (2001).
Sheffield, V.C. et al., Attachment of a 40-base-pair G+C-rich sequence (GC-clamp) to genomic DNA fragments by the polymerase chain reaction results in improved detection of single-base changes. Proc Natl Acad Sci USA. 86: 232-236 (1989).
Shen, J. et al., Telomere length, oxidative damage, antioxidants and breast cancer risk. Int J Cancer. 124(7): 1637-43 (2009).
Shiow, L.R. et al., The actin regulator coronin 1A is mutant in a thymic egress-deficient mouse strain and in a patient with severe combined immunodeficiency. Nat Immunol. 9(11): 1307-15 (2008).
Smith, B., Rinse, Swab, or Spit—What's the Real Source of DNA in Saliva?, DNA Genotek's Sample Collection Blog (Mar. 31, 2010? From http://blog.dnagenotek.com/blogdnagenotekcom.
Southern, E.M., Detection of specific sequences among DNA fragments separated by gel electrophoresis. J Mol Biol. 98(3): 503-17 (1975).
Sprinzl, M. et al., Enzymatic Incorporation of ATP and CTP Analogues into the 3' End of tRNA. Eur J Biochem. 81(3): 579-89 (1977).
Steer, S.E. et al., Reduced telomere length in rheumatoid arthritis is independent of disease activity and duration. An Rheum Dis. 66(4): 476-80 (2007).
Stenesh, J. and G.R. McGowan, DNA Polymerase from Mesophilic and Thermophilic Bacteria. III. Lack of Fidelity in the Replication of Synthetic Polydeoxyribonucleotides by DNA Polymerase from Bacillus licheniformis and Bacillus stearothermophilus. Biochim Biophys Acta. 475(1): 32-41 (1977).
Strahl, C. and E.H. Blackburn, Effects of Reverse Transcriptase Inhibitors on Telomere Length and Telomerase Activity in Two Immortalized Human Cell Lines. Mol Cell Biol. 16(1): 53-65 (1996).
Stranger, B.E. et al., Genome-Wide Associations of Gene Expression Variation in Humans. PLoS Genet .1(6): e78 (2005).
Svenson, U. et al., Breast cancer survival is associated with telomere length in peripheral blood cells. Cancer Res. 68(10): 3618-23 (2008).
Talasaz, A.H. et al., Isolating Highly Enriched Populations of Circulating Epithelial Cells and Other Rare Cells from Blood Using a Magnetic Sweeper Device. Proc Natl Acad Sci USA. 106(10): 3970-5 (2009).
Tatematsu, K. et al., A novel quantitative 'stretch PCR assay', that detects a dramatic increase in telomerase activity during the progression of myeloid leukemias. Oncogene. 13: 2265-74 (1996).
Tentolouris, N. et al., White blood cells telomere length is shorter in males with type 2 diabetes and microalbuminuria. Diabetes Care. 30(11): 2909-15 (2007).
Therneau, T.M., On mixed-effect Cox models, sparse matrices, and modeling data from large pedigrees. Paper presented on Dec. 31, 2007; available at http://mayoresearch.mayo.edu/mayo/research/biostat/upload/kinship.pdf (2007).
Tibshirani, R., Regression Shrinkage and Selection via the Lasso. J R Stat Soc Series B. 58(1): 267-88 (1996).
Uziel, O. et al., Telomere dynamics in arteries and mononuclear cells of diabetic patients: effect of diabetes and of glycemic control. Exp Gerontology. 42: 971-8 (2007).
Valdes, A.M. et al., Obesity, cigarette smoking, and telomere length in women. Lancet. 366: 662-4 (2005).
Valls, C. et al., Telomere Length is a Pronostic Factor for Overall Survival in Colorectal Cancer. Colorectal Dis. 13(11): 1265-72 (2011).
Van Leeuwen, D.M. et al., Differential gene expression in human peripheral blood mononuclear cells induced by cigarette smoke and its constituents. Toxicol Sci. 86(1): 200-210 (2005).
Vander Griend, D.J. et al., Dual-Label Centromere and Telomere Fish Identifies Human, Rat, and Mouse Cell Contribution to Multispecies Recombinant Urogenital Sinus Xenografts. Prostate. 69(14): 1557-64 (2009).
Vera, E. et al., The Rate of Increase of Short Telomeres Predicts Longevity in Mammals. Cell Rep. 2(4): 732-7 (2012).
Verzola, D. et al., Accelerated senescence in the kidneys of patients with type 2 diabetic nephropathy. Am J Physiol. 295: F1563-73 (2008).
Vincent, M. et al., Helicase-Dependent Isothermal DNA Amplification. EMBO Rep. 5(8): 795-800 (2004).
Von Ahsen, N. et al., Application of a Thermodynamic Nearest-Neighbor Model to Estimate Nucleic Acid Stability and Optimize Probe Design: Prediction of Melting Points of Multiple Mutations of Apolipoprotein B3500 and Factor V with a Hybridization Probe Genotyping Assay on the LightCycler. Clin Chem. 45(12): 2094-101 (1999).
Von Kiedrowski, G. et al., Parabolic Growth of a Self-Replicating Hexadeoxynucleotide Bearing a 3'-5'-Phosphoamidate Linkage. Angew Chem Int Ed Engl. 30(4): 423-6 (1991).
Von Zglinicki, T., Role of oxidative stress in telomere length regulation and replicative senescence. Ann NY Acad Sci. 908: 99-110 (2000).
Wang, L. et al., Cdc42 GTPase-activating protein deficiency promotes genomic instability and premature aging-like phenotypes. Proc Natl Acad Sci USA. 104(4): 1248-1253 (2007).
Ware, J.E., SF-36® Health Survey Update, (found at http://www.sf-36.org/tools/SF36.shtml; retrieved on Dec. 21, 2014) (18 pages).
Wetmur, J.G., DNA Probes: Application of the Principles of Nucleic Acid Hybridization. Crit Rev Biochem Mol Biol. 26(3-4): 227-59 (1991).
White, R. et al., Construction of linkage maps with DNA markers for human chromosomes. Nature. 313(5998): 101-105 (1985).
Wiemann, S U et al. Hepatocyte telomere shortening and senescence are general markers of human liver cirrhosis. FASEB J. 16(9): 935-82 (2002).
Wikgren, M. et al., Short Telomeres in Depression and the General Population Are Associated with a Hypocortisolemic State. Biol Psychiatry. 71: 294-300 (2011).
Willeit, P. et al., Telomere length and risk of incident cancer and cancer mortality. JAMA. 304(1): 69-75 (2010).
Wilson, C.L. et al., Amplification protocols introduce systematic but reproducible errors into gene expression studies. Biotechniques. 36(3): 498-506 (2004).
Wittwer, C.T. et al., Real-time multiplex PCR assays. Methods. 25(4): 430-442 (2001).
Wolkowitz, O.M. et al., Leukocyte Telomere Length in Major Depression: Correlations with Chronicity, Inflammation and Oxidative Stress—Preliminary Findings, PLoS One, 6(3): e17837 (1-10) (2011).
Wu, Z. et al., Stochastic models inspired by hybridization theory for short oligonucleotide arrays. J Comput Biol. 12(6): 882-893 (2005).
Wylie, J.E. et al., Biomedical databases: protecting privacy and promoting research. Trends Biotechnol. 21(3): 113-116 (2003).
Xu, L. and E.H. Blackburn, Human Cancer Cells Harbor T-Stumps, a Distinct Class of Extremely Short Telomeres. Mol Cell. 28(2): 315-27 (2007).
Yang, J. et al., AZD1152, a novel and selective aurora B kinase inhibitor, induces growth arrest, apoptosis, and sensitization for tubulin depolymerizing agent or topoisomerase II inhibitor in human acute leukemia cells in vitro and in vivo. Blood. 110(6): 2034-2040 (2007).
Yoon, M. et al., Immobilization of antibodies on the self-assembled monolayer by antigen-binding site protection and immobilization kinetic control. J Biomed Sci Engr. 4: 242-247 (2011).
Zekry et al., Telomere Length, Comorbidity, Functional, Nutritional, and Cognitive Status as Predictors of 5 Years Post Hospital Discharge Survival in the Oldest Old. J Nutr Health Aging. 16(3): 225-30 (2012) (Abstract only; Retrieved on Jan. 3, 2014 from http://www.ncbi.nlm.nih.gov/pubmed/22456777).

(56) References Cited

OTHER PUBLICATIONS

Zhang, W. et al., Gender-specific differences in expression in human lymphoblastoid cell lines. Pharmacogenet Genomics. 17(6): 447-450 (2007).
Zhang, X. et al., Telomere shortening and apoptosis in telomerase-inhibited human tumor cells. Genes Dev. 13(18): 2388-2399 (1999).
Zhu, H. et al., Healthy Aging and Disease: Role for Telomere Biology? Clin Sci (Lond). 120(10):427-40 (2011).
Zijlmans, J.M. et al., Telomeres in the mouse have large inter-chromosomal variations in the number of T2AG3 repeats. Proc Natl Acad Sci USA. 94(14): 7423-7428 (1997).
Examination Report No. 1 dated Aug. 4, 2015 by the Intellectual Property Office of Australia for Australian Patent Application No. 2009329987, which was filed on Jun. 27, 2011 (Applicant—University of Utah; Inventor—Cawthon et al.) (3 pages).
Notice of Abandonment dated Feb. 16, 2015 by the Canadian Intellectual Property Office for Canadian Patent Application No. 2748265, which was filed on Jun. 22, 2011 (Applicant—University of Utah; Inventor—Cawthon et al.) (1 page).
Notice of Amendment and Completion of Formalities dated Sep. 29, 2011 for Chinese application No. 200980157269.8, which claims priority to PCT/US2009/069243, filed on Dec. 22, 2009. (Applicant—University of Utah; Inventor—Cawthon et al.) (3 pages).
Response to Notice of Amendment and Completion of Formalities dated Jan. 19, 2012 for Chinese application No. 200980157269.8, which claims priority to PCT/US2009/069243, filed on Dec. 22, 2009. (Applicant—University of Utah; Inventor—Cawthon et al.) (2 pages).
Notice of Passing Preliminary Exam dated Feb. 10, 2012 for Chinese application No. 200980157269.8, which claims priority to PCT/US2009/069243, filed on Dec. 22, 2009. (Applicant—University of Utah; Inventor—Cawthon et al.) (1 page).
First Office Action dated May 6, 2013 by the State Intellectual Property Office of the People's Republic of China for Chinese Patent Application No. 2009801572698, which was filed on Aug. 22, 2011 and published as CN102439171 on May 2, 2012 (Applicant—University of Utah; Inventor—Cawthon et al.) (12 pages).
Second Office Action dated Dec. 26, 2013 by the State Intellectual Property Office of the People's Republic of China for Chinese Patent Application No. 2009801572698, which was filed on Aug. 22, 2011 and published as CN102439171 on May 2, 2012 (Applicant—University of Utah; Inventor—Cawthon et al.) (13 pages).
Decision on Rejection dated Jul. 8, 2014 by the State Intellectual Property Office of the People's Republic of China for Chinese Patent Application No. 2009801572698, which was filed on Aug. 22, 2011 and published as CN102439171 on May 2, 2012 (Applicant—University of Utah; Inventor—Cawthon et al.) (12 pages).
Communication Pursuant to Rules 161(1) and 162 EPC dated Aug. 2, 2011 for European application No. 09804177.5, which was filed on Dec. 22, 2009 and granted as 2379747 on Jul. 3, 2013 (Applicant—University of Utah; Inventor—Cawthon et al.) (2 pages).
Amendment before examination filed on Feb. 13, 2012 for European application No. 09804177.5, which was filed on Dec. 22, 2009 and granted as 2379747 dated Jul. 3, 2013 (Applicant—University of Utah; Inventor—Cawthon et al.) (18 pages).
Decision to Grant dated Jun. 6, 2013 for European application No. 09804177.5, which was filed on Dec. 22, 2009 and granted as 2379747 dated Jul. 3, 2013 (Applicant—University of Utah; Inventor—Cawthon et al.) (2 pages).
Certificate of Patent dated Jul. 3, 2013 for European application No. 09804177.5, which was filed on Dec. 22, 2009 and granted as 2379747 dated Jul. 3, 2013 (Applicant—University of Utah; Inventor—Cawthon et al.) (39 pages).
Office Action dated Jun. 4, 2014 by the Japan Patent Office for Japanese Patent Application No. 2011-543646, which was filed on Jun. 22, 2011 and published on Jun. 14, 2012 (Applicant—University of Utah; Inventor—Cawthon et al.) (4 pages).

Office Action dated May 7, 2015 by the Japan Patent Office for Japanese Patent Application No. 2011-543646, which was filed on Jun. 22, 2011 and published on Jun. 14, 2012 (Applicant—University of Utah; Inventor—Cawthon et al.) (3 pages).
Notice of Allowance dated Oct. 21, 2015 by the Japan Patent Office for Japanese Patent Application No. 2011-543646, which was filed on Jun. 22, 2011 and published on Jun. 14, 2012 (Applicant—University of Utah; Inventor—Cawthon et al.) (3 pages).
International Search Report dated Mar. 30, 2010 for PCT/US2009/069243, filed on Dec. 22, 2009 and published as WO 2010/075413 on Jul. 1, 2010 (Applicant—University of Utah; Inventor—Cawthon et al.) (5 pages).
Written Opinion of International Search Report dated Jun. 22, 2011 for PCT/US2009/069243, filed on Dec. 22, 2009 and published as WO 2010/075413 on Jul. 1, 2010 (Applicant—University of Utah; Inventor-Cawthon et al.) (5 pages).
International Preliminary Report on patentability dated Jun. 22, 2011 for PCT/US2009/069243, filed on Dec. 22, 2009 and published as WO 2010/075413 on Jul. 1, 2010 (Applicant—University of Utah; Inventor—Cawthon et al.) (6 pages).
Preliminary Amendment filed on Jun. 22, 2011 for U.S. Appl. No. 13/141,429, filed Aug. 15, 2011 and published as US 2011/0294676 on Dec. 1, 2011 (Applicant—University of Utah; Inventor—Cawthon et al.) (3 pages).
Restriction Requirement dated Aug. 20, 2014 for U.S. Appl. No. 13/141,429, filed Aug. 15, 2011 and published as US 2011/0294676 on Dec. 1, 2011 (Applicant—University of Utah; Inventor—Cawthon et al.) (10 pages).
Response to Restriction Requirement filed on Oct. 20, 2014 for U.S. Appl. No. 13/141,429, filed Aug. 15, 2011 and published as US 2011/0294676 on Dec. 1, 2011 (Applicant—University of Utah; Inventor—Cawthon et al.) (9 pages).
Non-Final Office Action dated Jan. 23, 2015 for U.S. Appl. No. 13/141,429, filed Aug. 15, 2011 and published as US 2011/0294676 on Dec. 1, 2011 (Applicant—University of Utah; Inventor—Cawthon et al.) (8 pages).
Response to Non-Final Office Action filed on Apr. 23, 2015 for U.S. Appl. No. 13/141,429, filed Aug. 15, 2011 and published as US 2011/0294676 on Dec. 1, 2011 (Applicant—University of Utah; Inventor—Cawthon et al.) (15 pages).
Non-Final Office Action dated Jun. 18, 2015 for U.S. Appl. No. 13/141,429, filed Aug. 15, 2011 and published as US 2011/0294676 on Dec. 1, 2011 (Applicant—University of Utah; Inventor—Cawthon et al.) (7 pages).
Response to Non-Final Office Action filed on Oct. 15, 2015 for U.S. Appl. No. 13/141,429, filed Aug. 15, 2011 and published as US 2011/0294676 on Dec. 1, 2011 (Applicant—University of Utah; Inventor—Cawthon et al.) (9 pages).
Request for examination filed on May 3, 2006 for Australian application No. 2003208902, which claims priority to PCT/US2003/002844, filed on Jan. 31, 2003. (Applicant—University of Utah; Inventor—Cawthon et al.) (1 page).
Office Action dated Mar. 29, 2007 for Australian application No. 2003208902, which claims priority to PCT/US2003/002844, filed on Jan. 31, 2003. (Applicant—University of Utah; Inventor—Cawthon et al.) (2 pages).
Response to Office Action filed on Jul. 23, 2008 for Australian application No. 2003208902, which claims priority to PCT/US2003/002844, filed on Jan. 31, 2003. (Applicant—University of Utah; Inventor—Cawthon et al.) (16 pages).
Notice of Acceptance dated Jul. 25, 2008 for Australian application No. 2003208902, which claims priority to PCT/US2003/002844, filed on Jan. 31, 2003. (Applicant—University of Utah; Inventor—Cawthon et al.) (7 pages).
Preliminary Amendment filed on Sep. 20, 2004 for Canadian application No. 2474468, which claims priority to PCT/US2003/002844, filed on Jan. 31, 2003. (Applicant—University of Utah; Inventor—Cawthon et al.) (3 pages).
Office Action dated Jul. 22, 2010 for Canadian application No. 2474468, which claims priority to PCT/US2003/002844, filed on Jan. 31, 2003. (Applicant—University of Utah; Inventor—Cawthon et al.) (4 pages).

(56) References Cited

OTHER PUBLICATIONS

Response to Office Action filed on Jan. 20, 2011 for Canadian application No. 2474468, which claims priority to PCT/US2003/002844, filed on Jan. 31, 2003. (Applicant—University of Utah; Inventor—Cawthon et al.) (3 pages).
Office Action dated Jul. 13, 2011 for Canadian application No. 2474468, which claims priority to PCT/US2003/002844, filed on Jan. 31, 2003. (Applicant—University of Utah; Inventor—Cawthon et al.) (2 pages).
Response to Office Action filed on Jan. 13, 2012 for Canadian application No. 2474468, which claims priority to PCT/US2003/002844, filed on Jan. 31, 2003. (Applicant—University of Utah; Inventor—Cawthon et al.) (15 pages).
Office Action dated May 29, 2012 for Canadian application No. 2474468, which claims priority to PCT/US2003/002844, filed on Jan. 31, 2003. (Applicant—University of Utah; Inventor—Cawthon et al.) (2 pages).
Response to Office Action filed on Nov. 29, 2012 for Canadian application No. 2474468, which claims priority to PCT/US2003/002844, filed on Jan. 31, 2003. (Applicant—University of Utah; Inventor—Cawthon et al.) (9 pages).
Notice of Allowance dated Jul. 23, 2013 for Canadian application No. 2474468, which claims priority to PCT/US2003/002844, filed on Jan. 31, 2003. (Applicant—University of Utah; Inventor—Cawthon et al.) (1 page).
Certificate of Patent dated Mar. 25, 2014 for Canadian application No. 2474468, which claims priority to PCT/US2003/002844, filed on Jan. 31, 2003. (Applicant—University of Utah; Inventor—Cawthon et al.) (1 page).
Office Action dated Mar. 17, 2006 for Chinese application No. 03804867.1, which claims priority to PCT/US2003/002844, filed on Jan. 31, 2003. (Applicant—University of Utah; Inventor—Cawthon et al.) (4 pages).
Response to Office Action filed on Sep. 19, 2006 for Chinese application No. 03804867.1, which claims priority to PCT/US2003/002844, filed on Jan. 31, 2003. (Applicant—University of Utah; Inventor—Cawthon et al.) (5 pages).
Notice of Acceptance dated Apr. 1, 2009 for Chinese application No. 03804867.1, which claims priority to PCT/US2003/002844, filed on Jan. 31, 2003. (Applicant—University of Utah; Inventor—Cawthon et al.) (2 pages).
Request for examination filed on Aug. 20, 2004 for European application No. 03707624.7, which claims priority to PCT/US2003/002844, filed on Jan. 31, 2003. (Applicant—University of Utah; Inventor—Cawthon et al.) (7 pages).
Office Action dated Oct. 26, 2006 for European application No. 03707624.7, which claims priority to PCT/US2003/002844, filed on Jan. 31, 2003. (Applicant—University of Utah; Inventor—Cawthon et al.) (7 pages).
Response to Office Action filed on Aug. 21, 2007 for European application No. 03707624.7, which claims priority to PCT/US2003/002844, filed on Jan. 31, 2003. (Applicant—University of Utah; Inventor—Cawthon et al.) (9 pages).
Office Action dated Dec. 13, 2007 for European application No. 03707624.7, which claims priority to PCT/US2003/002844, filed on Jan. 31, 2003. (Applicant—University of Utah; Inventor—Cawthon et al.) (6 pages).
Response to Office Action filed on Sep. 17, 2008 for European application No. 03707624.7, which claims priority to PCT/US2003/002844, filed on Jan. 31, 2003. (Applicant—University of Utah; Inventor—Cawthon et al.) (7 pages).
Office Action dated Oct. 13, 2010 for European application No. 03707624.7, which claims priority to PCT/US2003/002844, filed on Jan. 31, 2003. (Applicant—University of Utah; Inventor—Cawthon et al.) (6 pages).
Response to Office Action filed on Jan. 18, 2011 for European application No. 03707624.7, which claims priority to PCT/US2003/002844, filed on Jan. 31, 2003. (Applicant—University of Utah; Inventor—Cawthon et al.) (20 pages).
Intention to Grant dated Jun. 6, 2011 for European application No. 03707624.7, which claims priority to PCT/US2003/002844, filed on Jan. 31, 2003. (Applicant—University of Utah; Inventor—Cawthon et al.) (5 pages).
Certificate of Grant dated Nov. 23, 2011 for European application No. 03707624.7, which claims priority to PCT/US2003/002844, filed on Jan. 31, 2003. (Applicant—University of Utah; Inventor—Cawthon et al.) (1 page).
Request for Registration filed on Feb. 11, 2012 for Hong Kong application No. 05103554.7, which claims priority to PCT/US2003/002844, filed on Jan. 31, 2003. (Applicant—University of Utah; Inventor—Cawthon et al.) (1 page).
Certificate of Grant dated Jun. 15, 2012 for Hong Kong application No. 05103554.7, which claims priority to PCT/US2003/002844, filed on Jan. 31, 2003. (Applicant—University of Utah; Inventor—Cawthon et al.) (4 pages).
Office Action dated Oct. 7, 2008 for Japanese application No. 2003-564211, which claims priority to PCT/US2003/002844, filed on Jan. 31, 2003. (Applicant—University of Utah; Inventor—Cawthon et al.) (2 pages).
Response to Office Action filed on Apr. 7, 2009 for Japanese application No. 2003-564211, which claims priority to PCT/US2003/002844, filed on Jan. 31, 2003. (Applicant—University of Utah; Inventor—Cawthon et al.) (4 pages).
Office Action dated May 7, 2009 for Japanese application No. 2003-564211, which claims priority to PCT/US2003/002844, filed on Jan. 31, 2003. (Applicant—University of Utah; Inventor—Cawthon et al.) (1 page).
Response to Office Action filed on Sep. 7, 2009 for Japanese application No. 2003-564211, which claims priority to PCT/US2003/002844, filed on Jan. 31, 2003. (Applicant—University of Utah; Inventor—Cawthon et al.) (6 pages).
Office Action dated Nov. 4, 2009 for Japanese application No. 2003-564211, which claims priority to PCT/US2003/002844, filed on Jan. 31, 2003. (Applicant—University of Utah; Inventor—Cawthon et al.) (1 page).
Response to Office Action filed on Apr. 27, 2010 for Japanese application No. 2003-564211, which claims priority to PCT/US2003/002844, filed on Jan. 31, 2003. (Applicant—University of Utah; Inventor—Cawthon et al.) (1 page).
Notice of Grant and Translated Claims issued May 21, 2010 for Japanese application No. 2003-564211, which claims priority to PCT/US2003/002844, filed on Jan. 31, 2003. (Applicant—University of Utah; Inventor—Cawthon et al.) (21 pages).
International search report dated Feb. 26, 2004 for PCT/US2003/002844, filed on Jan. 31, 2003 (Applicant—University of Utah; Inventor—Cawthon et al.) (3 pages).
International preliminary report on patentability dated Nov. 16, 2004 for PCT/US2003/002844, filed on Jan. 31, 2003 and published as WO 2003/064615 on Aug. 7, 2003 (Applicant—University of Utah; Inventor—Cawthon et al.) (3 pages).
Preliminary Amendment filed on Apr. 29, 2003 for U.S. Appl. No. 10/355,626, filed Jan. 31, 2003, now U.S. Pat. No. 7,695,904 on Apr. 13, 2010 (Applicant—University of Utah; Inventor—Cawthon et al.) (9 pages).
Preliminary Amendment filed on Feb. 17, 2005 for U.S. Appl. No. 10/355,626, filed Jan. 31, 2003, now U.S. Pat. No. 7,695,904 on Apr. 13, 2010 (Applicant—University of Utah; Inventor—Cawthon et al.) (9 pages).
Restriction Requirement dated May 2, 2006 for U.S. Appl. No. 10/355,626, filed Jan. 31, 2003, now U.S. Pat. No. 7,695,904 on Apr. 13, 2010 (Applicant—University of Utah; Inventor—Cawthon et al.) (6 pages).
Response to Restriction Requirement filed on Jun. 5, 2006 for U.S. Appl. No. 10/355,626, filed Jan. 31, 2003, now U.S. Pat. No. 7,695,904 on Apr. 13, 2010 (Applicant—University of Utah; Inventor—Cawthon et al.) (7 pages).
Restriction Requirement filed on Aug. 9, 2006 for U.S. Appl. No. 10/355,626, filed Jan. 31, 2003, now U.S. Pat. No. 7,695,904 on Apr. 13, 2010 (Applicant—University of Utah; Inventor—Cawthon et al.) (8 pages).

(56) References Cited

OTHER PUBLICATIONS

Response to Restriction Requirement filed on Mar. 2, 2007 for U.S. Appl. No. 10/355,626, filed Jan. 31, 2003, now U.S. Pat. No. 7,695,904 on Apr. 13, 2010 (Applicant—University of Utah; Inventor—Cawthon et al.) (8 pages).
Notice of Abandonment dated Mar. 6, 2007 for U.S. Appl. No. 10/355,626, filed Jan. 31, 2003, now U.S. Pat. No. 7,695,904 on Apr. 13, 3010 (Applicant—University of Utah; Inventor—Cawthon et al.) (2 pages).
Office Action dated Aug. 6, 2007 for U.S. Appl. No. 10/355,626, filed Jan. 31, 2003, now U.S. Pat. No. 7,695,904 on Apr. 13, 2010 (Applicant—University of Utah; Inventor—Cawthon et al.) (18 pages).
Response to Office Action filed on Jan. 22, 2008 for U.S. Appl. No. 10/355,626, filed Jan. 31, 2003, now U.S. Pat. No. 7,695,904 on Apr. 13, 2010 (Applicant—University of Utah; Inventor—Cawthon et al.) (19 pages).
Office Action dated Mar. 27, 2008 for U.S. Appl. No. 10/355,626, filed Jan. 31, 2003, now U.S. Pat. No. 7,695,904 on Apr. 13, 2010 (Applicant—University of Utah; Inventor—Cawthon et al.) (18 pages).
Response to Office Action filed on Jun. 27, 2008 for U.S. Appl. No. 10/355,626, filed Jan. 31, 2003, now U.S. Pat. No. 7,695,904 on Apr. 13, 2010 (Applicant—University of Utah; Inventor—Cawthon et al.) (10 pages).
Notice of Appeal filed on Sep. 26, 2008 for U.S. Appl. No. 10/355,626, filed Jan. 31, 2003, now U.S. Pat. No. 7,695,904 on Apr. 13, 2010 (Applicant—University of Utah; Inventor—Cawthon et al.) (1 page).
Advisory Action dated Oct. 7, 2008 for U.S. Appl. No. 10/355,626, filed Jan. 31, 2003, now U.S. Pat. No. 7,695,904 on Apr. 13, 2010 (Applicant—University of Utah; Inventor—Cawthon et al.) (3 pages).
Office Action dated Jan. 22, 2009 for U.S. Appl. No. 10/355,626, filed Jan. 31, 2003, now U.S. Pat. No. 7,695,904 on Apr. 13, 2010 (Applicant—University of Utah; Inventor—Cawthon et al.) (8 pages).
Response to Office Action filed on Jul. 22, 2009 for U.S. Appl. No. 10/355,626, filed Jan. 31, 2003, now U.S. Pat. No. 7,695,904 on Apr. 13, 2010 (Applicant—University of Utah; Inventor—Cawthon et al.) (11 pages).
Notice of Allowance dated Nov. 17, 2009 for U.S. Appl. No. 10/355,626, filed Jan. 31, 2003, now U.S. Pat. No. 7,695,904 on Apr. 13, 2010 (Applicant—University of Utah; Inventor—Cawthon et al.) (6 pages).
Issue Notification dated Mar. 24, 2010 for U.S. Appl. No. 10/355,626, filed Jan. 31, 2003, now U.S. Pat. No. 7,695,904 on Apr. 13, 2010 (Applicant—University of Utah; Inventor—Cawthon et al.) (1 page).
Restriction Requirement dated Jul. 8, 2010 for U.S. Appl. No. 12/700,475, filed Feb. 4, 2010, now U.S. Pat. No. 8,048,631 on Nov. 1, 2011 (Applicant—University of Utah; Inventor—Cawthon et al.) (6 pages).
Response to Restriction Requirement filed on Aug. 9, 2010 for U.S. Appl. No. 12/700,475, filed Feb. 4, 2010, now U.S. Pat. No. 8,048,631 on Nov. 1, 2011 (Applicant—University of Utah; Inventor—Cawthon et al.) (10 pages).
Office Action dated Oct. 28, 2010 for U.S. Appl. No. 12/700,475, filed Feb. 4, 2010, now U.S. Pat. No. 8,048,631 on Nov. 1, 2011 (Applicant—University of Utah; Inventor—Cawthon et al.) (8 pages).
Response to Office Action filed on Mar. 28, 2011 for U.S. Appl. No. 12/700,475, filed Feb. 4, 2010, now U.S. Pat. No. 8,048,631 on Nov. 1, 2011 (Applicant—University of Utah; Inventor—Cawthon et al.) (14 pages).
Supplemental Application Data Sheet filed on Jun. 15, 2011 for U.S. Appl. No. 12/700,475, filed Feb. 4, 2010, now U.S. Pat. No. 8,048,631 on Nov. 1, 2011 (Applicant—University of Utah; Inventor—Cawthon et al.) (14 pages).
Notice of Allowance dated Jun. 27, 2011 for U.S. Appl. No. 12/700,475, filed Feb. 4, 2010, now U.S. Pat. No. 8,048,631 on Nov. 1, 2011 (Applicant—University of Utah; Inventor—Cawthon et al.) (10 pages).
Issue Notification dated Oct. 12, 2011 for U.S. Appl. No. 12/700,475, filed Feb. 4, 2010, now U.S. Pat. No. 8,048,631 on Nov. 1, 2011 (Applicant—University of Utah; Inventor—Cawthon et al.) (1 page).
Office Action dated Mar. 8, 2011 for Canadian application No. 2513747, which claims priority to PCT/US2004/002215, filed on Jan. 26, 2004. (Applicant—University of Utah; Inventor—Cawthon et al.) (3 pages).
Response to Office Action filed on Sep. 8, 2011 for Canadian application No. 2513747, which claims priority to PCT/US2004/002215, filed on Jan. 26, 2004. (Applicant—University of Utah; Inventor—Cawthon et al.) (23 pages).
Office Action dated Apr. 16, 2012 for Canadian application No. 2513747, which claims priority to PCT/US2004/002215, filed on Jan. 26, 2004. (Applicant—University of Utah; Inventor—Cawthon et al.) (3 pages).
Response to Office Action filed on Oct. 16, 2012 for Canadian application No. 2513747, which claims priority to PCT/US2004/002215, filed on Jan. 26, 2004. (Applicant—University of Utah; Inventor—Cawthon et al.) (10 pages).
Office Action dated Oct. 22, 2015 for Canadian application No. 2513747, which claims priority to PCT/US2004/002215, filed on Jan. 26, 2004. (Applicant—University of Utah; Inventor—Cawthon et al.) (5 pages).
Office Action dated Jan. 22, 2010 for European application No. 04705326.9, which claims priority to PCT/US2004/002215, filed on Jan. 26, 2004. (Applicant—University of Utah; Inventor—Cawthon et al.) (6 pages).
Response to Office Action filed on Jun. 21, 2010 for European application No. 04705326.9, which claims priority to PCT/US2004/002215, filed on Jan. 26, 2004. (Applicant—University of Utah; Inventor—Cawthon et al.) (6 pages).
Office Action dated Dec. 27, 2011 for European application No. 04705326.9, which claims priority to PCT/US2004/002215, filed on Jan. 26, 2004. (Applicant—University of Utah; Inventor—Cawthon et al.) (7 pages).
Office Action dated Feb. 21, 2012 for European application No. 04705326.9, which claims priority to PCT/US2004/002215, filed on Jan. 26, 2004. (Applicant—University of Utah; Inventor—Cawthon et al.) (2 pages).
Response to Office Action filed Apr. 30, 2012 for European application No. 04705326.9, which claims priority to PCT/US2004/002215, filed on Jan. 26, 2004. (Applicant—University of Utah; Inventor—Cawthon et al.) (1 page).
Supplementary Search Report dated Jun. 19, 2012 for European application No. 04705326.9, which claims priority to PCT/US2004/002215, filed on Jan. 26, 2004. (Applicant—University of Utah; Inventor—Cawthon et al.) (5 pages).
Response to Office Action filed on Jul. 2, 2012 for European application No. 04705326.9, which claims priority to PCT/US2004/002215, filed on Jan. 26, 2004. (Applicant—University of Utah; Inventor—Cawthon et al.) (2 pages).
Intention to Grant dated Sep. 4, 2012 for European application No. 04705326.9, which claims priority to PCT/US2004/002215, filed on Jan. 26, 2004. (Applicant—University of Utah; Inventor—Cawthon et al.) (44 pages).
Decision to Grant dated Jan. 31, 2013 for European application No. 04705326.9, which claims priority to PCT/US2004/002215, filed on Jan. 26, 2004. (Applicant—University of Utah; Inventor—Cawthon et al.) (2 pages).
Certificate of Grant dated Feb. 27, 2013 for European application No. 04705326.9, which claims priority to PCT/US2004/002215, filed on Jan. 26, 2004. (Applicant—University of Utah; Inventor—Cawthon et al.) (1 page).
Office Action dated Feb. 16, 2012 for European application No. 12152681.8, which was filed on Jan. 26, 2012 and published as 2474822 on Jul. 11, 2012 (Applicant—University of Utah; Inventor—Cawthon et al.) (1 page).

(56) References Cited

OTHER PUBLICATIONS

Response to Office Action filed Apr. 26, 2012 for European application No. 12152681.8, which was filed on Jan. 26, 2012 and published as 2474822 on Jul. 11, 2012 (Applicant—University of Utah; Inventor—Cawthon et al.) (1 page).
Office Action dated Apr. 27, 2012 for European application No. 12152681.8, which was filed on Jan. 26, 2012 and published as 2474822 on Jul. 11, 2012 (Applicant—University of Utah; Inventor—Cawthon et al.) (2 pages).
Response to Office Action filed May 14, 2012 for European application No. 12152681.8, which was filed on Jan. 26, 2012 and published as 2474822 on Jul. 11, 2012 (Applicant—University of Utah; Inventor—Cawthon et al.) (1 page).
Supplementary Search Report dated Jun. 8, 2012 for European application No. 12152681.8, which was filed on Jan. 26, 2012 and published as 2474822 on Jul. 11, 2012 (Applicant—University of Utah; Inventor—Cawthon et al.) (11 pages).
Communication pursuant to Rules 70(2) and 70a(2) EPC and reference to Rule 39(1) EPC dated Jul. 16, 2012 for European application No. 12152681.8, which was filed on Jan. 26, 2012 and published as 2474822 on Jul. 11, 2012 (Applicant—University of Utah; Inventor—Cawthon et al.) (2 pages).
Response to Communication pursuant to Rules 70(2) and 70a(2) EPC and reference to Rule 39(1) EPC filed on Apr. 22, 2013 for European application No. 12152681.8, which was filed on Jan. 26, 2012 and published as 2474822 on Jul. 11, 2012 (Applicant—University of Utah; Inventor—Cawthon et al.) (4 pages).
Office Action dated Nov. 4, 2009 for Japanese application No. 2006-503063, which claims priority to PCT/US2004/002215, filed on Jan. 26, 2004. (Applicant—University of Utah; Inventor—Cawthon et al.) (2 pages).
Response to Office Action filed on Mar. 25, 2010 for Japanese application No. 2006-503063, which claims priority to PCT/US2004/002215, filed on Jan. 26, 2004. (Applicant—University of Utah; Inventor—Cawthon et al.) (5 pages).
Office Action dated Nov. 16, 2010 for Japanese application No. 2006-503063, which claims priority to PCT/US2004/002215, filed on Jan. 26, 2004. (Applicant—University of Utah; Inventor—Cawthon et al.) (Original: 3 pages/Translation: 3 pages).
Notice of appeal filed Mar. 16, 2011 for Japanese application No. 2006-503063, which claims priority to PCT/US2004/002215, filed on Jan. 26, 2004. (Applicant—University of Utah; Inventor—Cawthon et al.) (3 pages).
Formality office action dated Apr. 12, 2011 for Japanese application No. 2006-503063, which claims priority to PCT/US2004/002215, filed on Jan. 26, 2004. (Applicant—University of Utah; Inventor—Cawthon et al.) (2 pages).
Appeal brief filed May 24, 2011 for Japanese application No. 2006-503063, which claims priority to PCT/US2004/002215, filed on Jan. 26, 2004. (Applicant—University of Utah; Inventor—Cawthon et al.) (8 pages).
Office Action dated Jan. 21, 2014 for Japanese application No. 2006-503063, which claims priority to PCT/US2004/002215, filed on Jan. 26, 2004. (Applicant—University of Utah; Inventor—Cawthon et al.) (4 pages).
Response to Office Action filed on May 20, 2014 for Japanese application No. 2006-503063, which claims priority to PCT/US2004/002215, filed on Jan. 26, 2004. (Applicant—University of Utah; Inventor—Cawthon et al.) (6 pages).
Office Action dated Sep. 2, 2014 for Japanese application No. 2006-503063, which claims priority to PCT/US2004/002215, filed on Jan. 26, 2004. (Applicant—University of Utah; Inventor—Cawthon et al.) (4 pages).
Response to Office Action filed on Nov. 28, 2014 for Japanese application No. 2006-503063, which claims priority to PCT/US2004/002215, filed on Jan. 26, 2004. (Applicant—University of Utah; Inventor—Cawthon et al.) (2 pages).
Certificate of Patent dated Jan. 30, 2015 for Japanese application No. 2006-503063, which claims priority to PCT/US2004/002215, filed on Jan. 26, 2004. (Applicant—University of Utah; Inventor—Cawthon et al.) (1 page).
International search report dated Nov. 18, 2004 for PCT/US2004/002215, which was filed on Jan. 26, 2004 and published as WO 2004/068110 on Aug. 12, 2004 (Applicant—University of Utah; Inventor—Cawthon et al.) (4 pages).
Written opinion of international search report dated Jul. 24, 2005 for PCT/US2004/002215, which was filed on Jan. 26, 2004 and published as WO 2004/068110 on Aug. 12, 2004 (Applicant—University of Utah; Inventor—Cawthon et al.) (5 pages).
International preliminary report on patentability dated Jul. 29, 2005 for PCT/US2004/002215, which was filed on Jan. 26, 2004 and published as WO 2004/068110 on Aug. 12, 2004 (Applicant—University of Utah; Inventor—Cawthon et al.) (6 pages).
Preliminary Amendment filed on Mar. 10, 2006 for U.S. Appl. No. 10/543,111, filed Mar. 10, 2006, now U.S. Pat. No. 9,169,516 on Oct. 27, 2015 (Applicant—University of Utah; Inventor—Cawthon et al.) (8 pages).
Non-Final Office Action dated Aug. 23, 2007 for U.S. Appl. No. 10/543,111, filed Mar. 10, 2006, now U.S. Pat. No. 9,169,516 on Oct. 27, 2015 (Applicant—University of Utah; Inventor—Cawthon et al.) (14 pages).
Response to Non-Final Office Action filed on Feb. 25, 2008 for U.S. Appl. No. 10/543,111, filed Mar. 10, 2006, now U.S. Pat. No. 9,169,516 on Oct. 27, 2015 (Applicant—University of Utah; Inventor—Cawthon et al.) (8 pages).
Non-Final Office Action dated May 12, 2008 for U.S. Appl. No. 10/543,111, filed Mar. 10, 2006, now U.S. Pat. No. 9,169,516 on Oct. 27, 2015 (Applicant—University of Utah; Inventor—Cawthon et al.) (10 pages).
Response to Non-Final Office Action filed on Nov. 12, 2008 for U.S. Appl. No. 10/543,111, filed Mar. 10, 2006, now U.S. Pat. No. 9,169,516 on Oct. 27, 2015 (Applicant—University of Utah; Inventor—Cawthon et al.) (6 pages).
Final Office Action dated Jan. 27, 2009 for U.S. Appl. No. 10/543,111, filed Mar. 10, 2006, now U.S. Pat. No. 9,169,516 on Oct. 27, 2015 (Applicant—University of Utah; Inventor—Cawthon et al.) (16 pages).
Notice of Appeal filed on Jul. 27, 2009 for U.S. Appl. No. 10/543,111, filed Mar. 10, 2006, now U.S. Pat. No. 9,169,516 on Oct. 27, 2015 (Applicant—University of Utah; Inventor—Cawthon et al.).
Response After Final Office Action filed on Nov. 25, 2009 for U.S. Appl. No. 10/543,111, filed Mar. 10, 2006, now U.S. Pat. No. 9,169,516 on Oct. 27, 2015 (Applicant—University of Utah; Inventor—Cawthon et al.) (13 pages).
Non-Final Office Action dated May 2, 2013 for U.S. Appl. No. 10/543,111, filed Mar. 10, 2006, now U.S. Pat. No. 9,169,516 on Oct. 27, 2015 (Applicant—University of Utah; Inventor—Cawthon et al.) (7 pages).
Response to Non-Final Office Action filed on Nov. 1, 2013 for U.S. Appl. No. 10/543,111, filed Mar. 10, 2006, now U.S. Pat. No. 9,169,516 on Oct. 27, 2015 (Applicant—University of Utah; Inventor—Cawthon et al.) (6 pages).
Final Office Action dated Jan. 10, 2014 for U.S. Appl. No. 10/543,111, filed Mar. 10, 2006, now U.S. Pat. No. 9,169,516 on Oct. 27, 2015 (Applicant—University of Utah; Inventor—Cawthon et al.) (12 pages).
Response to Final Office Action and request for Continued Examination filed on Jul. 10, 2014 for U.S. Appl. No. 10/543,111, filed Mar. 10, 2006, now U.S. Pat. No. 9,169,516 on Oct. 27, 2015 (Applicant—University of Utah; Inventor—Cawthon et al.) (11 pages).
Non-Final Office Action dated Jan. 8, 2015 for U.S. Appl. No. 10/543,111, filed Mar. 10, 2006, now U.S. Pat. No. 9,169,516 on Oct. 27, 2015 (Applicant—University of Utah; Inventor—Cawthon et al.) (10 pages).
Response to Non-Final Office Action filed on May 8, 2015 for U.S. Appl. No. 10/543,111, filed Mar. 10, 2006, now U.S. Pat. No. 9,169,516 on Oct. 27, 2015 (Applicant—University of Utah; Inventor—Cawthon et al.) (12 pages).

(56) References Cited

OTHER PUBLICATIONS

Notice of Allowance dated Jun. 15, 2015 for U.S. Appl. No. 10/543,111, filed Mar. 10, 2006, now U.S. Pat. No. 9,169,516 on Oct. 27, 2015 (Applicant—University of Utah; Inventor—Cawthon et al.) (7 pages).
Issue Notification dated Oct. 27, 2015 for U.S. Appl. No. 10/543,111, filed Mar. 10, 2006, now U.S. Pat. No. 9,169,516 on Oct. 27, 2015 (Applicant—University of Utah; Inventor—Cawthon et al.) (1 page).
Preliminary Amendment filed on Sep. 18, 2015 for U.S. Appl. No. 14/858,177, filed Sep. 18, 2015 (Applicant—University of Utah; Inventor—Cawthon et al.) (3 pages).
International Search Report dated Dec. 30, 2014 by the International Searching Authority for International Patent Application No. PCT/US2014/039110, which was filed on May 22, 2014 and published as WO 2014/190138 on Nov. 27, 2014 (Inventor—Harley; Applicant—Telome Health, Inc.) (6 pages).
Office Action dated Feb. 2, 2015 by the State Intellectual Property Office of the People's republic of China for Chinese Patent Application No. 2012800689920, which was filed on Dec. 28, 2012 and published as CN104105798 on Oct. 15, 2014 (Inventor—Harley; Applicant—Telome Health, Inc.) (4 pages).
Extended European Search Report dated Jul. 10, 2015 by the European Patent Office for European Patent Application No. 12863843.4, which was filed on Dec. 28, 2012 and published as EP 2798091 on Nov. 6, 2014 (Inventor—Harley; Applicant—Telome Health, Inc.) (6 pages).
International Search Report and Written Opinion dated Mar. 11, 2013 by the International Searching Authority for International Patent Application No. PCT/US2012/072131, which was filed on Dec. 28, 2012 and published as WO 2013/102116 on Jul. 4, 2013 (Inventor—Harley; Applicant—Telome Health, Inc.) (12 pages).
International Preliminary Report on Patentability dated Jul. 1, 2014 by the International Searching Authority for International Patent Application No. PCT/US2012/072131, which was filed on Dec. 28, 2012 and published as WO 2013/102116 on Jul. 4, 2013 (Inventor—Harley; Applicant—Telome Health, Inc.) (10 pages).
Preliminary Amendment filed on Jun. 30, 2014 for U.S. Appl. No. 14/370,005, filed Dec. 28, 2012 and published as US 2014/0370505 on Dec. 18, 2014 (Telomere Diagnostics, Inc.; Inventor—Harley) (3 pages).
Preliminary Amendment filed on Nov. 5, 2014 for U.S. Appl. No. 14/370,005, filed Dec. 28, 2012 and published as US 2014/0370505 on Dec. 18, 2014 (Telomere Diagnostics, Inc.; Inventor—Harley) (6 pages).
Restriction Requirement dated Sep. 4, 2015 for U.S. Appl. No. 14/370,005, filed Dec. 28, 2012 and published as US 2014/0370505 on Dec. 18, 2014 (Telomere Diagnostics, Inc.; Inventor—Harley) (9 pages).
Response to Restriction Requirement filed on Oct. 20, 2015 for U.S. Appl. No. 14/370,005, filed Dec. 28, 2012 and published as US 2014/0370505 on Dec. 18, 2014 (Telomere Diagnostics, Inc.; Inventor—Harley) (9 pages).
Non-Final Office Action dated Nov. 19, 2015 for for U.S. Appl. No. 14/370,005, filed Dec. 28, 2012 and published as US 2014/0370505 on Dec. 18, 2014 (Telomere Diagnostics, Inc.; Inventor—Harley) (11 pages).
Office Action dated Nov. 18, 2016 by the Canadian Intellectual Property Office for Canadian Patent Application No. 2,748,265, which was filed on Jun. 22, 2011 (Applicant—University of Utah; Inventor—Cawthon et al.) (3 pages).
Third Office Action dated Aug. 30, 2016 by the State Intellectual Property Office of the People's Republic of China for Chinese Patent Application No. 2009801572698, which was filed on Aug. 22, 2011 and published as CN102439171 on May 2, 2012 (Applicant—University of Utah; Inventor—Cawthon et al.) (4 pages).
Notice of Grant and Notice of Registration dated Apr. 6, 2017 by the State Intellectual Property Office of the People's Republic of China for Chinese Patent Application No. 2009801572698, which was filed on Aug. 22, 2011 and published as CN102439171 on May 2, 2012 (Applicant—University of Utah; Inventor—Cawthon et al.) (3 pages).
Office Action dated Jun. 28, 2016 by the Japan Patent Office for Japanese Patent Application No. 2015-175632, which was filed on Dec. 22, 2009 and published on Dec. 10, 2015 (Applicant—University of Utah; Inventor—Cawthon et al.) (2 pages).
Penultimate Rejection dated Apr. 14, 2017 by the Japan Patent Office for Japanese Patent Application No. 2015-175632, which was filed on Dec. 22, 2009 and published on Dec. 10, 2015 (Applicant—University of Utah; Inventor—Cawthon et al.) (2 pages).
Notice of Allowance dated Dec. 11, 2015 by the U.S. Patent and Trademark Office for U.S. Appl. No. 13/141,429, filed Aug. 15, 2011 and published as US 2011/0294676 on Dec. 1, 2011 (Applicant—University of Utah; Inventor—Cawthon et al.) (16 pages).
Non-Final Office Action dated Apr. 22, 2016 by the U.S. Patent and Trademark Office for U.S. Appl. No. 13/141,429, filed Aug. 15, 2011 and published as US 2011/0294676 on Dec. 1, 2011(Applicant—University of Utah; Inventor—Cawthon et al.) (12 pages).
Response to Non-Final Office Action filed on Oct. 12, 2016 with the U.S. Patent and Trademark Office for U.S. Appl. No. 13/141,429, filed Aug. 15, 2011 and published as US 2011/0294676 on Dec. 1, 2011(Applicant—University of Utah; Inventor—Cawthon et al.) (10 pages).
Final Office Action dated Jan. 25, 2017 by the U.S. Patent and Trademark Office for U.S. Appl. No. 13/141,429, which was filed on Aug. 15, 2011 and published as US 2011/0294676 on Dec. 1, 2011 (Applicant—University of Utah; Inventor—Cawthon et al.) (9 pages).
Response After Final Office Action filed on Mar. 10, 2017 with the U.S. Patent and Trademark Office for U.S. Appl. No. 13/141,429, filed Aug. 15, 2011 and published as US 2011/0294676 on Dec. 1, 2011(Applicant—University of Utah; Inventor—Cawthon et al.) (14 pages).
Notice of Allowance dated Mar. 30, 2017 by the U.S. Patent and Trademark Office for U.S. Appl. No. 13/141,429, filed Aug. 15, 2011 and published as US 2011/0294676 on Dec. 1, 2011(Applicant—University of Utah; Inventor—Cawthon et al.) (15 pages).
Notice of Allowance dated Apr. 25, 2017 by the U.S. Patent and Trademark Office for U.S. Appl. No. 13/141,429, filed Aug. 15, 2011 and published as US 2011/0294676 on Dec. 1, 2011(Applicant—University of Utah; Inventor—Cawthon et al.) (6 pages).
Notice of Allowance dated May 26, 2017 by the U.S. Patent and Trademark Office for U.S. Appl. No. 13/141,429, filed Aug. 15, 2011 and published as US 2011/0294676 on Dec. 1, 2011(Applicant—University of Utah; Inventor—Cawthon et al.) (6 pages).
Issue Notification dated Jun. 7, 2017 by the U.S. Patent and Trademark Office for U.S. Appl. No. 13/141,429, filed Aug. 15, 2011 and published as US 2011/0294676 on Dec. 1, 2011(Applicant—University of Utah; Inventor—Cawthon et al.) (1 page).
Notice of Allowance dated Dec. 1, 2016 for Canadian Patent application No. 2,513,747, which claims priority to PCT/US2004/002215, filed on Jan. 26, 2004 (Applicant—University of Utah; Inventor—Cawthon et al.) (1 page).
Certificate of Patent dated Mar. 7, 2017 for Canadian Patent application No. 2,513,747, which claims priority to PCT/US2004/002215, filed on Jan. 26, 2004 (Applicant—University of Utah; Inventor—Cawthon et al.) (1 page).
Communication Pursuant to 94(3) EPC dated Nov. 17, 2016 for European Patent application No. 12152681.8, which was filed on Jan. 26, 2012 and published as 2474822 on Jul. 11, 2012 (Applicant—University of Utah; Inventor—Cawthon et al.) (5 pages).
Restriction Requirement dated Jan. 24, 2013 for U.S. Appl. No. 13/028,910, filed Feb. 16, 2011 and published as US 2011/0207128 on Aug. 25, 2011 (Applicant—University of Utah; Inventor—Cawthon et al.) (8 pages).
Notice of Abandonment dated Aug. 7, 2013 for U.S. Appl. No. 13/028,910, filed Feb. 16, 2011 and published as US 2011/0207128 on Aug. 25, 2011 (Applicant—University of Utah; Inventor—Cawthon et al.) (2 pages).
Third Office Action dated Mar. 18, 2016 by the State Intellectual Property Office of the People's Republic of China for Chinese Patent Application No. 201280068992.0, which was filed on Dec. 28, 2012 and published as 104105798 on Oct. 15, 2014 (Inventor—Harley; Applicant—Telome Health, Inc.) (Original—3 pages/ Translation—6 pages).

(56) References Cited

OTHER PUBLICATIONS

Fourth Office Action dated Sep. 27, 2016 by the State Intellectual Property Office of the People's Republic of China for Chinese Patent Application No. 201280068992.0, which was filed on Dec. 28, 2012 and published as 104105798 on Oct. 15, 2014 (Inventor—Harley; Applicant—Telome Health, Inc.) (Original—4 pages/ Translation—6 pages).

Office Action and Search Report dated Jul. 29, 2016 by the Intellectual Property Office of Taiwan for Taiwanese Patent Application No. 101151332, which was filed on Dec. 28, 2012 and published as 201343919 on Nov. 1, 2013 (Inventor—Harley; Applicant—Telome Health, Inc.) (Original—3 pages/ Translation—6 pages).

Response to Non-Final Office Action filed on May 18, 2016 with the U.S. Patent and Trademark Office for U.S. Appl. No. 14/370,005, filed Dec. 28, 2012 and published as US 2014/0370505 on Dec. 18, 2014 (Telomere Diagnostics, Inc.; Inventor—Harley) (15 pages).

Final Office Action dated Jul. 12, 2016 by the U.S. Patent and Trademark Office for U.S. Appl. No. 14/370,005, filed Dec. 28, 2012 and published as US 2014/0370505 on Dec. 18, 2014 (Telomere Diagnostics, Inc.; Inventor—Harley) (8 pages).

Notice of Abandonment dated Jan. 26, 2017 by the U.S. Patent and Trademark Office for U.S. Appl. No. 14/370,005, filed Dec. 28, 2012 and published as US 2014/0370505 on Dec. 18, 2014 (Telomere Diagnostics, Inc.; Inventor—Harley) (2 pages).

Preliminary Amendment filed on Oct. 6, 2016 with the U.S. Patent and Trademark Office for U.S. Appl. No. 15/287,099, filed Oct. 6, 2016 and published as US 2017/0023451 on Jan. 26, 2017 (Inventor—Harley et al.; Applicant—Telomere Diagnostics, Inc.) (6 pages).

Restriction Requirement dated Feb. 1, 2017 by the U.S. Patent and Trademark Office for U.S. Appl. No. 14/746,437, filed Jun. 22, 2015 and published as US 2016/0186250 on Jun. 30, 2016 (Inventor—Harley et al.; Applicant—Telomere Diagnostics, Inc.) (7 pages).

Response to Restriction Requirement filed on May 11, 2017 with the U.S. Patent and Trademark Office for U.S. Appl. No. 14/746,437, filed Jun. 22, 2015 and published as US 2016/0186250 on Jun. 30, 2016 (Inventor—Harley et al.; Applicant—Telomere Diagnostics, Inc.) (8 pages).

Communication Pursuant to Article 94(3) EPC dated Sep. 20, 2018 by the European Patent Office for EP Application No. 14800611.7, filed on May 22, 2014 and published as EP 2999800 on Mar. 30, 2016 (Applicant—Telomere Diagnostics, Inc.) (4 Pages).

Wang, et al.: "The role of telomeres and telomerase in hematologic malignancies and hematopoietic stem cell transplantation", Journal of Hematology & Oncology, vol. 7, No. 1, p. 61 (2014).

Final Rejection dated Apr. 19, 2018 by the USPTO for U.S. Appl. No. 14/858,177, filed Sep. 18, 2015, and published as US 2016/0194705 A1 on Jul. 7, 2016 (Inventor—Richard Cawthon ) (6 pages).

European Search Report dated May 8, 2018 by the European Patent Office for EP Application No. 15875839.1, filed Jun. 22, 2015 and published as EP 3240910, filed Nov. 8, 2017 (Applicant—Telomere Diagnostics, Inc.) (8 pages).

European Search Report dated May 23, 2018 by the European Patent Office for EP Application No. 17202134.7, filed Jan. 26, 2004 (Applicant—University of Utah) (9 pages).

Notice of Rejection dated Jun. 12, 2018 by the Japanese Patent Office for JP Application No. 2016-515077, filed May 22, 2014, and published as JP 2016521548A on Jul. 25, 2016 (Applicant—Telomere Diagnostics Inc.) (Original—3 pages// Translation—3 pages).

Office Action dated Sep. 27, 2018 by the Mexican Patent Office for MX Application No. MX/a/2015/015891, filed on May 22, 2014 and published as MX 2015015891 A on Jun. 2, 2016 (Applicant—Telomere Diagnostics, Inc.) (6 pages).

\* cited by examiner

FIG. 5

| percentage of short telomeres | UMUC3 | UMUC3/hTER |
|---|---|---|
| Southern blot (0.2-5Kb) | 75% | 26% |
| short telomere assay | 100% | 33% |

FIG. 6

| STEP | DESCRIPTION | AUTOMATION OR MANUAL |
|---|---|---|
| Annealing | 1.1. pipette gDNA and mix with TeloPrimer and water | Automated |
| | 1.2. incubate at 65 °C for 10 min, cool down slowly | |
| | | |
| Strand displacement | 2.1. pipette master mix with Sequenase 2.0/SSB/buffer | Automated |
| | 2.2. pipette gDNA and mix | Automated |
| | 2.3. seal plate | Manual |
| | 2.4. incubate at 37 °C for 3 minutes | Manual |
| | 2.5. transfer plate to 80 °C for 20 minutes | Manual |
| | | |
| PCR with SUS and TELOANCHOR | 3.1. Dilute samples from step 2.5 with low EDTA Tris | Automated |
| | 3.2. pipette PCR master mix into a new 96 well plate | Automated |
| | 3.3. pipette diluted DNA from step 3.1 to 96 well plate from step 3.2 | Automated |
| | 3.4. seal both plate | Manual |
| | 3.5. transfer the PCR plate to Thermocycler | Manual |
| | 3.6. PCR | |
| | | |
| TELOTEST | 4.1. Dilute PCR products from step 3.6 with low EDTA Tris | Automated |
| | 4.2. Perform the T-run of TeloTest® with diluted samples from 4.1. | Automated |

MEASURES OF SHORT TELOMERE ABUNDANCE

CROSS-REFERENCE TO RELATED APPLICATIONS

This Application claims the benefit of U.S. Provisional Application No. 61/826,484, filed on May 22, 2013, which is incorporated herein by reference in its entirety.

BACKGROUND OF THE INVENTION

The statements in the Background are not necessarily meant to endorse the characterization in the cited references.

Telomeres, the tips of eukaryotic chromosomes, protect the chromosomes from nucleolytic degradation, end-to-end fusion, and recombination. Telomeres are structures at the ends of chromosomes characterized by repeats of the nucleotide sequence $(5'-TTAGGG-3')_n$. Telomeres shorten as a consequence of normal cell division and critically short telomeres lead to cellular senescence or apoptosis. A rich body of epidemiological and clinical studies in humans in the past decade has linked short telomere length to high risks of aging-related disease and all-cause mortality (Puterman, E. and E. Epel, Soc Personal Psychol Compass, 2012. 6(11) 807-825; Zhu, H., M. Belcher, and P. van der Harst, Clin Sci (Lond), 2011. 120(10) 427-40; and Fyhrquist, F. and O. Saijonmaa. Ann Med, 2012. 44 Suppl 1 S138-42). Genetic, environment, lifestyle, and behavioral factors collectively impact telomere length. Therefore, telomere length has become an index for overall health, disease, and mortality risk.

While average telomere length was measured in almost all the clinical studies published and has demonstrated utility in stratifying patient disease and mortality risk, recent work in mice has also shown that the population of short telomeres is the triggering signal to senescence or apoptosis (Hemann, M. T., et al. Cell, 2001. 107(1) 67-77), and thus disease and mortality risk. In a study reported by Hemann et al, 6th generation telomerase RNA knockout mice (mTR−/−G6) with short telomeres were crossed with mice heterozygous for telomerase (mTR+/−) with long telomeres. The phenotype of the telomerase null offspring mirrors that of the mTR−/− parent despite the fact that half of their telomeres are long, suggesting that the quantity of short telomeres, and not average telomere length, is critical for cell viability and chromosome stability. In people taking a natural product-derived telomerase activator (TA-65®), a significant reduction in the percentage of short (<3 or <4 kbp) telomeres (as measured by a quantitative FISH technology; see (Canela, A., et al. Proc Natl Acad Sci USA, 2007. 104(13) 5300-5) was detected in the leukocytes, although no change in mean telomere length was seen (Harley, C. B., et al., Rejuvenation Res. 2011. 14(1) 45-56). Changes in the percentage of short telomere abundance therefore is expected to be a more sensitive measurement of the effects of lifestyle and pharmacological or other interventions on telomeres. Another study (Vera et al., "The Rate of Increase of Short Telomeres Predicts Longevity in Mammals", Cell Reports (2012), world wide web URL: dx.doi.org/10.1016/j.celrep.2012.08.023) found that "the rate of increase in the abundance of short telomeres was a predictor of lifespan".

Various methods have been developed for the measurement of telomere length in genomic DNA, including Southern blotting (Kimura, M. et al., Nature Protocols, 2010, 5:1596-1607), Q-FISH (Rufer, N. et al., Nat. Biotechnol., 1998, 16:743-747), flow FISH (Baerlocher, G. M. et al., Cytometry, 2002, 47:89-99), and qPCR (Cawthon, R. M., Nucleic. Acids Res., 2002, 30(10):e47). All of these methods can be used in a clinical setting to monitor health status and permit physicians to prescribe prophylactic or therapeutic intervention tailored to the needs of the individual patient.

To measure the population of short telomeres, quantitative fluorescent in situ hybridization (Q-FISH) of metaphase-spread cells has been used to generate histograms of telomere signal intensities which represent the length of individual telomeres (Poon, S. S., et al., Cytometry, 1999. 36(4) 267-78). Limitations of this method are that live cells are needed, costs are high, and throughput is low. A higher throughput modification of the Q-FISH assay (HTQ-FISH; see Canela, A., et al. Proc Natl Acad Sci USA, 2007. 104(13) 5300-5) was recently championed by the company Life Length (Spain) to measure percentage of short telomeres. Despite the claim, unfortunately, with current technology, this assay cannot be accurate, due to clustering of telomeres, especially short telomeres, in single spots (telomeric associations; see Paeschke, K., K. R. McDonald, and V. A. Zakian. FEBS Lett, 2010. 584(17) 3760-72). Confounding this issue is the fact that short telomeres tend to associate with one another more frequently than long telomeres. In addition, FISH technologies are known to suffer from non-specific binding of the probe to macromolecules in live or fixed cells. A high throughput method to measure percentage of short telomeres that is low-cost and does not require live cells will be much easier to be adapted in both epidemiological and clinical settings, and will have better analytical performance than Q-FISH.

U.S. Pat. No. 5,741,677 (Kozlowski et al.) refers to methods for measuring telomere length. One method involves contacting the telomere with a linker sequence under conditions in which the linker sequence is ligated or otherwise covalently bonded to the 3' end of the telomere. The telomere sequences are amplified by long PCR amplification with a first primer specific for the linker sequence and a second primer specific for a subtelomeric region of the chromosome. Another method involves preparing DNA extracts of cells, incubating the extract with an oligonucleotide probe complementary to a telomere repeat sequence, and determining amount of probe bound as a measure of telomere length. In addition, a method of measuring telomere length by binding the genomic DNA to a solid phase, and hybridizing the bound DNA with a labeled probe is described.

U.S. Patent Publication No. 2004/0265815 (Baird et al.) refers to a method for measuring telomere length. Baird et al. describes the following steps to detect the length of a population of telomeres: a) annealing the 3' end of a single-stranded oligonucleotide (hereinafter referred to as a telorette) to a single-stranded overhang of the telomere comprising the G-rich telomere strand (comprising TTAGGG repeat sequences) and covalently binding the telorette to the 5' end of the C-rich telomeric strand (having CCCTAA repeat sequences), b) amplifying the ligation product formed in step (a) to form a primer extension product; and (c) detecting the length of the primer extension product(s) of step (b). (See also Baird, D. M., et al., Nat Genet., 2003, 33(2):203-7; and Baird D M, Rowson J, Wynford-Thomas D, Kipling D.; Nat Genet., 2003, 33(2):203-7. Epub 2003 Jan. 21. PMID: 12539050)

U.S. Pat. No. 6,514,693 (Lansdorp) refers to a method for detecting multiple copies of a repeat sequence in a nucleic acid molecule in morphologically intact chromosomes, cells, or tissue sections comprising: (a) treating the nucleic acid molecule with a PNA probe which hybridizes to a repeat sequence in the nucleic acid molecule and which is labeled with a detectable substance, under denaturing conditions utilizing a denaturing agent, permitting the probe to hybridize in situ to the repeat sequence in the nucleic acid molecule; and (b) identifying said probe hybridized to the repeat sequence in the nucleic acid molecule by directly or indirectly detecting the detectable substance, thereby detecting the multiple copies of a repeat sequence in a nucleic acid molecule.

Methods of determining short telomere abundance include Southern blot analysis, quantitative fluorescence in situ hybridization (Q-FISH) (Poon, S. S., et al., *Cytometry*, 1999, 36(4):267-78) and a modified high throughput version of Q-FISH (HT-Q-FISH) (Canela, A., et al., *Proc. Natl. Acad. Sci. USA*, 2007, 104(13):5300-5).

U.S. Pat. No. 7,695,904 (Cawthon) describes methods for amplifying target nucleic acids using nucleic acid primers designed to limit non-target nucleic acid dependent priming events. The methods permit amplifying and quantitating the number of repetitive units in a repetitive region, such as the number of telomere repetitive units. The patent also refers to determining average telomere length of an organism by qPCR method.

Thus, despite advances in materials and methods pertaining to telomeres, there remains a need for improved methods and materials for determining measures of short telomere abundance in a population of chromosomes and the use of these measures to determine measures of health and effects of interventions that increase or decrease telomere length and, hence, increase or decrease health, or conversely decrease or increase risk of future disease or death, respectively. These needs and other needs are addressed by the present invention.

SUMMARY OF THE INVENTION

In one aspect, this invention provides a method of making a nucleic acid extension product comprising: i) hybridizing an extension primer to a telomeric repeat sequence in a 3' overhang of double stranded chromosomal DNA, wherein: (1) the double stranded chromosomal DNA has a telomeric region comprising telomeric repeat sequences and a sub-telomeric region comprising sub-telomeric sequences; and (2) the extension primer comprises: (A) a 3' portion that hybridizes to a telomeric repeat sequence in the 3' overhang under annealing conditions, and (B) a 5' portion having an anchor sequence that does not hybridize to a telomeric repeat sequence in the 3' overhang under the annealing conditions; and ii) performing a time-limited extension reaction to extend the extension primer towards the sub-telomeric region of the double stranded chromosomal DNA, wherein the extension reaction is timed to produce an extension product comprising both telomeric repeat sequences and sub-telomeric sequences only from double stranded chromosomal DNA having a telomeric region within a pre-determined length range. In one aspect the double-stranded chromosomal DNA comprises chromosomes molecules having telomeres of different lengths. In a further aspect, the anchor sequence does not hybridize under the annealing conditions to: (1) a sequence in the sub-telomeric region of the strand of chromosomal DNA having the 3' overhang; (2) a sequence in the G-strand of the chromosomal DNA within 20 kb of the 3' overhang; (3) a sequence in the G-strand of the chromosomal DNA within 50 kb or within 20 kb of the 3' overhang; or (4) a sequence in the double stranded chromosomal DNA. In a further aspect, the extension reaction is timed to no more than 30 minutes, no more than 10 minutes, no more than 5 minutes, no more than 4 minutes, no more than 3 minutes, no more than 2 minutes, no more than 1 minute, no more than 30 seconds, no more than 20 sec, no more than 10 sec, no more than 5 sec, or no more than 2 sec. Since the rate to primer extension can range from high (400 nucleotides per sec) to very low (e.g. 50 nucleotides per second), a broad range of extension time allows assessment of a broad range of telomere lengths (theoretically from about 100 nucleotides, to many thousands of nucleotides. In a further aspect, the extension reaction is timed to at least 30 minutes, at least 10 minutes, at least 5 minutes, at least 4 minutes, at least 3 minutes, at least 2 minutes, at least 1 minute or at least 30 seconds. In a further aspect, the extension reaction is timed to at least 30 minutes, at least 10 minutes, at least 5 minutes, at least 4 minutes, at least 3 minutes, at least 2 minutes, at least 1 minute or at least 30 seconds. In a further aspect, the double-stranded chromosomal DNA is provided from a solid, fluid, semisolid or gaseous sample. In a further aspect, the chromosomal DNA is provided from a liquid sample selected from blood, saliva, urine, plasma, serum, cerebrospinal fluid ("CSF") or bronchoalveolar lavage fluid. In a further aspect, the chromosomal DNA is provided from a solid sample selected from lung, muscle or skin. In a further aspect, the chromosomal DNA is provided from a semi-solid sample comprising bone marrow. In a further aspect, the chromosomal DNA is provided from a gaseous sample comprising breath. In a further aspect, the double-stranded chromosomal DNA is vertebrate DNA, mammalian DNA or human DNA. In a further aspect, the 3' portion of the extension primer hybridizes to a human telomeric repeat sequence. In a further aspect, the 3' portion of the extension primer comprises the sequence 5'-(CCCTAA)n-3' or its same order permutations, wherein n is at least 1. In a further aspect, n is at least 2. In a further aspect, the 5' portion of the extension primer comprises the sequence: 5'-TGCTCGGC-CGATCTGGCATC-3' [SEQ ID NO:8]. In a further aspect, the extension primer comprises the sequence: 5'-TGCTCG-GCCGATCTGGCATCCCTAACC-3' [SEQ ID NO: 7]. In a further aspect, the time-limited extension reaction employs a DNA polymerase possessing strand-displacement activity, exonuclease activity or strand degradation activity. In a further aspect, the DNA polymerase is selected from T7 polymerase (e.g., Sequenase), exonuclease-deficient Klenow fragment of *E. coli* DNA polymerase I, and Bst polymerase large fragment and Deep VentR (exo-nuclease). In a further aspect, the first reaction is performed with a helicase, in combination with a DNA polymerase, or a DNA polymerase with 5'-3' exonuclease activity.

In another aspect, this invention provides a method of amplifying telomeric repeat sequences and sub-telomeric sequences of a chromosome comprising: a) making a nucleic acid extension product by: i) hybridizing an extension primer to a telomeric repeat sequence in a 3' overhang of double stranded chromosomal DNA, wherein: (1) the double stranded chromosomal DNA has a telomeric region comprising telomeric repeat sequences and a sub-telomeric region comprising sub-telomeric sequences; and (2) the extension primer comprises: (A) a 3' portion that hybridizes to a telomeric repeat sequence in the 3' overhang under annealing conditions, and (B) a 5' portion having an anchor sequence that does not hybridize to a telomeric repeat sequence in the 3' overhang under the annealing conditions; and ii) performing a time-limited extension reaction to extend the extension primer towards the sub-telomeric region of the double stranded chromosomal DNA, wherein the extension reaction is timed to produce an extension product comprising both telomeric repeat sequences and sub-telomeric sequences only from double stranded chromosomal DNA having a telomeric region within a predetermined length range; and b) amplifying sequences of the extension product that are bounded by a sub-telomeric sequence and the anchor sequence; thereby producing a length-limited amplification product comprising nucleic acids having telomeric repeat sequences and sub-telomeric sequences. In one aspect the sequences are amplified using: (1) a first amplification primer that hybridizes to a sequence unique to the sub-telomeric region in the extension product under annealing conditions; and (2) a second amplification primer that hybridizes to the anchor sequence under the annealing conditions. In a further aspect, the first amplification primer comprises a sequence selected from: 5'-GATGGATCCTGAGGGTGAGGGTGAGGG-3' [SEQ ID NO: 2], 5'-CGGGCCGGCTGAGGGTACCGCGA-3' [SEQ ID NO: 10] (chromosome 1), 5'-GCTAATGCACTC-CCTCAATAC-3' [SEQ ID NO: 11] (chromosome 5) and 5'-CATTCCTAATGCACACATGATACC-3' [SEQ ID NO: 12] (chromosome 9). In a further aspect, the first amplification primer comprises the sequence 5'-GATGGATCCT-GAGGGTGAGGGTGAGGG-3' [SEQ ID NO: 2] and the second primer comprises the sequence 5'-TGCTCGGC-CGATCTGGCATC-3' [SEQ ID NO: 8]. The length range of the amplified telomere products can be determined by using a time-limited extension time in the PCR reaction. In a further aspect, the method further comprising in co-amplifying a control sequence. In a further aspect, the control sequence comprises a plurality of non-telomeric repeat sequences. In a further aspect, the control sequence is synthesized in vitro or produced in vivo (e.g., in a bacterial or fungal clone).

In another aspect, this invention provides a method for determining of short telomere abundance comprising: a) providing a sample comprising double-stranded chromosomal DNA comprising a 3' overhang from a subject; b) producing a length-limited amplification product from the double-stranded chromosomal DNA using a method of amplifying telomeric repeat sequences and sub-telomeric sequences of a chromosome of this invention as described herein (e.g., above); and c) determining of short telomere abundance from the length-limited amplified product. In one aspect the method further comprises: d) comparing short telomere abundance with total telomere abundance from the sample. In a further aspect, short telomeres are telomeres having length no more than about than about 0.5 kb, than about 1 kb, than about 2 kb, than about 3 kb, than about 4 kb or than about 5 kb. In a further aspect, comparing comprises determining short telomere abundance as a function of total telomere abundance, e.g., a ratio of short telomere abundance to total telomere abundance. In a further aspect, determining of short telomere abundance is performed using qPCR. In a further aspect, qPCR is performed using a first and a second primer, (i) wherein said first primer hybridizes to at least one repetitive unit of said first strand and said second primer hybridizes to at least one repetitive unit of said second strand, (ii) wherein said hybridized primers are capable of primer extension when hybridized to their respective strands, and wherein at least one nucleotide of said first primer produces an internal base pair mismatch between said first primer and a nucleotide of said repetitive unit when said first primer is hybridized to at least one repetitive unit of said first strand, (iii) wherein said first primer also produces a mismatch with the 3' terminal nucleotide of said second primer when first and second primers hybridize to each other, (iv) wherein at least one nucleotide of said second primer produces an internal base pair mismatch between said second primer and a nucleotide of said repetitive unit when said second primer is hybridized to at least one repetitive unit of said second strand. In a further aspect, determining of short telomere abundance comprises measuring average telomere length in the sample by Southern blot, dot blot, slot blot, immunochemistry, nucleic acid sequencing or digital PCR. In a further aspect, the short telomere abundance is a measure of relative abundance. In a further aspect, the total telomere abundance is measured relative to abundance of a genomic reference sequence. In a further aspect, the genomic reference sequence comprises a single copy reference nucleotide sequence (e.g., human beta-globin) or abundance of non-telomere repetitive DNA (e.g., Alu repeats or centromeric repeats).

In another aspect, this invention provides a method comprising: a) determining of short telomere abundance in a sample from a subject; and b) correlating the short telomere abundance with a condition or disease. In one aspect the measure of short telomere abundance is determined by comparing the short telomere abundance with total telomere abundance from the sample. In a further aspect, the short telomere abundance is determined using a method described herein (e.g., above). In a further aspect, the condition or disease is mortality risk. In a further aspect, the telomere abundance is absolute abundance. In a further aspect, absolute abundance is measured as length of telomeric sequences. In a further aspect, the determining of telomere abundance comprises measuring average telomere length in the sample by qPCR Southern blot, dot blot, slot blot, immunochemistry, nucleic acid sequencing and digital PCR. In a further aspect, the correlation of the condition or disease is associated with the Health Status Survey Score of Perceived Stress (see, for example, Cohen, S; Kamarck T, and Mermelstein R (1983) J. Health Social Behav. 24(4) 385-396). In a further aspect, the risk of a pathological condition is a risk of disease, e.g., cardiovascular disease, diabetes, cancer, liver fibrosis, and depression. In a further aspect, the disease is a disease of aging. In a further aspect, the disease of aging is cardiovascular disease and wherein a measure lower than average in a population correlates with increased risk of cardiovascular disease. In a further aspect, the method comprises correlating a measure of telomere abundance in the lowest two or three tertiles of a population with significantly higher risk for cardiovascular disease compared with a measure in a top tertile of the population. In a further aspect, the method comprises correlating the measure with a telomeric disease. A telomeric disease can include, but is not limited to dyskeratosis congenita, pulmonary fibrosis, aplastic anemia and interstitial pneumonia. In a further aspect, the method comprises the measure with drug responsiveness. For example, the method can comprise the measure with drug responsiveness to a statin (wherein short average telomere length in an individual's normal white blood cells is positively correlated with drug responsiveness) or adverse response to imetelstat (GRN163L, a cancer drug) (wherein short telomere length in normal white blood cells is correlated with adverse effects such as thrombocytopenia or neutropenia). In a further aspect, the method comprises correlating the measure with disease progression and treatment outcome in chronic infections, such as HIV, HCV HBV, and CMV. In a further aspect, the method further comprises reporting the correlation to the subject. In a further aspect, the method further comprises providing the subject with a diagnosis or a prognosis based on the correlation. In a further aspect, the method further comprises treating the subject based on the correlation.

In another aspect, this invention provides a method for monitoring the status of a subject comprising: determining measures of short telomere abundance from cells in each of a plurality of subject samples taken over a period of time; determining differences in the measures; and correlating the differences with progression of a telomeric disease, wherein decreases in the measures indicates progression of the disease. In one aspect the measure of short telomere abundance is determined by comparing the measure of short telomere abundance with a measure of total telomere abundance from the sample.

In another aspect, this invention provides a method comprising: determining a rate of change in a measure of short telomere abundance in cells from a plurality of subject samples, each sample taken at different times; and correlating the rate of change with: (1) a measure of health; (2) a risk of a pathological condition; (3) a telomeric disease or (4) drug responsiveness. In one aspect the measure of short telomere abundance is determined by comparing the measure of short telomere abundance with a measure of total telomere abundance from the sample.

In another aspect, this invention provides a kit comprising: (1) a first amplification primer comprising: (A) a 3' portion that hybridizes to a telomeric repeat sequence in a 3' overhang of double-stranded chromosomal DNA under annealing conditions, and (B) a 5' portion having an anchor sequence that does not hybridize under the annealing conditions to a sequence in the telomeric region or to a sequence in the sub-telomeric region in the chromosomal DNA; and (2) a second amplification primer that hybridizes to a sub-telomeric sequence under annealing conditions. In one aspect the kit further comprises: (3) a third amplification primer that hybridizes to a complement of the anchor sequence under annealing conditions. In a further aspect, the kit comprises: (3) reagents to carry out the hybridization, extension, amplification and quantification steps of the short telomere measurement. In a further aspect, the kit further comprises: (3) a control sample and a reference sample comprising chromosomal DNA with known telomere lengths, or synthetic oligonucleotides with telomeric repeats with known amount of mass.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 5 is a table that compares the relative abundance of short telomeres in UM-UC3 and UM-UC3/hTER by Southern Blot (where the relative signal of terminal restriction fragments in the 0.2-5 kbp range is shown), and by a short telomere assay of this invention, wherein the percentage of short telomeres is the ratio of short and total telomere measurements. In both cases, there are roughly 3-fold more short telomeres in UM-UC3 than in UM-UC3/hTER.

FIG. 6 shows high-throughput steps for a short telomere assay.

FIG. 7B shows second strand synthesis of the three primer extension products. In FIG. 7A, the time for primer extension is selected so that the primer extends past the subtelomeric region (having a subtelomeric unique sequence "SUS") in chromosomes A and B, but not C. In FIG. 7B, a primer "SUS" having a subtelomeric unique sequence can hybridize to extension products A and B, but not to extension product C, which, due to long telomere length in the original chromosome, did not extend into the subtelomeric region. Thus, second strand synthesis can proceed from the SUS primer hybridized to extension products A and B, but not from C. The second strand is represented by the solid line. This product, then, represents a "short telomere" fraction of the original chromosomal DNA.

DETAILED DESCRIPTION OF THE INVENTION

Definitions

Figure 1:
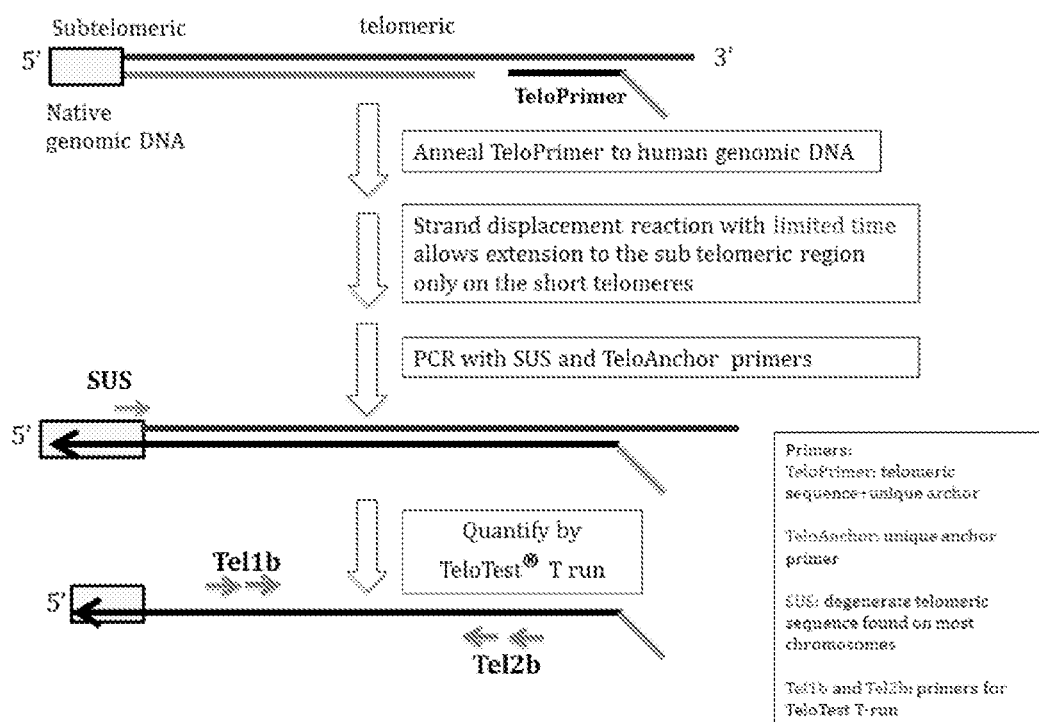
FIG. 1 shows overall scheme of a short telomere assay (STA).

It is to be understood that the terminology used herein is for the purpose of describing particular aspects only and is not intended to be limiting.

As used in the specification and in the claims, the term "comprising" can include the aspects "consisting of" and "consisting essentially of."

As used herein, nomenclature for compounds, including organic compounds, can be given using common names, IUPAC, IUBMB, or CAS recommendations for nomenclature. Unless defined otherwise, all technical and scientific terms used herein have the same meaning as commonly understood by one of ordinary skill in the art to which this invention belongs. In this specification and in the claims which follow, reference will be made to a number of terms which shall be defined herein.

As used in the specification and the appended claims, the singular forms "a," "an" and "the" include plural referents unless the context clearly dictates otherwise. Thus, for example, reference to "a cell," "a nucleotide," or "a primer" includes mixtures of two or more such cells, nucleotides, or primers, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "effective amount" refers to an amount that is sufficient to achieve the desired modification of a physical, chemical, or biological property of the composition or method.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal A patient refers to a subject afflicted with a condition, disease or disorder. The term "patient" includes human and veterinary subjects. In some aspects of the disclosed methods, the subject has been diagnosed with a need for treatment of one or more conditions or diseases associated with a dysfunction in short telomere abundance.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "extension primer" means an oligonucleotide primer used to perform the time-limited extension reaction step carried out by a DNA polymerase. The extension primer can comprises a 3' portion and a 5' portion. For example, the 3' portion can hybridize to a telomeric repeat sequence in the 3' overhang under annealing conditions, and a 5' portion can have an anchor sequence that does not hybridize to a telomeric repeat sequence in the 3' overhang under the annealing conditions.

As used herein, "telomeric region" means the DNA segment at the ends of a chromosome with repeat telomeric sequence. In the case of vertebrates, it can be the (TTAGGG)n repeat sequence at the ends of chromosomes.

As used herein, "sub-telomeric region" means the segment of DNA immediately adjacent to telomere at the centromeric end of telomeres. Subtelomeric region often contains degenerate telomeric repeats. In the case of humans, repeats of TGAGGG and TCAGGG can be present in subtelomeric region.

As used herein, "time-limited extension reaction" means an enzymatic reaction carried out by a DNA polymerase wherein the size of the product of the reaction, the time-limited extension product, in nucleotides is a function of both the intrinsic extension rate of the DNA polymerase utilized in the reaction and the reaction time.

As used herein, "anchor sequence" means a unique sequence segment within a primer that is not present in the template genome that can be used in the PCR reaction or present within 20 kb of the intended amplicon. For example, the 5' portion of an extension primer can be an anchor sequence that is configured not to hybridize under annealing conditions to a telomeric repeat sequence in the G-strand to which the 3' portion of the extension primer hybridizes.

As used herein, "G-strand of the chromosomal DNA" means the strand of the telomere having the 3' overhang, and includes the telomeric repeat sequence 5'-TTAGGG-3'. For example, "G-strand of the chromosomal DNA" can refer to the DNA strand in a chromosome comprising the $(TTAGGG)_n$ telomeric sequence in humans and other vertebrates.

As used herein, a "polymerase" refers to an enzyme that catalyzes the polymerization of nucleotides. Generally, the enzyme will initiate synthesis at the 3'-end of the primer annealed to a nucleic acid template sequence. "DNA polymerase" catalyzes the polymerization of deoxyribonucleotides. Known DNA polymerases include, for example, *Pyrococcus furiosus* (Pfu) DNA polymerase (Lundberg et al., (1991) Gene 108:1), *E. coli* DNA polymerase I (Lecomte and Doubleday (1983) Nucleic Acids Res. 11:7505), T7 DNA polymerase (Nordstrom et al. (1981) J. Biol. Chem. 256:3112), *Thermus thermophilus* (Tth) DNA polymerase (Myers and Gelfand (1991) Biochemistry 30:7661), *Bacillus stearothermophilus* DNA polymerase (Stenesh and McGowan (1977) Biochim Biophys Acta 475:32), *Thermococcus litoralis* (Tli) DNA polymerase (also referred to as Vent DNA polymerase, Cariello et al. (1991) Nucleic Acids Res 19:4193), *Thermotoga maritima* (Tma) DNA polymerase (Diaz and Sabino (1998) Braz J. Med. Res 31:1239), and *Thermus aquaticus* (Taq) DNA polymerase (Chien et al., (1976) J. Bacteoriol 127:1550). The polymerase activity of any of the above enzymes can be determined by means well known in the art.

As used herein, "thermostable" DNA polymerase activity means DNA polymerase activity which is relatively stable to heat and functions at high temperatures, for example 45-100° C., preferably 55-100° C., 65-100° C., 75-100° C., 85-100° C. or 95-100° C., as compared, for example, to a non-thermostable form of DNA polymerase.

Strand displacement activity of a DNA polymerase describes the ability to displace downstream DNA encountered during synthesis. For example, Strand displacement activity of a DNA polymerase can refer to the polymerases ability to separate a double strand of DNA into two single strands. Examples of DNA polymerases with strand displacement activity are holoenzymes or parts of replicases from viruses, prokaryotes, eukaryotes or archaea, the phi29 DNA polymerases, Klenow DNA polymerase exo⁻ and DNA polymerase from *Bacillus stearothermophilus* designated as Bst exo⁻. "Exo⁻" signifies that the corresponding enzyme does not have 5'-3' exonuclease activity. A well known example of a phi29 DNA polymerase is the bacteriophage phi29 DNA polymerase. Further suitable DNA polymerases with strand displacement activity useful in the methods of the present invention are well known to the person skilled in the art, and include DNA polymerases such as a modified T7 polymerase, (e.g, Sequenase), exonuclease-deficient Klenow fragment of *E. coli* DNA polymerase I, and Bst DNA polymerase Large fragment and Deep VentR (exo-).

Alternatively, also understood to be DNA polymerases with strand displacement activity are those without strand displacement activity provided a catalyst is used in addition to a respective DNA polymerase, e.g. a protein or enzyme, which enables a double strand of DNA to be separated or a single strand of DNA to be stabilized. These proteins include, for example, the helicases, SSB proteins and recombinant proteins, which can be present as components of larger enzyme complexes, such as replicases. In this case, a polymerase with strand displacement activity is produced with components in addition to the polymerase itself. The polymerases with strand displacement activity can be either heat-unstable or heat-stable.

As used herein, "primer" refers to an oligonucleotide capable of acting as a point of initiation of DNA synthesis under conditions in which synthesis of a primer extension product complementary to a nucleic acid strand is induced, e.g., in the presence of four different nucleoside triphosphates and an agent for extension (e.g., a DNA polymerase or reverse transcriptase) in an appropriate buffer and at a suitable temperature. A primer need not reflect the exact sequence of the template nucleic acid, but must be sufficiently complementary to hybridize with the template. The design of suitable primers for the amplification of a given target sequence is well known in the art and described in the literature cited herein.

The terms "target, "target sequence", "target region", and "target nucleic acid," as used herein, are synonymous and refer to a region or subsequence of a nucleic acid which is to be amplified or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., (1989) Molecular Cloning—A Laboratory Manual (Cold Spring Harbor Laboratory, Cold Spring Harbor, N.Y.); and Wetmur (1991) Critical Review in Biochem. and Mol. Biol. 26 (3/4):227-259; both incorporated herein by reference).

The term "amplification reaction" refers to any chemical reaction, including an enzymatic reaction, which results in increased copies of a template nucleic acid sequence or results in transcription of a template nucleic acid.

Polymerase chain reaction (PCR) is a method that allows exponential amplification of DNA sequences within a longer double stranded DNA molecule. PCR entails the use of a pair of primers that are complementary to a defined sequence on each of the two strands of the DNA. These primers are extended by a DNA polymerase so that a copy is made of the designated sequence. After making this copy, the same primers can be used again, not only to make another copy of the input DNA strand but also of the short copy made in the first round of synthesis. This leads to logarithmic amplification. Since it is necessary to raise the temperature to separate the two strands of the double strand DNA in each round of the amplification process, a major step forward was the discovery of a thermo-stable DNA polymerase (Taq polymerase) that was isolated from *Thermus aquaticus*, a bacterium that grows in hot pools; as a result it is not necessary to add new polymerase in every round of amplification. After several (often about 40) rounds of amplification, the PCR product is analyzed on an agarose gel and is abundant enough to be detected with an ethidium bromide stain.

It is understood that real-time PCR, also called quantitative real time PCR (qRT-PCR), quantitative PCR (Q-PCR/qPCR), or kinetic polymerase chain reaction, is a laboratory technique based on PCR, which is used to amplify and simultaneously quantify a targeted DNA molecule. qPCR enables both detection and quantification (as absolute number of copies or relative amount when normalized to DNA input or additional normalizing genes) of a specific sequence in a DNA sample.

As used herein, a primer is "specific," for a target sequence if, when used in an under sufficiently stringent conditions, the primer hybridizes primarily only to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in most cases. Hybridization conditions can be chosen under which the primer can form stable duplexes only with a target sequence. Thus, the use of target-specific primers under suitably stringent amplification conditions enables the specific amplification of those target sequences which contain the target primer binding sites. The use of sequence-specific amplification conditions enables the specific amplification of those target sequences which contain the exactly complementary primer binding sites.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides.

It is understood in the art that a nucleic acid molecule need not be 100% complementary to a target nucleic acid sequence to be specifically hybridizable. That is, two or more nucleic acid molecules may be less than fully complementary and is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

The term "non-specific amplification," as used herein, refers to the amplification of nucleic acid sequences other than the target sequence which results from primers hybridizing to sequences other than the target sequence and then serving as a substrate for primer extension. The hybridization of a primer to a non-target sequence is referred to as "non-specific hybridization" and is apt to occur especially during the lower temperature, reduced stringency, pre-amplification conditions.

The term "primer dimer," as used herein, refers to a template-independent non-specific amplification product, which is believed to result from primer extensions wherein another primer serves as a template. Although primer dimers frequently appear to be a concatamer of two primers, i.e., a dimer, concatamers of more than two primers also occur. The term "primer dimer" is used herein generically to encompass a template-independent non-specific amplification product.

The term "reaction mixture," as used herein, refers to a solution containing reagents necessary to carry out a given reaction. An "amplification reaction mixture", which refers to a solution containing reagents necessary to carry out an amplification reaction, typically contains oligonucleotide primers and a DNA polymerase or ligase in a suitable buffer. A "PCR reaction mixture" typically contains oligonucleotide primers, a DNA polymerase (most typically a thermostable DNA polymerase), dNTPs, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction components which includes the blocked primers of the disclosure.

1. Introduction

This disclosure provides methods and materials for determining measures of short telomere abundance in a population of chromosomes and of using these measures for determining measures of health and effects of interventions that increase or decrease telomere length and, hence, increase or decrease health, or conversely decrease or increase risk of future disease or death, respectively. The methods involve producing a population of copies of chromosomal fragments only from chromosomes having telomeres within a pre-defined length range (e.g., all telomeres no longer than a certain length, e.g., shorter than about 5 kbp). This assay can be used to represent the relative abundance of short telomere telomeres in a set of samples, or the assay can be used in combination with a measure of total telomere abundance in order to generate an absolute percentage of short telomeres.

In one aspect, the method of measuring the abundance of short telomere products includes two steps. A first step involves generating extension products from a double-stranded chromosomal DNA template using an extension primer. The extension primer has at its 3' end a sequence complementary to telomeric repeat sequences in the G-strand of the telomere, and an "anchor" sequence at its 5' end. In this way, the extension primer is adapted to hybridize to a telomeric repeat sequence in the 3' overhang of chromosomes in a sample, and utilizes a 5'-anchor sequence for priming a subsequent PCR reaction. The extension products are generated in a time-limited extension reaction. Because it is time limited, the extension reaction can be configured to produce extension products of no more than a certain length. Because the extension products are length limited, they will extend into the sub-telomeric region only in chromosomes that are sufficiently short. A second step involves amplifying, from the extension products, sequences bounded by a sub-telomeric sequence and the anchor sequence.

The length of the extension products produced by defined reaction times can be estimated by at least three different methods: (a) by the polymerization rate (R) of the strand displacement enzyme times the extension time: (b) by analyzing the size of PCR products on a Southern gel; and (c) by analyzing the size of the pure TTAGGG region by sequencing. The sequencing method is limited by the ability to accurately sequence long stretches of repetitive DNA.

Because the extension reaction is time-limited, sub-telomeric sequences will be present only in extension products from chromosomes in which the distance from the location in the 3' overhang where the extension primer hybridized to the sub-telomeric region is within a pre-determined length range of extension. The pre-determined length range and can be up to any length chosen by the practitioner. For example, the length range can be a length up to a pre-determined length. In certain aspects, the length range embraces the length of short telomeres, e.g., up to 5 kb. In other aspects, the length range is a length shorter than a pre-determined distance. So, for example, in chromosomes in which the length of the telomere is no longer than the defined extension length (e.g., chromosomes with short telomeres), the time-limited extension reaction will extend the primer into the sub-telomeric region of the chromosome. In chromosomes in which the length of the telomere is longer than the pre-determined extension length (e.g., chromosomes with long telomeres), the time-limited extension reaction will not extend the primer into the sub-telomeric region of the chromosome, and the extension product will not have the sub-telomeric sequences necessary for the second amplification step. Accordingly, the population of extension products can be controlled to include telomeric sequences only from chromosomes having telomeres shorter than a certain size. If the length range is, for example, 4 kb, the extension products include, for example, products in which the telomeres are 4 kb, 3 kb, 2 kb, 1 kb, etc.

When the extension products are amplified using a pair of amplification primers adapted to amplify sequences bounded by a sub-telomeric sequence and the anchor sequence, only extension products having sub-telomeric sequences are amplified. Those are the extension products generated from chromosomes having telomeres shorter than the defined extension length, e.g., chromosomes with short telomeres. Accordingly, the extended product is not amplified from total telomeric sequences from chromosomes in the sample, but only from telomeric sequences from chromosomes having telomeres no greater than the predefined length. Such an amplified product is sometimes referred to herein as a "length-limited telomere amplification product" or, depending on context, a "short telomere amplification product". By using limited extension time in this PCR amplification step, the short telomeres will be further enriched. This limited extension time PCR step therefore will increase the specificity of the assay to amplify only the short telomere population.

The amount or abundance of telomeric sequences in a length-limited telomere amplification product is sometimes referred to herein as "length-limited telomere abundance" or, depending on context, "short telomere abundance". The abundance of telomeric sequences in a length-limited telomere amplification product can be measured by any method used to determine abundance of telomeric sequences in a product of total telomeric sequences.

Methods of this disclosure begin with double stranded DNA, e.g., chromosomes in their native state. In comparison methods that measure total telomeric sequences, particularly this use qPCR, can involve providing a sample of single-stranded, or denatured, nucleic acid.

2. Length-limited Telomere Amplification Product 2.1 Sample

Chromosomal DNA in its native, double-stranded state, can be obtained from a solid, fluid, semisolid or gaseous sample containing nucleic acid, e.g., from liquid tissues such as blood, saliva, urine, plasma, serum, CSF, bronchoalveolar lavage fluid; from solid tissues such as lung, muscle, skin; from semi-solid tissues such as bone marrow; and from gaseous sample such as exhaled breath. The organisms from which the chromosomal DNA is obtained can be any organism with linear chromosomes with a 3' overhang. The template double stranded chromosomal DNA can be obtained using any DNA purification method which yields high molecular weight genomic DNA (greater than 20 kb) including phenol/chloroform extraction, cesium chloride gradient, and commercial kits that use silicone membrane binding technology, selective detergent-mediated DNA precipitation method. Examples of DNA purification commercial kits include Agencourt DNAdvance and Agencourt Genfind (Beckman Coulter), QIAamp kit (QIAGEN, Valencia, Calif.), QIAamp blood kit (QIAGEN), QIAamp FFPE tissue kit QIAGEN), AHPrep kit (QIAGEN), Puregene kit (QIAGEN), PureLink and GeneCatcher (Invitrogen) and Wizard (Promega).

A sample for use in the methods of this disclosure can be any genomic DNA with 3' end single-stranded overhang. In certain aspects, the sample comprises high molecular weight genomic DNA (e.g., >20 kb). Any method that yields high molecular weight native genomic DNA can be used.

In double-stranded chromosomes possessing telomeres, the single DNA strand having a 3' terminus with the telomeric repeat sequence (the "3' overhang") extends beyond the terminus of the paired single strand having the 5' terminus. The strand of the telomere having the 3' overhang is referred to as the "G strand", and includes the telomeric repeat sequence 5'-TTAGGG-3'. Same order permutations are permutations in which the letters are not scrambled, but begin at a different point in the same sequence, e.g., inversions (e.g., XYZ, YZX, ZXY rather than YXZ). Same order permutations of this sequence include: 5'-TAGGGT-3', 5'-AGGGTT-3', 5'-GGGTTA-3', 5'-GGTTAG-3' and 5'-GT-TAGG-3'. The strand having the 5' terminus is referred to as the "C strand", and includes the telomeric repeat sequence 5'-CCCTAA-3'.

The length of a telomere can be the distance, e.g., in kilobases, from the end of the chromosome to the sub-telomeric region. In cells of normal human adults, telomeres can range from less than 1 kb to 12 kb or, in some cases, to >20 kb in length. Telomere length is known to vary in different cell types (Lin et al., *J Immunol Methods*, 2010, 31:352(1-2):71-80). For these reasons, the useful length ranges of the short telomere population can be broad, based on clinical utility. Accordingly, in certain aspects, a short telomere has a length no more than about 5 kb, no more than 4 kb, no more than 3 kb, no more than 2 kb, no more than 1 kb or no more than about 0.5 kb. Methods of this disclosure can be configured to detect telomeres up to each of these lengths.

Short telomere products can be generated from a single telomere, a single chromosome, a population of chromosomes from a single cell or a population of chromosomes from a plurality of cells.

2.2 Producing the Extension Product

In the extension reaction, a primer is annealed to the 3' overhang of the double stranded chromosomal DNA under annealing conditions. Appropriate annealing conditions are known to those skilled in the art, such as those typically used to hybridize nucleic acid strands for strand extension or for PCR. Such conditions include, without limitation, incubation at 65° C. for 10 min in a heating block and then cooling down to room temperature over the period of one hour. Other conditions may include incubation at temperature ranging from 37° C. to 65° C. for at 5 minutes to 30 minutes and then cooling down to room temperature over the period of one hour to three hours.

2.2.1 Extension Primer

The extension primer comprises a 3' portion and a 5' portion.

2.2.1.1 3' Portion

The 3' portion has a sequence adapted to hybridize a telomeric repeat sequence in the G-strand of a telomere. The sequence in the 3' portion can be complementary to the telomeric repeat, or it can have certain mismatches as described above, as long as the mismatches allow for hybridization under annealing conditions for primer extension. For example, the 3' portion can have at least 8 consecutive nucleotides of a telomeric repeat sequence (i.e., the sequence of the C-strand of the telomere). The consecutive nucleotides can be in any permutation of the telomeric repeat sequence. In other aspects, the sequence of the 3' portion can have at least 9 consecutive nucleotides, at least 10 consecutive nucleotides, at least 11 consecutive nucleotides or at least 12 consecutive nucleotides of a telomeric repeat sequence. In other aspects, the sequence of the 3' portion can have two or more, three or more, or four or more telomeric repeat units in any same-order permutation.

2.2.1.1 5' Portion

The 5' portion of the extension primer (also referred to as an "anchor sequence") is configured not to hybridize under annealing conditions to a telomeric repeat sequence in the G-strand to which the 3' portion hybridizes. Preferably, the anchor sequence does not hybridize under annealing conditions to a sequence in the sub-telomeric region of the G-strand. The anchor sequence also can be configured not to hybridize to any sequence of the target G-strand within 10 kb, within 20 kb or within 50 kb of the terminus of the 3' overhang of the G-strand, or to any unique sequence in the target chromosome. The anchor sequence can be configured such that its complement does not hybridize to any sequence in the C-strand of the chromosome in the telomeric or sub-telomeric region, or within 10 kb, within 20 kb or within 50 kb of the terminus of the C-strand of the telomere. For example, the anchor sequence can be a unique sequence not found in the chromosomes being tested.

2.2.2 Extension Reaction

After annealing the extension primer to the chromosomal DNA, an extension reaction is performed using a polymerase with strand displacement activity and/or exonuclease activity. Examples of strand displacement polymerases include, but are not limited to T7 polymerase (e.g., Sequenase), exonuclease-deficient Klenow fragment of *E. coli* DNA polymerase I, and Bst DNA polymerase Large fragment and Deep VentR (exo-). In addition, polymerases with 5'-3' exonuclease activity can also be used.

The extension reaction is time limited. That is, the extension reaction is allowed to proceed for a pre-determined amount of time. The time is calibrated to produce extension products having an average of no more than a pre-determined length. The time used to produce the extension product by the strand-displacement enzyme can be determined empirically under the chosen conditions and reactants to produce extension products of pre-determined length. The extensions rates of various polymerases useful in the present invention have been previously determined, and the extension rates can be used to calculate the approximate time necessary to achieve the desired extension product. The extension rates for exemplary polymerases are given in the table below.

| DNA Polymerase | Extension Rate* | Reference |
| --- | --- | --- |
| Klenow | 13.5 nucleotides/sec | Maier B, Bensimon D, and Croquette V. *Proc Natl Acad Sci USA.* (2000) 2497(22): 12002-7. |
| T7 | 75.9 nucleotides/sec | Tanner, N. A. et al. *Nuc. Acids Res.* (2009) 37, e27. |
| Taq | 35-100 nucleotides/sec (75° C.) 0.9-2.55 nucleotides/sec (37° C.) | Wittwer, C. T. and Garling, D. J., BioTechniques (1991) 10(1), 76-83. |
| phi29 | 25 nucleotides/sec | Blanco, L., et al. J Biol Chem (1989) 264, 8935-8940 |
| Bst | 50-100 nucleotides/sec | New England Biolabs |

*Under conditions specified in the associated reference or standard reaction conditions in the absence of other information.

Initiation of the extension reaction is achieved by adding the strand displacement enzyme to the reaction tube. Reaction can be stopped by placing the reaction tube to 80° C. for 20 minutes or by adding EDTA. Furthermore, the reaction can be controlled (slowed down or sped up) by incubating at a lower or higher temperature, e.g. 25° C. or 30° C. For instance, the displacement rate of the strand displacement polymerase Sequenase at 37° C. is about 28 bp per second. At 30° C. it is about 3-fold slower, based on Southern blot analysis. At 37° C., Sequenase can produce an extension product of ~1 kb in 30 sec; ~2 kb in 1 minute; ~5 kb in 3 minutes; and ~8 kb in 5 minutes. The timing necessary to produce extension products of pre-determined lengths with various polymerase systems and various sample sources can be determined empirically, e.g., a similar time course experiment followed by Southern blot analysis can be performed to calibrate the extension time. Accordingly, the extension reaction can be timed to no more than 30 minutes, no more than 10 minutes, no more than 5 minutes, no more than 4 minutes, no more than 3 minutes, no more than 2 minutes, no more than 1 minute or no more than 30 seconds.

2.3 Amplification Reaction

Sequences in the time-limited extension product are then amplified, for example, by PCR. More specifically, sequences bounded by the anchor sequence on one side and a sub-telomeric sequence on the other side are amplified. The primer can be exactly complementary or have mismatched sequences, as long as it allows annealing to its target (anchor sequence or sub-telomeric sequence) and extension.

Anchor sequences can vary. In certain aspects, the anchor sequence is a specific sequence not present in the genome of the organism for which telomere quantity is being measured, or if the anchor sequence is found elsewhere in the genome, it could still be useful if that sequence is a significant distance from the SUS sequence, so that no amplification occurs during the PCR step except between the telomeric anchor sequence and the telomeric SUS sequence.

PCR conditions are optimized to yield best analytic performance. The extension time in the PCR condition is predetermined by examining the product profile on Southern blots to ensure that the intended size range of short telomeres are enriched.

The subtelomeric primer used in the method of the disclosure can contain sequences on the G strand, found in all or most chromosomes, e.g. variants of the telomeric sequence (TGAGGG)$_{3-6}$ (Xu and Blackburn, *Mol. Cell,* 28:315-327, 2007) or (TTGGGG)$_{3-6}$ (Allshire et al., *Nucleic Acid Research,* 17:4611-4627, 1989), or (TCAGGG)$_{3-6}$ (Baird et al., *EMBO J.,* 14(21):5433-5443, 1995). Alternatively, the sub-telomeric primer could be a segment found on specific chromosome(s), e.g. the XpYpE2 primer described in Xu et al (5'-GTTGTCTC AGGGTCCTAGTG-3' [SEQ ID NO:1]) (Xu and Blackburn, *Mol Cell,* 28:315-327, 2007). In one aspect, the primer for the sub-telomeric sequence comprises, consists essentially of or consists of:

[SEQ ID NO: 2]
5'-GATGGATCCTGAGGGTGAGGGTGAGGG-3'

[SEQ ID NO: 10]
5'-CGGGCCGGCTGAGGGTACCGCGA-3' (chromosome 1)

[SEQ ID NO: 11]
5'-GCTAATGCACTCCCTCAATAC-3' (chromosome 5)

[SEQ ID NO: 12]
5'-CATTCCTAATGCACACATGATACC-3' (Chromosome 9)

When a short telomere assay is applied in organisms other than human using the methods of the disclosure, the specific sequence of the subtelomeric primer can be designed based on the genome sequence of the organism. The sequence of the sub-telomeric primer should match with the strand with the 3' overhang.

The amplification product comprises a population of nucleic acids having telomeric repeat sequences within a certain length range, and excludes sequences longer than this range. Thus, the population can be configured to include sequences only from chromosomes having telomeres shorter than a threshold length.

An internal control sequence to control for the extension reaction efficiency can be included in the extension reaction step. This internal control sequence can be a double strand DNA with subtelomeric primer sequence at one end and a 3' overhang with the G strand of telomeric sequence. Between the subtelomeric primer sequence and telomeric sequence can be a stretch of unique non-telomeric sequence. One such sequence can be, for example, the hTERT gene, or the RNase P gene. The efficiency of the extension reaction for this internal control can be measured by a Taqman based assay to quantify, for example the hTERT gene or the RNase P gene.

3. Methods of Measuring Telomere Abundance

Any method used to measure telomere abundance in a sample comprising telomeric sequences can be used to measure telomere abundance in a length-limited telomeric sample.

Measures of telomere abundance can be absolute or relative. Absolute measures of telomere abundance include, for example, total length of telomere sequences in a genome measured, for example, by number of nucleotides. More typically, telomere abundance is measured relative to a reference. Detection of telomere sequences can be measured in terms of signal strength produced in an assay. This signal strength can be compared with the signal strength produced by a reference sequence in the assay. The relative signal strength can function as a method of standardization. Standardized methods can be compared more easily between assays. For example, the signal produced by detection of telomere sequences can be compared with the signal produced by the measure of a control sequence. The control sequence can be, for example, a portion of the beta-globin gene. Thus, regardless of the assay method used, the relative signals of telomere sequences to reference sequences can be expressed, for example, as a ratio. This ratio can be used to compare results of telomere sequence abundance measurements.

In other aspects, measures of short telomere abundance are compared with total telomere abundance. The total telomere abundance can be measured by a long extension time in the strand displacement reaction and in the amplification reaction, followed by qPCR method as described in U.S. Pat. No. 7,695,904 (Cawthon) and Lin et al. (Lin et al, 2010, 352(1-2):71-80). To determine the percentage of short telomeres, the ratio of short telomeres to total telomeres can be determined. For example, the signal strength of the short telomere measurement can be divided by the signal strength of the total telomere measurement.

3.1 qPCR

One method of quantifying the abundance of the short telomeres is quantitative PCR, as described in by Cawthon (*Nucleic. Acids Res.*, 2002, 30(10):e47; in U.S. Pat. No. 7,695,904; Lin et al., *J. Immunol. Methods,* 2010, 352(1-2): 71-80); or Cawthon 2009 (Nucleic Acids Res. 2009 37(3): e21.).

A variety of methods known in the art can be used in the present disclosure to determine average telomere length or telomere abundance. Preferably, the real time kinetic quantitative polymerase chain reaction (qPCR) is utilized as specifically modified for telomere length detection by Cawthon (*Nucleic. Acids Res.,* 2002, 30(10):e47; U.S. Pat. No. 7,695,904). The method is simple and allows for rapid high throughput processing of large numbers of DNA samples. The qPCR method is based on the detection of the fluorescence produced by a reporter molecule which increases as the polymerase chain reaction proceeds. This increase in fluorescence occurs due to the accumulation of the PCR product with each cycle of amplification. These fluorescent reporter molecules include dyes that bind to the double-stranded DNA (for example, SYBR Green or ethidium bromide) or sequence specific probes (for example, Molecular Beacons or TAQMAN Probes). Alternatively, the qPCR method described by Cawthon (*Nucleic Acids Res.* 2009, 37(3):e21) can be used The method allows determination of T/S ratios in a single sample via multiplexing, including experimental contexts when the telomere repeats are the high abundance species and a single copy gene is the low abundance species.

In the method of the present disclosure, primer probes specific to the repeated telomere sequence $(TTAGGG)_n$ are used. The size of the primer may vary, in general, from 5 to 500 nucleotides in length, between 10 and 100 nucleotides, between 12 and 75 nucleotides, or between 15 to 50 nucleotides, depending on the use, required specificity, and the amplification technique. In the present disclosure, one aspect utilizes a first primer which hybridizes to a first single strand of the target telomere sequence and a second primer which hybridizes to a second single strand of the target telomere sequence, where the first and second strands are substantially complementary. In this aspect, for example, the paired primer set consisting of tel1 (5'-GGTTTTTGAGGGT-GAGGGTGAGGGTGAGGGTGAGGGT-3') [SEQ ID NO: 3] and tel2 (5'-TCCCGACTATCCCTATCCCTATCCCT-ATCCCTATCCCTA-3') [SEQ ID NO: 4] can be used. In one aspect, at least one of the primers comprises at least one altered or mutated nucleotide residue, which produces a mismatch between the altered residue and the 3' terminal nucleotide of the other primer when the primers hybridize to each other. The presence of a mismatch at the 3' terminal nucleotide blocks extension by polymerase, thus limiting non-target nucleic acid dependent extension reactions. In this aspect, for example, the paired primer set consisting of tel 1b 5'-CGGTTTGTTTGGGTTTGGGTTTGGGTTTG-GGTTTGGGTT-3' [SEQ ID No.: 5]; and tel 2b 5'-GGCT-TGCCTTACCCTTACCCTTACCCTTACCCTTACCCT-3' [SEQ ID No.: 6] can be used. In a further aspect, for example, the paired primer set consisting of telg 5'-ACACTAAGGTTTGGGTTTGGGTTTGGGTTTGGGTT-AGTGT-3' [SEQ ID No.: 13]; and telc 5'-TGTTAGGTATC-CCTATCCCTATCCCTATCCCTATCCCTAACA-3' [SEQ ID No.: 14] can be used. One skilled in the art will appreciate that other substantially complementary or mismatched sets of primers may be employed in this disclosure. Such primers are described in U.S. Pat. No. 7,695,904 (Cawthon et al.).

Amplification reactions are carried out according to procedures well known in the art. Procedures for PCR are widely used and described (see for example, U.S. Pat. Nos. 4,683,195 and 4,683,202). In brief, a double stranded target nucleic acid is denatured, generally by incubating at a temperature high enough to denature the strands, and then incubated in the presence of excess primers, which hybridize (anneal) to the single-stranded target nucleic acids. A DNA polymerase extends the hybridized primer, generating a new copy of the target nucleic acid. The resulting duplex is denatured and the hybridization and extension steps are repeated. By reiterating the steps of denaturation, annealing, and extension in the presence of a second primer for the complementary target strand, the target nucleic acid encompassed by the two primers is exponentially amplified. The time and temperature of the primer extension step will depend on the polymerase, length of target nucleic acid being amplified, and primer sequence employed for the amplification. The number of reiterative steps required to sufficiently amplify the target nucleic acid will depend on the efficiency of the amplification. One skilled in the art will understand that the present disclosure is not limited by variations in times, temperatures, buffer conditions, and amplification cycles applied in the amplification process.

The products of the amplification are detected and analyzed by methods well known in the art. Amplified products may be analyzed following separation and/or purification of the products, or by direct measurement of product formed in the amplification reaction. For detection, the product may be identified indirectly with fluorescent compounds, for example, with ethidium bromide or SYBR Green, or by hybridization with labeled nucleic acid probes. Alternatively, labeled primers or labeled nucleotides are used in the amplification reaction to label the amplification product. The label comprises any detectable moiety, including fluorescent labels, radioactive labels, electronic labels, and indirect labels such as biotin or digoxigenin.

Instrumentation suitable for conducting the qPCR reactions of the present disclosure are available from a number of commercial sources (ABI Prism 7700, Applied Biosystems, Carlsbad, Calif.; LIGHTCYCLER 480, Roche Applied Science, Indianapolis, Ind.; Eco Real-Time PCR System, Illumina, Inc., San Diego, Calif.; RoboCycler 40, Stratagene, Cedar Creek, Tex.).

When real time quantitative PCR is used to detect and measure the amplification products, various algorithms are used to calculate the number of target telomeres in the samples. (For example, see ABI Prism 7700 Software Version 1.7; Lightcycler Software Version 3). Quantitation may involve use of standard samples with known copy number of the telomere nucleic acids and generation of standard curves from the logarithms of the standards and the cycle of threshold ($C_t$). In general, $C_t$ is the PCR cycle or fractional PCR cycle where the fluorescence generated by the amplification product is several deviations above the baseline fluorescence.

3.2 Other Methods

The abundance of short telomeres from the amplification reaction may be measured by other methods known in the art. Such methods include, but are not limited to, direct nucleic acid sequencing and Southern blotting, and dot blot, or slot blot hybridization and digital PCR.

Conventional techniques for the direct determination of nucleic acid sequences in isolated DNA may be employed in the present disclosure. For example, see: "DNA Sequencing," *The Encyclopedia of Molecular Biology*, J. Kendrew, ed., Blackwell Science Ltd., Oxford, U K, 1995, pp. 283-286. Dye-terminator automated sequencing is now most commonly used for nucleic acid sequencing ("DNA Sequencing", *Lab Manager*, at world wide web URL lab-manager.com/?articles.view/articleNo/3364/article/DNA-Sequencing). Automated sequencing equipment is conveniently used and may be purchased from companies such as Applied Biosystems, Roche Applied Science, and Illumina Inc. Once the sequence of a DNA sample is determined, the number of copies of the telomere nucleotide sequence (TTAGGG) at either end can then be counted. This method of the present disclosure provides a measure of absolute telomere abundance by direct measurement of telomeric sequences.

Southern blotting (Southern, E. M., *J. Mol. Biol.*, 1975, 98(3): 503-517) may also be utilized in the present disclosure to determine telomere abundance by detecting the specific presence of the human telomere nucleotide sequence $(TTAGGG)_n$. In the present disclosure, Terminal Restriction Fragment (TFR) Southern blotting combines the transfer of DNA fragments separated by electrophoresis to a filter membrane, followed by detection of the fragments by hybridization to probes specific for the (TTAGGG) sequence (Allshire, R. C. et al., *Nucleic Acids Res.*, 1989, 17, 4611-4627). Such probes have sequences complementary to the telomere sequence. For ease of detection, probes are radioactively labeled or tagged with a fluorescent or chromogenic dye. The amount of radioactivity or fluorescence present may then be quantified to give the telomere abundance in the sample. M. Kimura et al. (*Nature Protocols*, 2010, 5:1596-1607) describes an appropriate Southern blot procedure for determining telomere length.

Variations of the Southern blotting method include dot blot, or slot blot, where the DNA is spotted as dots or slots on a filter membrane, followed by detection of the fragments by hybridization to probes specific for the (TTAGGG) sequence (Kimura M, Aviv A, *Nucleic Acids Res.*, 2011, 39(12):e84. doi: 10.1093/nar/gkr235. Epub 2011 Apr. 27).

In the above aspects of the present disclosure, fluorescence may be measured in relative fluorescence units (RFU). Fluorescence is detected using a charged coupled device (CCD) array, when the labeled fragments, which are separated within a capillary by using electrophoresis, are energized by laser light and travel across the detection window. A computer program measures the results, determining the quantity or size of the telomere-containing fragments, at each data point, from the level of fluorescence intensity ("Relative fluorescence unit (RFU)", DNA.gov: Glossary, April 2011, world wide web URL dna.gov/glossary/).

Measures of telomere abundance can be measured using DNA sequencing methodologies. Such methods can involve sequencing molecules in a sample that comprise telomeric repeats, and determining the abundance of telomeric repeat sequences. DNA sequencing methods can include any known method of sequencing including, for example, classical sequencing methods, such as Sanger sequencing or Maxam Gilbert sequencing, and next generation sequencing methods, such as ligation sequencing, nanopore sequencing, pyrosequencing, superpyro sequencing, sequencing by proton detection, sequencing-by-synthesis and, single-molecule sequencing. Short telomere abundance can be also measured by digital PCR. Such technique platforms include, but not limited to, the digital PCR, including, for example, the RAINDROP Digital PCR System (Raindance Technologies, Billerica, Mass.) or the QX200 DROPLET DIGITAL PCR System (Bio-Rad Laboratories, Hercules, Calif.), microfluidic digital PCR (Fluidigm Corporation, South San Francisco, Calif.), or the OPENARRAY Real-Time PCR System (APPLIED BIOSYSTEMS division of Thermo Fisher Scientific, Inc., Waltham, Massachussetts). In various further aspects, the abundance of short telomeres can be measured by a suitable hybridization technology, e.g. digital color-coded barcode methods such as NCOUNTER Analysis System (Nanostring Technologies, Seattle, Wash.).

4. Kits

This disclosure also provides kits useful in the methods of this disclosure. Such kits can include an extension primer of this disclosure and an amplification primer that hybridizes to a sub-telomeric sequence or to the complement of an anchor sequence of the extension primer. Alternatively, the kit can include an extension primer of this disclosure and a pair of amplification primers adapted to amplify a sequence in a nucleic acid bounded by a sub-telomeric sequence and an anchor sequence in the extension primer. The kit can include a container that contains the extension primer and another container that contains one or both of the amplification primers. The kit also can include reagents for primer extension and reagents for nucleic acid amplification, e.g., for PCR. The kit can also include control and reference samples with known values. In certain aspects, the kit includes an extension primer and a pair of amplification primers. In certain aspects, the extension primer comprises a 3' portion that hybridizes to a telomeric repeat sequence in a 3' overhang of double-stranded chromosomal DNA under annealing conditions, and a 5' anchor portion that does not hybridize to sequences in the telomeric or sub-telomeric regions.

5. Conditions Correlated with Telomere Abundance, Abundance of Short Telomeres, and Rate of Change in Telomere Abundance or Rate of Change in Abundance of Short Telomeres In general, conditions associated with telomere abundance have typically been derived using a measure of average telomere length, as described herein. However, as discussed above, emerging data suggest that the measuring the abundance of short telomeres, and or the rate of change in abundance of short telomeres may be a more sensitive and potentially a more accurate predictor of clinically meaningful outcomes (e.g. disease or mortality risk) than is the measurement of average telomere length or the rate of change in average telomere length. Hence it is important to have sensitive and accurate measurement of the abundance of short telomeres. It has been reported that the presence of critically short telomeres caused loss of cell viability and tissue function, indicating that there is a causal relationship between very short telomeres and cell senescence (Hemann, M. T., et al. Cell, 2001. 107(1) 67-77).

Although short average telomere length (as discussed below) is an established, good predictor of clinical outcomes, it is expected that accurate measurement of the abundance of short telomeres may be a more sensitive measurement for the effects of intervention on telomere dynamics (Canela, A., et al. Proc Natl Acad Sci USA, 2007. 104(13) 5300-5). Harley et al. (Rejuvenation Res. 2011. 14(1) 45-56) showed that humans taking a relatively weak activator of telomerase, TA-65®, showed a reduction in percentage of short telomeres, but there was not a significant shift in average telomere length. In Vera et al. supra., the rate of increase in abundance of short telomeres predicted increased longevity in two separate cohorts of mice "The Rate of Increase of Short Telomeres Predicts Longevity in Mammals, Cell Reports (2012), world wide web URL: dx.doi.org/10.1016/j.celrep.2012.08.023). Due to the lack of an accurate, cost effective, high throughput method for measuring the abundance of short telomeres, there has until now been no large human clinical studies using abundance of short telomeres or the rate of change in abundance of short telomeres to establish the clinical utility of measuring the abundance of short telomeres.

Proof of concept in animal studies from Vera et al., supra also indicate that mice with a high rate of increase over time in the percentage of short telomeres have reduced survival compared to mice with a low rate of increase in percentage of short telomeres over time. In wild type mice, the difference in survival of mice that had a low rate of increase (e.g., 0.4%/month) compared to mice with a high rate of increase (e.g. 1%/month) was about 100 weeks, or nearly two thirds of the maximum survival in the wild type mice.

Accordingly, humans with a high percentage of short telomeres as measured by an accurate and precise assay as described herein, will be more prone to disease or mortality risk compared to humans with a low percentage of short telomeres. Quantitative assessment of % short telomeres will have significant diagnostic utility in not only health monitoring but disease diagnostics, prognosis, and companion diagnostics.

Monitoring the abundance of short telomeres has immediate utility for health monitoring since it is known that short telomeres (typically less than 1 kbp or less then 2 kpb or less than 3 kbp) trigger cellular senescence (Hemann, M. T., et al. Cell, 2001. 107(1) 67-77), and cellular senescence is known to lead to loss of tissue function and ultimately disease and mortality. Thus, an individual with a greater than average abundance of short telomeres compared to an age-matched reference population of normal individuals is at increased risk of morbidity or mortality. Such a person would be motivated to change their behavior towards a better lifestyle and lower abundance of short telomeres, while an individual with a lower than average abundance of short telomeres compared to the reference population would know that their cellular health was likely better than average, and hence would be motivated to at least to maintain, if not further improve, their lifestyle habits to maintain their good health.

Average telomere length per chromosome end determined from genomic DNA is a measure of overall telomere abundance, and this has been shown to correlate with several important biological indices. These indices include, for example, risk of various disease conditions, e.g., cardiovascular risk, cancer risk, pulmonary fibrosis risk, infectious disease risk, and risk of mortality. Abundance of telomeres also correlates with chronological age, body-mass index, hip/weight ratio, and perceived stress. One measurement of telomere length is the telomere/single copy ("T/S") ratio. Such ratios in a given population can be divided into quantiles, for example, into tertiles. It has been found that individuals with telomere abundance by T/S ratios in the lower two tertiles are at significantly higher risk for cardiovascular disease than those in the top fertile for telomere length.

In general, percentile value of measure of telomere abundance, e.g., T/S values represented as a percentage of the reference population (typically the highest fertile or quartile of telomere lengths), in a population correlates negatively with risk of disease, i.e. shorter average telomere length is associated with improved measures of health, while lower percentile scores are associated with decreased measures of health, increased disease risk or presence of telomere disease.

In a population, telomere length decreases with age. Accordingly, measures of telomere length for an individual can be compared with measures for persons in the same age range in the population, that is, an age-matched population. For example, a person at age 30 might have a measure of telomere abundance about equal to the population average for age 30, or equal to the population average for age 20 or age 40. Correlations of a measure of telomere abundance with measures of health are more accurate when compared with the measure for an age-matched population. The range for an age matched population can be, for example, one year, two years, three years, four years, 5 years, 7 years or 10 years.

5.1 Measures of Health

Short Telomere abundance determined from subject samples by the method of the present disclosure can be correlated with measures of health. Of particular interest are measures of health involving perceived stress. Telomere shortening can be accelerated by genetic and environmental factors, including multiple forms of stress such as oxidative damage, biochemical stressors, chronic inflammation and viral infections (Epel, E. S. et al., *Proc. Natl. Acad. Sci. USA,* 2004, 49:17312-15). A convenient measure of general health status is the SF-36® Health Survey developed by John Ware (see, e.g., world wide web URL sf-36.org/tools/SF36.shtml). The SF-36 is a multi-purpose, short-form health survey with only 36 questions to be posed to patients, preferably by trained individuals. It provides an 8-scale profile of functional health and well-being scores as well as psychometrically-based physical and mental health summary measures and a preference-based health utility index. The SF-36 survey is used to estimate disease burden and compare disease-specific benchmarks with general population norms. The most frequently studied diseases and conditions include arthritis, back pain, cancer, cardiovascular disease, chronic obstructive pulmonary disease, depression, diabetes, gastrointestinal disease, migraine headache, HIV/aids, hypertension, irritable bowel syndrome, kidney disease, low back pain, multiple sclerosis, musculoskeletal conditions, neuromuscular conditions, osteoarthritis, psychiatric diagnoses, rheumatoid arthritis, sleep disorders, spinal injuries, stroke, substance abuse, surgical procedures, transplantation and trauma (Turner-Bowker et al., *SF-36® Health Survey & "SF" Bibliography: Third Edition* (1988-2000), Quality-Metric Incorporated, Lincoln, R.I., 2002). One skilled in the art will appreciate that other survey methods of general health status, for example, the RAND-36, may find use in the present disclosure.

In one aspect of the present disclosure, subject samples are collected over time and measurements of short telomere abundance are determined from the samples. Appropriate time periods for collection of a plurality of samples include, but are not limited to, 1 month, 3 months, 6 months, 1 year, 2 years, 5 years and 10 years (for example, the time between the earliest and the last sample can be about these time periods). This method allows for monitoring of patient efforts to improve their general health status and/or to monitor their health status and/or disease risk. Since short telomeres trigger cell death, a finding that the percentage of short telomere length is lowered or maintained with time within an individual indicates a health improvement, while increase of percentage of short telomeres overtime represents a decrease or worsening in health.

5.2 Risk of a Pathological Condition 5.2.1 Diseases

Measuring the number of repetitive units of telomeres has a wide variety of applications in medical diagnosis, e.g., for disease risk, disease prognosis, and therapeutics. In particular, measurement of telomere length finds application in assessing pathological conditions leading to the risk of disease. In one aspect of the disclosure, the disease is one associated with aging, for example but not limited to, cardiovascular disease, diabetes, cancer, liver fibrosis, and depression.

In one aspect, the present disclosure finds use in the assessment and monitoring of cardiovascular disease. Telomere length in white blood cells has been shown to be shorter in patients with severe triple vessel coronary artery disease than it is in individuals with normal coronary arteries as determined by angiography (Samani, N. J. et al., *Lancet,* 2001, 358:472-73), and also in patients who experiencing a premature myocardial infarction before age 50 years as compared with age- and sex-matched individuals without such a history (Brouilette S. et al., *Arterioscler. Thromb. Vase. Biol.,* 2003, 23:842-46). Brouilette et al. (*Lancet,* 2007, 369:107-14) has suggested that shorter leucocyte telomeres in people prone to coronary heart disease could indicate the cumulative effect of other cardiovascular risk factors on telomere length. Increased oxidative stress also contributes to atherosclerosis, and increased oxidant stress has been shown to increase rates of telomere attrition in vitro (Harrison, D., *Can. J. Cardiol.,* 1998, 14(suppl D):30D-32D; von Zglinicki, T., *Ann. N Y. Acad. Sci.,* 2000, 908:99-110). In cross-sectional studies, smoking, body-mass index, and type 1 diabetes mellitus have also been reported to be associated with shorter leucocyte telomere length (Valdes, A., et al., *Lancet,* 2005, 366:662-64; Jeanclos, E. et al., *Diabetes,* 1998, 47:482-86). Increased life stress, a factor known to increase the risk of coronary heart disease, has been shown to be associated with shorter telomeres, possibly as a consequence of increased oxidative stress (Epel, 2004, ibid.). Thus, smokers and patients with a high body-mass index, diabetes and/or increased life stress would all benefit from determination and continued monitoring of their telomere abundance according to the method of the disclosure.

Type 2 diabetes is characterized by shorter telomeres (Salpea, K. and Humphries, S. E., *Atherosclerosis,* 2010, 209(1):35-38). Shorter telomeres have also been observed in type 1 diabetes patients (Uziel O. et al., *Exper. Gerontology,* 2007, 42:971-978). The etiology of the disease in type 1 diabetes is somewhat different from that in type 2, although in both cases, beta cell failure is the final trigger for full-blown disease. Telomere length is thus a useful marker for diabetes since it is associated with the disease's progression. Adaikalakoteswari et al. (*Atherosclerosis,* 2007, 195: 83-89) have shown that telomeres are shorter in patients with pre-diabetic impaired glucose tolerance compared to controls. In addition, telomere shortening has been linked to diabetes complications, such as diabetic nephropathy (Verzola D. et al., *Am. J. Physiol.,* 2008, 295:F1563-1573), microalbuminuria (Tentolouris, N. et al., *Diabetes Care,* 2007, 30:2909-2915), and epithelial cancers (Sampson, M. J. et al., *Diabetologia,* 2006, 49:1726-1731) while telomere shortening seems to be attenuated in patients with well-controlled diabetes (Uziel, 2007, ibid.). The method of the present disclosure is particularly useful in monitoring the status of pre-diabetic and diabetic patients to provide an early warning for these complications and others.

The present disclosure is useful for determining telomere lengths of various types of cancer cells because activation of telomerase activity is associated with immortalization of cells. While normal human somatic cells do not or only transiently express telomerase and therefore shorten their telomeres with each cell division, most human cancer cells typically express high levels of telomerase and show unlimited cell proliferation. High telomerase expression allows cells to proliferate and expand long term and therefore supports tumor growth (Roth, A. et al., in *Small Molecules in Oncology, Recent Results in Cancer Research,* U. M. Martens (ed.), Springer Verlag, 2010, pp. 221-234). Shorter telomeres are significantly associated with risk of cancer, especially cancers of the bladder and lung, smoking-related, the digestive system and the urogenital system. Excessive telomere shortening likely plays a role in accelerating tumor onset and progression (Ma H. et al., *PLo SONE,* 2011, 6(6): e20466. doi:10.1371/journal.pone.0020466). Studies have further shown that the effect of shortened telomeres on breast cancer risk is significant for certain population subgroups, such as premenopausal women and women with a poor antioxidative capacity (Shen J., et al., *Int. J. Cancer,* 2009, 124:1637-1643). In addition to the assessing and monitoring cancers in general, the present disclosure is particularly useful for the monitoring of oral cancers if genomic DNA derived from saliva samples is utilized.

Cirrhosis of the liver is characterized by increasing fibrosis of the organ often associated with significant inflammatory infiltration. Wiemann et al. (*FASEB Journal,* 2002, 16(9):935-982) have shown that telomere shortening is a disease- and age-independent sign of liver cirrhosis in humans. Telomere shortening is present in cirrhosis induced by viral hepatitis (chronic hepatitis A and B), toxic liver damage (alcoholism), autoimmunity, and cholestasis (PBC and PSC); telomeres are uniformly short in cirrhosis independent of the age of the patients. Telomere shortening and senescence specifically affect hepatocytes in the cirrhotic liver and both parameters strongly correlate with progression of fibrosis during cirrhosis. Thus, the method of the present disclosure finds use in diagnosing and monitoring liver fibrosis.

Depression has been likened to a state of "accelerated aging," and depressed individuals have a higher incidence of various diseases of aging, such as cardiovascular and cerebrovascular diseases, metabolic syndrome, and dementia. People with recurrent depressions or those exposed to chronic stress exhibit shorter telomeres in white blood cells. Shorter telomere length is associated with both recurrent depression and cortisol levels indicative of exposure to chronic stress (Wikgren, M. et al., *Biol. Psych.,* 2011, DOI: 10.1016/j.biopsych.2011.09.015). However, not all depressed individuals show shortened telomeres equally because of a large variance in depressive episodes over a lifetime. Those who suffered from depression for long durations have significantly shorter telomeres due to longer exposure to oxidative stress and inflammation induced by psychological stress when compared with control populations (Wolkowitz et al., *PLos One,* 2011, 6(3):e17837). Thus, the method of the present disclosure may find use in monitoring depression.

Chronic Infection

Abnormal telomere length is associated with chronic infection including HIV (Effros R B et al, AIDS. 1996 July; 10(8):F17-22, Pommier et al Virology. 1997, 231(1):148-54), and HBV, HCV and CMV (Telomere/telomerase dynamics within the human immune system: effect of chronic infection and stress. (Effros R B, Exp Gerontol. 2011 February-March; 46(2-3):135-40. Rejuvenation Res. 2011 February; 14(1):45-56. doi: 10.1089rej.2010.1085. Epub 2010 Sep. 7.)

In Harley et al. ("A natural product telomerase activator as part of a health maintenance program", Harley C B, Liu W, Blasco M, Vera E, Andrews W H, Briggs L A, Raffaele J M, Rejuvenation Res. 2011 February; 14(1):45-56), it was found that individuals who were CMV seropositive had shorter telomeres than those who were CMV negative, and moreover, the CMV positive subjects were more likely to respond to a nutritional supplement program of TA-65, a natural product-derived telomerase activator along with other supplements, in reducing the abundance of senescent CD8+/CD28− cells, suggesting a companion diagnostics application for measuring average telomere length or abundance of short telomeres, in conjunction with administration of telomerase activators.

Measurement of short telomere population can be used as indicator of prognosis disease progression and treatment outcome.

One study reported that telomere length in CD4+ cells is related to inflammatory grade, fibrosis stage, laboratory indices of severity, subsequent hepatic decompensation and treatment outcome in patients with chronic HCV infection (Hoare et al, *J. Hepatol.,* 2010, 53(2):252-260).

In another report, longer leukocyte telomere length predicts increased risk of hepatitis B virus-related hepatocellular carcinoma (Liu et al, 2011, 117(18):4247-56.)

In the case of HIV, telomere shortening is caused by viral infection. In addition, the nucleoside analog reverse-transcriptase inhibitors used to treat HIV are telomerase inhibitors (Strahl and Blackburn, *Mol Cell Biol.,* 1996, 16(1):53-65; Hukezalie et al, *PLoS One,* 2012, 7(11):e47505). Measurement of short telomere abundance might help determine the side effects and efficacy of HAART treatment.

5.2.2 Other Pathological Conditions

The present disclosure also finds use in diagnosis of diseases related to early onset of aging. For example, individuals with Hutchinson Gilford progeria disease show premature aging and reduction in proliferative potential in fibroblasts associated with loss of telomeric length (Allsopp, R. C. et al, *Proc. Natl. Acad. Sci. USA,* 1992, 89:10114-10118). Amplification and quantitation of the number of telomeric repeats according to the method of this disclosure is useful for determining disease risk or prognosis and taking appropriate interventional steps as described above.

5.3 Telomere Diseases

In one aspect of the present disclosure, both the presence and the progress of telomeric-specific diseases may be determined using samples. Telomere diseases are associated with an abnormal or premature shortening of telomeres, which can, for example, result from defects in telomerase activity. Telomerase is a ribonucleoprotein complex required for the replication and protection of telomeric DNA in eukaryotes. Cells lacking telomerase undergo a progressive loss of telomeric DNA that results in loss of viability and a concomitant increase in genome instability. These diseases may be inherited and include certain forms of congenital aplastic anemia, in which insufficient cell divisions in the stem cells of the bone marrow lead to severe anemia. Certain inherited diseases of the skin and the lungs are also caused by telomerase defects. For telomere diseases, a threshold for T/S<0.5 is appropriate for some conditions. Also, a commonly used metric is an age-adjusted percentile telomere score less than <10% or preferably <1% relative to a normal population.

Dyskeratosis congenita (DKC), also known as Zinsser-Engman-Cole syndrome, is a rare, progressive bone marrow failure syndrome characterized by mucocutaneous abnormalities: reticulated skin hyperpigmentation, nail dystrophy, and oral leukoplakia (Jyonouchi S. et al., *Pediatr. Allergy Immunol.,* 2011, 22(3):313-9; Bessler M., et al., *Haematologica,* 2007, 92(8):1009-12). Evidence exists for telomerase dysfunction, ribosome deficiency, and protein synthesis dysfunction in this disorder. Early mortality is often associated with bone marrow failure, infections, fatal pulmonary complications, or malignancy. The disease is inherited in one of three types: autosomal dominant, autosomal recessive, or the most common form, X-linked recessive (where the gene responsible for DC is carried on the X-chromosome). Early diagnosis and measurement of disease progress using the method of this disclosure is very beneficial for families with these genetic characteristics so that early treatment with anabolic steroids or bone-marrow-stimulating drugs can help prevent bone marrow failure. The non-invasive, patient friendly saliva-testing method of the present disclosure is particularly useful for DKC because babies and small children need testing and continued monitoring.

Idiopathic interstitial pneumonias are characterized by damage to the lung parenchyma by a combination of fibrosis and inflammation. Idiopathic pulmonary fibrosis (IPF) is an example of these diseases that causes progressive scarring of the lungs. Fibrous scar tissue builds up in the lungs over time, affecting their ability to provide the body with enough oxygen. Heterozygous mutations in the coding regions of the telomerase genes, TERT and TERC, have been found in familial and sporadic cases of idiopathic interstitial pneumonia. All affected patients with mutations have short telomeres. A significant fraction of individuals with IPF have short telomere lengths that cannot be explained by coding mutations in telomerase (Cronkhite, J. T., et al., *Am. J. Resp. Crit. Care Med.,* 2008, 178:729-737). Thus, telomere shortening can be used as a marker for an increased predisposition toward this age-associated disease (Alder, J. K., et al., *Proc. Natl. Acad. Sci. USA,* 2008, 105(35):13051-13056). Further, the course of IPF varies from person to person. For some, the disease may progress slowly and gradually over years, while for others it may progress rapidly. The method of the present may be conveniently used to monitor the course of pulmonary fibrosis and taking appropriate interventional steps as described above.

Aplastic anemia is a disease in which bone marrow stops making enough red blood cells, white blood cells and platelets for the body. Any blood cells that the marrow does make are normal, but there are not enough of them. Aplastic anemia can be moderate, severe or very severe. People with severe or very severe aplastic anemia are at risk for life-threatening infections or bleeding. Patients with aplastic anemia carrying telomerase mutations have an increased risk of developing myelodysplasia. Telomerase deficiency may cause variable degrees of telomere shortening in hematopoietic stem cells and lead to chromosomal instability and malignant transformation (Calado, R. T. and Young, N. S., *The Hematologist,* 2010 world wide web URL hematology-.org/Publications/Hematologist/2010/4849.aspx). Aplastic anemia patients with shorter telomeres have a lower survival rate and are much more likely to relapse after immunotherapy than those with longer telomeres. Scheinberg et al. (*JAMA,* 2010, 304(12):1358-1364) found that relapse rates dropped as telomere lengths increased. The group of patients with the shortest telomeres was also at greater risk for a conversion to bone marrow cancer and had the lowest overall survival rates. The method of the present disclosure can be used in aplastic anemia patients to monitor the risk of developing major complications so that the clinical management of an individual may be tailored accordingly.

5.4 Drug Responsiveness

In another aspect, the present disclosure is useful in monitoring effectiveness of therapeutics or in screening for drug candidates affecting telomere length or telomerase activity. The ability to monitor telomere characteristics can provide a window for examining the effectiveness of particular therapies and pharmacological agents. The drug responsiveness of a disease state to a particular therapy in an individual may be determined by the method of the present disclosure. For example, the present disclosure finds use in monitoring the effectiveness of cancer therapy since the proliferative potential of cells is related to the maintenance of telomere integrity. As described above, while normal human somatic cells do not or only transiently express telomerase and therefore shorten their telomeres with each cell division, most human cancer cells typically express high levels of telomerase and show unlimited cell proliferation. Roth et al., (ibid., 2010) have suggested that individuals with cancer who have very short telomeres in their tumors (in which the shortest telomeres in most cells are near to telomere dysfunction) and high telomerase activity might benefit the most from anti-cancer telomerase-inhibiting drugs. Because telomerase is either not expressed or expressed transiently and at very low levels in most normal cells, telomerase inhibition therapies may be less toxic to normal cells than conventional chemotherapy. An example of such drugs is the short oligonucleotide-based telomerase inhibitor imetelstat (previously named GRN163L). Imetelstat is a novel lipid-based conjugate of the first-generation oligonucleotide GRN163 (Asai, A. et al., *Cancer Res.,* 2003, 63:3931-3939). However, cancer patients having very short telomeres in normal blood cells (particularly their granulocytes) are at higher risk of adverse effects of imetelstat on proliferative tissues such as the bone marrow. Rattain et al. (2008) found that such subjects with short granulocyte telomere length were more likely to have bone marrow failure symptoms such as neutropenia or thrombocytopenia. In this situation, a doctor might prescribe a lower dose of imetelstat, a different drug, or more frequent monitoring for bone marrow problems.

In other aspects, drug efficacy in the treatment of diseases of aging, for example but not limited to, cardiovascular disease, diabetes, pulmonary fibrosis, liver fibrosis, interstitial pneumonia and depression. In the case of cardiovascular disease, Brouilette et al. reported that middle-aged men with shorter telomere lengths than control groups benefit the most from lipid-lowering therapy with pravastatin (Brouilette, S. W. et al., *Lancet,* 2007, 369:107-114). Satoh et al. (*Clin. Sci.,* 2009, 116:827-835) indicating that intensive lipid-lowering therapy protected telomeres from erosion better in patients treated with atorvastatin when compared with patients treated with moderate pravastatin therapy. The method of the present disclosure can be used to monitor the efficacy of statins in treated patients, wherein shorter telomere length correlates with better drug efficacy. Since subjects with the longest telomeres did not on average benefit from prophylactic statins, a doctor might suggest that the patient be especially compliant with good lifestyle habits as part of their treatment program. Conversely, patients with short telomeres who fear side effects of chronic statin usage might be persuaded to take statins based on their higher probability of benefiting from statins. Examples of statins that can be used include niacin (ADVICOR, SIMCOR), lovastatin (ALTOPREV, MEVACOR), amolopidine (CADUET), rosuvastatin (CRESTOR), sitagliptin/simvastatin (JUVISYNC), fluvastatin (LESCOL), pravastatin (PRAVACHOL), atorvastatin (LIPITOR), pitavastatin (LIVALO), and ezetimibe/simvastatin (VYTORIN).

In further aspects, drug effectiveness in the treatment of telomeric diseases, for example but not limited to, Dyskeratosis congenita, pulmonary fibrosis, and aplastic anemia, may be measured. For example, dyskeratosis congenita and pulmonary fibrosis are both treated with high-dose steroids, which are well known to have numerous deleterious side effects. Use of the lowest possible steroid dose is thus highly desirable, making the method of the present disclosure a valuable tool for monitoring these patients.

5.5 Drug Candidate Screening

In another aspect, the present disclosure finds use as a general method of screening for candidate drugs, dietary supplements, and other interventions including lifestyle changes which affect biological pathways regulating telomere length, such as telomerase activity. Ability to rapidly and specifically amplify telomere repeats in a quantitative manner provides a high throughput screening method for identifying small molecules, candidate nucleic acids, and peptides agents and other products or interventions affecting telomere dynamics in a cell. Drug or other product candidates that have a positive, telomere lengthening effect on normal cells would be preferred in the treatment of degenerative, or cell senescence related conditions over those with telomere shortening (or telomerase inhibiting) effects, everything else being equal. In the case of treatment of cancer, drugs that have a negative, telomere shortening effect, especially in cancer cells would be preferred.

EXAMPLES

Example 1—Amplification of Short Telomere Sequences

Here we describe a quantitative PCR based method using purified genomic DNA to measure percentage of short telomeres. This method incorporates non-covalent binding of a non-human primer 'TeloPrimer' to the 3'-overhang of vertebrate genomic DNA, time-controlled extension of the TeloPrimer towards a subtelomere unique sequence 'SUS' with an enzyme that displaces or degrades the C-strand of the telomere during the extension reaction, followed by an amplification reaction utilizing SUS and the non-human sequence portion of TeloPrimer. Only telomeres that are short enough such that the extended TeloPrimer product reaches the SUS sequence are amplified. The controlled timing of the strand displacement reaction thus allows detection of telomeres shorter than a specified threshold of telomere length. In addition, by controlling the extension time in the PCR step by SUS and TeloAnchor primers, the short telomere population will be selectively amplified, further increasing the specificity of this assay to measure short telomeres. The abundance of short telomeres is quantified in the T-run of TeloTest.

Materials and Methods
Primers
All primers were purchased from Integrated DNA Technologies in standard desalted or HPLC purified form. Sequences of the primers are listed below:

```
TeloPrimer:
5'-TGCTCGGCCGATCTGGCATCCCTAACC-3'    [SEQ ID NO: 7]

TeloAnchor:
5'-TGCTCGGCCGATCTGGCATC-3'           [SEQ ID NO: 8]

SUS (HPLC purified):
5'-GATGGATCCTGAGGGTGAGGGTGAGGG-3'    [SEQ ID NO: 2]

TeloProbe (HPLC purified):
5'-CCCTAACCCTAACCCTAACCCTAA-3'       [SEQ ID NO: 9]
```

Annealing of TeloPrimer to Genomic DNA
Human genomic DNA was mixed with TeloPrimer at final concentration of 20 ng/ul DNA and 1 uM TeloPrimer in a 50 ul reaction, incubated at 65° C. for 10 min in a heating block and then cooled down to room temperature over the period of one hour. The annealed samples are kept on ice until strand displacement reaction.

Strand Displacement
Strand displacement reaction was carried out in 5 ul volume, with 50 ng of the annealed DNA, 40 mM Tris-HCl, pH 8.0, 10 mM MgCl2, 50 mM NaCl, 5 mM DTT (PN 70726, Affymetrix, Santa Clara, Calif., USA), 100 ug/ml BSA (Cat #B9001S, New England Biolabs, Ipswich, Mass.), 500 uM dNTP (Cat #1708874, Bio-Rad, Hercules, Calif.), 5 uM Single Strand Binding protein (SSB, Cat #70032Y 100 UG, Affymetrix, Santa Clara, Calif.) and 400 nM Sequenase 2.0 (cat #70775Y 200 UN, Affymetrix, Santa Clara, Calif.) (Concentration of Sequenase is 13 U/ul). The mixture without Sequenase 2.0 is pre-warmed at 37° C. for one minute, and then incubated at 37° C. for 30 sec to 10 min after sequence 2.0 was added to the mixture. The reaction is stopped by heat inactivation at 80° C. for 20 min.

PCR Amplification of Strand Displacement Product
The product from the strand displacement DNA reaction was diluted 50-fold in DNA suspension buffer (Cat #T0227, Teknova, Hollister, Calif.). PCR was carried out in 40 ul reaction volume that contains 1.5 mM MgCl2, 300 uM dNTP (Cat #1708874, Bio-Rad, Hercules, Calif.), 0.5 uM SUS primer, 0.5 uM TeloAnchor primer, 2 ul diluted DNA, 5 units PLATINUM Taq polymerase (Cat #10966-083, Life Technologies, Grand Island, N.Y.).

The cycling program is as the following: 2 min at 94° C., 35 cycles of 15 sec at 94° C., 30 sec at 65° C., 30 seconds to 10 mM at 72° C., followed by 10 min extension at 72° C. The PCR reaction is carried in a Bio-Rad C1000 Thermocycler (Bio-Rad, Hercules, Calif.).

Quantification of Amplified PCR Product by TeloTest
PCR products were diluted 10 to 1000 fold in DNA suspension buffer. The T-run of TELOTEST was used to quantify the PCR products. PCR fragments containing between 60-600 bp perfect telomere repeats are used as standard to calculate DNA concentration of each sample. An internal standard of ~2 kb DNA fragment with TTAGGG 3' overhang and SUS sequence near 5' will be included in each sample from displacement reaction to qPCR steps. Reaction efficiency of each sample will be estimated by qPCR of a non-human sequence within the internal standard. A normalizing factor for each sample will be generated based on the reaction efficiency.

Southern Blot
Southern blot analysis was carried out to confirm the size of displaced telomere DNA. Strand displacement products amplified by SUS and TeloAnchor primers were run on a 0.5% agarose gel, transferred to a positively charged Nylon membrane and hybridized overnight at 37° C. to a DIG labeled oligo probe with four TTAGGG repeats. Chemiluminescent detection was used for signal detection.

Results
Overall Scheme
The short telomere assay (STA) described here quantifies the amount of short telomeres in human genomic DNA samples by strand-displacement or strand degradation followed by quantitative PCR. The overall scheme of the assay is illustrated in FIG. 1.

The assay is carried out by first annealing TeloPrimer to human genomic DNA. TeloPrimer contains 19 nucleotide of non-human sequence at the 5' end and 8 nucleotides of telomeric sequence at the 3' end. Using native genomic DNA ensures that TeloPrimer will only anneal to the 3' single-strand tail (overhang) of telomeres, not the double strand region. Extension of the TeloPrimer is achieved by a strand displacement or strand degradation reaction. With limited time, the reaction will only be able to reach to the telomere variance region on those chromosomes with short telomeres, while on the chromosomes with long telomeres, the strand-displaced products will stop within the perfect telomere repeat region. Displaced short telomeres are then enriched by PCR with SUS primer and TeloAnchor primer. SUS primer contains 3 repeats of the TGAGGG sequence that are found on most chromosomes in the telomeric variant region, at or near the junction between the subtelomeric region and true telomere repeats. TeloAnchor primer shares the same non-human sequence as TeloPrimer and does not contain telomere sequence. The pair of SUS and TeloAnchor is designed to specifically amplify the strand-displaced short telomeres. Finally, TELOTEST T-run is used to quantify the amount of short telomeres.

Quantification of Strand Displacement Products

Strand displacement amplification is a DNA synthesis reaction where the downstream DNA encountered is displaced by the polymerase during synthesis. Many protocols including whole genome amplification and forensic analysis use strand displacement to amplify minute quantities of template DNA. Because of the strand-displacing activity of the DNA polymerase, DNA with nicks or single strand tails can be used as templates without a denaturation step. We chose to use a strand-displacing enzyme in our experimental design because the single-strand tail of telomeres serves as a natural template for strand-displacing enzymes and is less likely than a 5'-3' exonuclease (degradative enzyme) to create gaps in genome that might cause non-specific amplification of interstial telomere-like sequences. Annealing of TELOPRIMER to the single-strand tails of telomeres on native genomic DNA places TeloPrimer adjacent to the 5' end of the C-strand (FIG. 1). In this design, the length of strand-displaced products will accurately reflect the length of the telomeres. By controlling the strand-displacement time, the reaction will only be able to reach to the telomere variance region on those chromosomes with short telomeres. We chose to use Sequenase 2.0, a genetically engineered form of T7 DNA polymerase with no exonuclease activity, because it is reported to synthesize DNA on a linear template with high specificity and processivity (Joneja, A. and X. Huang, Anal Biochem, 2011. 414(1) 58-69). We performed a time course experiment where the strand displacement reaction took from 30 seconds to 5 minutes. Genomic DNA from the bladder cancer cell line UM-UC3 was annealed to TeloPrimer and strand-displacement reaction was performed as detailed in Materials and Methods.

Figure 2:
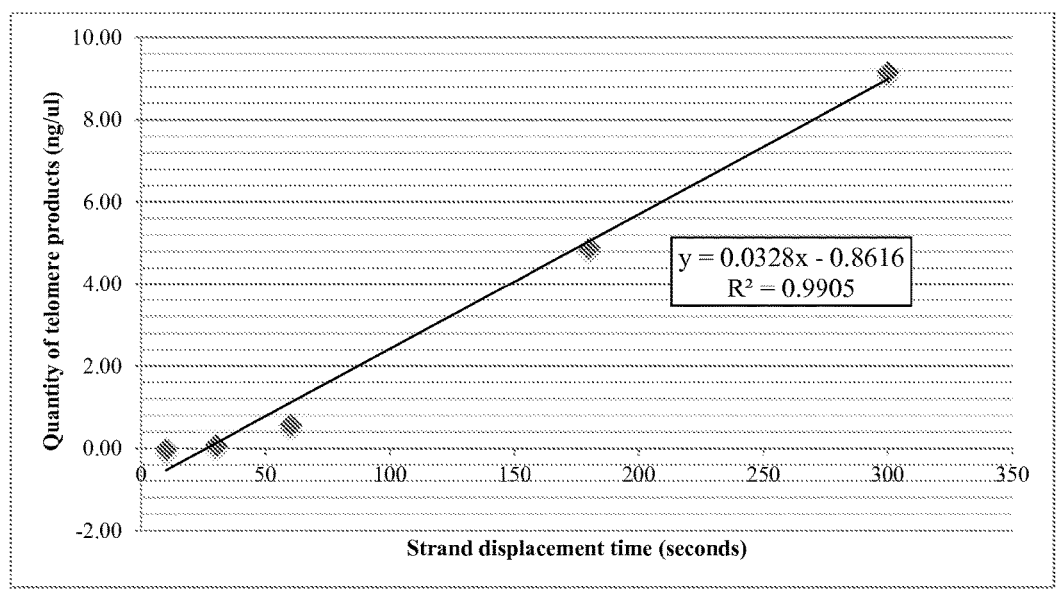
FIG. 2 shows confirmation of short telomere amplification during strand displacement by TELOTEST, a test for measuring average telomere length that uses mismatched primers that hybridize to telomeric repeat sequences in a qPCR assay. An assay of similar type is described in U.S. Pat. No. 7,695,904 (Cawthon).

FIG. 2 showed increased telomere products measured by T-run of TELOTEST qPCR with increased strand displacement reaction time. The linear regression line showed a strong relationship between time abundance of the amplicon ($R^2=0.99$). Furthermore, in the negative control, where no Sequenase 2.0 was added, no PCR product was detected in the TELOTEST T-run (Crossing point (Cp)=25, calculated concentration=1.85E-07) which is 159-fold lower than the lowest measured concentration of the reactions containing Sequenase 2.0. A parallel reaction using the single copy gene (beta-globin) primers in the TELOTEST S-run also showed no amplification product, further confirming that the telomeric products measured in T-run are derived from the strand-displacement reaction, not from total genomic DNA.

Figure 3:
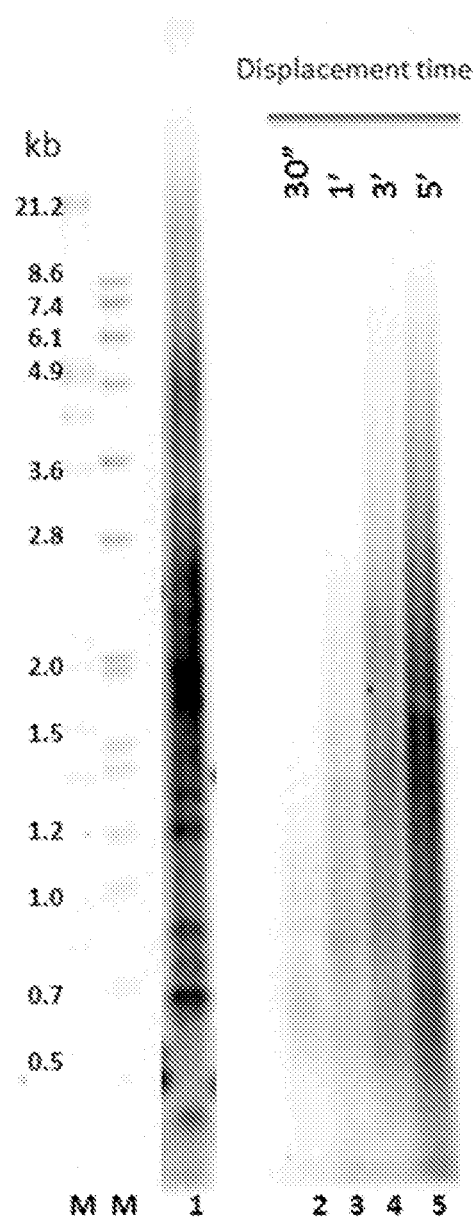
FIG. 3 shows Southern blot analysis of strand-displacement products. M: molecular weight markers; Lane 1: total genomic DNA from the bladder cancer cell-line, UM-UC3, amplified by modified STELA (Single Telomere Elongation Length Analysis) protocol (Baird et al., 2003); Lanes 2-5: PCR products using SUS and TeloAnchor as primers and the strand-displacement products are template. Strand displacement reaction times are indicated (30 seconds, 1, 3, and 5 minutes). Strand lengths are: 30 sec=~1 kb; 1 minute=~2 kb; 3 minutes=~5 kb; 5 minutes=~8 kb.

The experimental design we propose here predicted that with short displacement reaction time, only products from short telomeres will be amplified with SUS and TeloAnchor primers. We sought to confirm this by Southern blot analysis. Strand displacement products amplified by SUS and TeloAnchor primers were run on a 0.5% agarose gel, transferred to a positively charged Nylon membrane and hybridized to a DIG labeled oligo probe with four TTAGGG repeats. FIG. 3 shows that the length of the amplified PCR products increases with increasing strand displacement time. The estimated modes (peak of intensity) of the PCR products are approximately 0.6 kb, 0.9 kb. 1.2 and 1.4 kb with 0.5 minute, 1 minute, 3 minute and 5 minute displacement time respectively. With 1 minute displacement time, the majority of the products are below 2 kb. In an independent comparison test, we used a modified single telomere elongation length analysis (STELA) (Baird, D. M., et al., Nat Genet., 2003. 33(2) 203-7) protocol to analyze the telomere length profile of the total genomic DNA from the same cancer cell line UM-UC3. TeloPrimer was ligated to the 5' end of the C strand and XpYpE2 and TeloAnchor primers were used to amplify telomeres. The PCR product was run on the gel (lane 1 in FIG. 3). This revealed that the mode of UM-UC3 telomeres is around 1.8 kb, consistent with previous reports (Xu, L. and E. H. Blackburn, Mol Cell, 2007. 28(2) 315-27).

Figure 4:
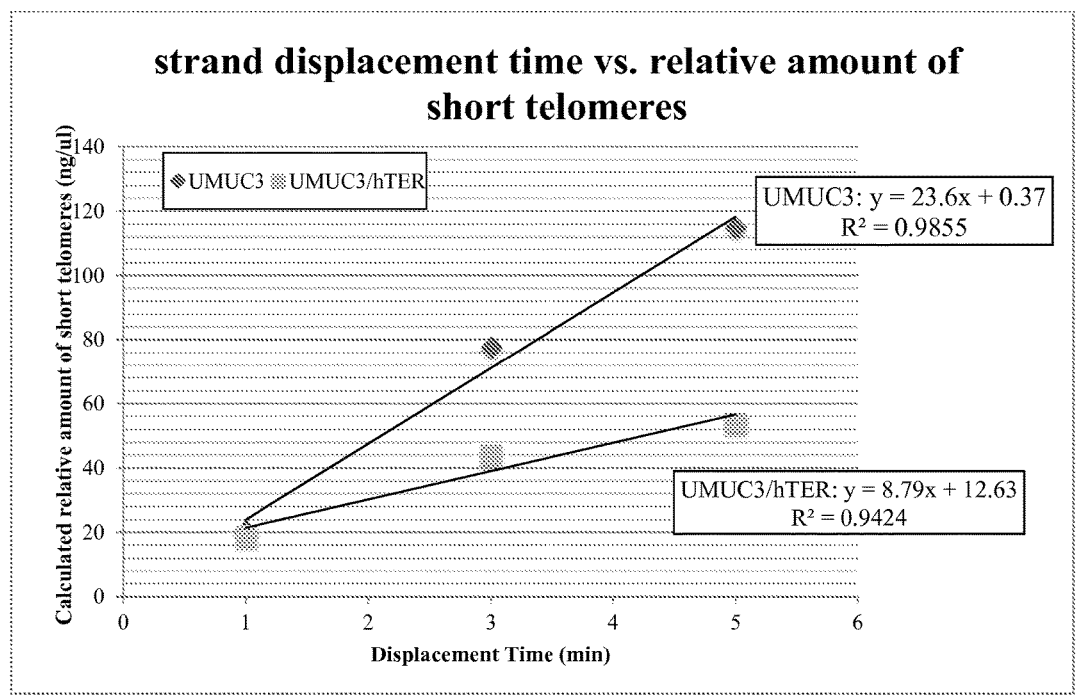
FIG. 4 shows a proof-of-concept calculation for short telomere quantification in DNA samples with different average telomere length. UM-UC3 is a cell population with short average telomeres, and UM-UC3/hTER is the identical cell population but with extended (elongated) telomeres due to over-expression of telomerase (with hTER). As shown, the relative abundance of short telomeres is much greater in UM-UC3 than in UM-UC3/hTER.
Figure 7A:
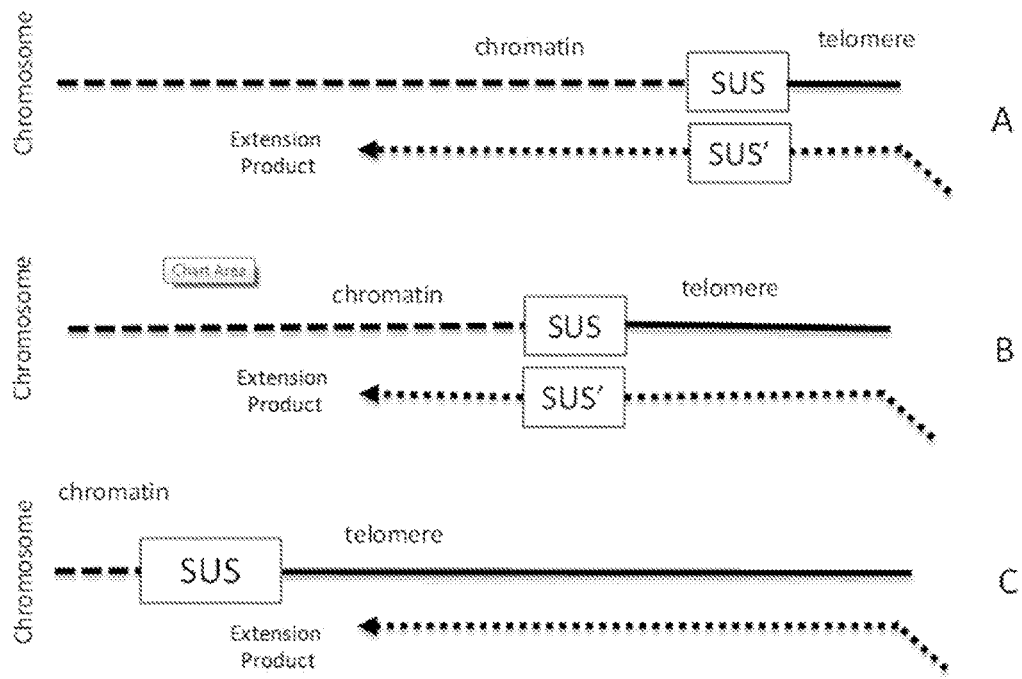
FIG. 7A and FIG. 7B show time-controlled primer extension on chromosomes A, B and C, each having telomeres of different length. Chromatin is represented by dashed line. The subtelomeric unique sequence is represented by "SUS". Telomeres are represented by the solid line. The extension product is represented by the dashed line.
Figure 7B:
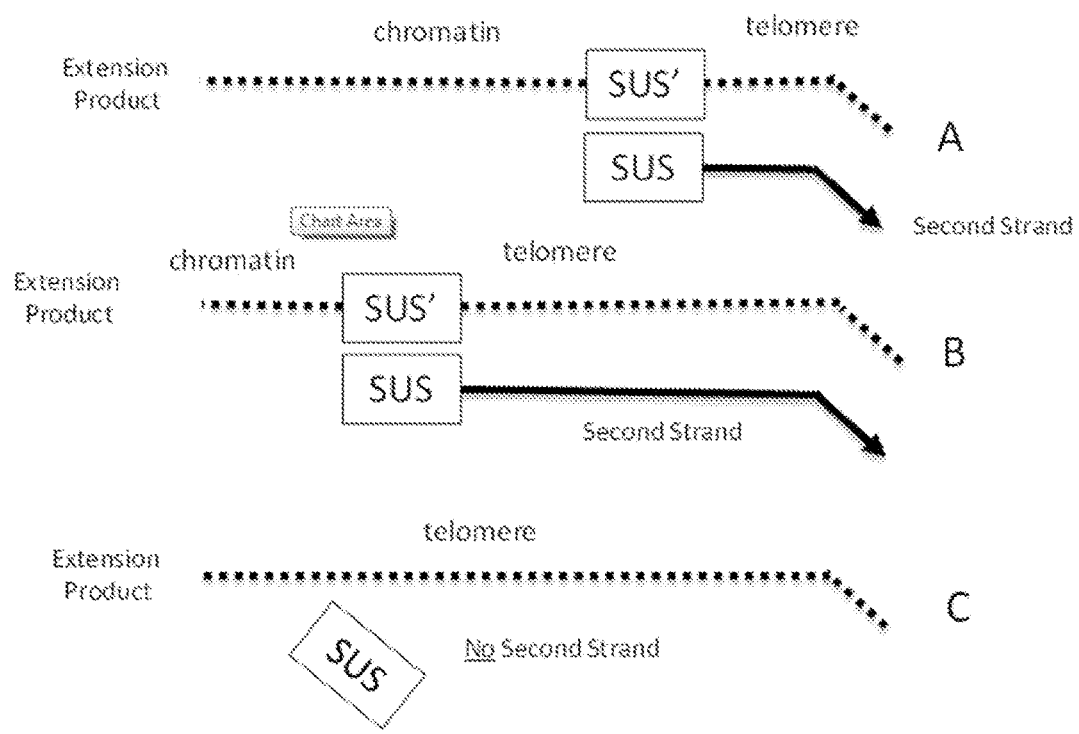

To further validate the short telomere assay, we carried out this assay with two different genomic DNA samples. In addition to the UM-UC3 DNA, we used genomic DNA from UM-UC3 infected by a lentivirus vector that expresses the RNA gene of telomerase hTER, resulting in extension of telomeres (Xu, L. and E. H. Blackburn, Mol Cell, 2007. 28(2) 315-27). The average telomere length measured by qPCR in UM-UC3/hTER is 2.1 compared to 0.56 for UM-UC3 (Telome Health Inc. data). UM-UC3/hTER cells have a lower percentage of short telomeres, as judged by Southern blot analysis (FIG. 5). Consistent with this, the calculated amount of short telomeres in UM-UC3 is 3-fold higher compared to UM-UC3/hTER (FIG. 4).

We conclude that the short telomere assay specifically measures the relative percentage of short telomeres. Furthermore, by controlling the strand displacement reaction time, the telomere length cutoff that will be measured in this assay can be varied and predetermined.

The above mentioned short telomere assay can be easily adapted to a high-throughput automated format. FIG. 6 shows individual steps in such a format.

While preferred aspects of the present invention have been shown and described herein, it will be obvious to those skilled in the art that such aspects are provided by way of example only. Numerous variations, changes, and substitutions will now occur to those skilled in the art without departing from the disclosure. It should be understood that various alternatives to the aspects of the invention described herein may be employed in practicing the invention. It is intended that the following claims define the scope of the invention and that methods and structures within the scope of these claims and their equivalents be covered thereby.

What is claimed is:

1. A method of amplifying telomeric repeat sequences and sub-telomeric sequences of a chromosome comprising:
   a) making a nucleic acid extension product by:
      i) hybridizing an extension primer to a telomeric repeat sequence in a 3' overhang of double stranded chromosomal DNA, wherein:
         (1) the double stranded chromosomal DNA has a telomeric region comprising telomeric repeat sequences and a sub-telomeric region comprising sub-telomeric sequences; and
         (2) the extension primer comprises:
            (A) a 3' portion that hybridizes to a telomeric repeat sequence in the 3' overhang under annealing conditions, and
            (B) a 5' portion having an anchor sequence that does not hybridize to a telomeric repeat sequence in the 3' overhang under the annealing conditions; and
      ii) performing a time-controlled strand displacement extension reaction to extend the extension primer towards the sub-telomeric region of the double stranded chromosomal DNA, wherein the extension reaction is timed to produce an extension product comprising both telomeric repeat sequences and sub-telomeric sequences only from double stranded chromosomal DNA having a telomeric region within a pre-determined length range; and
   b) amplifying by means of a subsequent PCR reaction sequences of the extension product; thereby producing a length-limited amplification product comprising nucleic acids having telomeric repeat sequences and sub-telomeric sequences,
   wherein the time-controlled extension reaction is timed to produce a length-limited extension product,
   wherein the time-controlled extension reaction is timed to be 0.1-30 minutes, 0.1-30 minutes, 0.1-5 minutes, 0.1-4 minutes, 0.1-3 minutes, 0.1-2 minutes, 0.1-1 minute or 0.1-0.5 minutes.

2. The method of claim 1, wherein the sequences are amplified using:
   (1) a first amplification primer that hybridizes to a sequence unique to the sub-telomeric region in the extension product under annealing conditions; and
   (2) a second amplification primer that hybridizes to the anchor sequence under the annealing conditions.

3. The method of claim 2, wherein the first amplification primer comprises the sequence

[SEQ ID NO: 10]
   5'-CGGGCCGGCTGAGGGTACCGCGA-3' (chromosome 1),

[SEQ ID NO: 11]
   5'-GCTAATGCACTCCCTCAATAC-3' (chromosome 5),
   or

[SEQ ID NO: 12]
   5'-CATTCCTAATGCACACATGATACC-3' (Chromosome 9).

4. The method of claim 2, wherein the first amplification primer comprises the sequence 5'-GATGGATCCT-GAGGGTGAGGGTGAGGG-3' [SEQ ID NO: 2] and the second primer comprises the sequence 5'-TGCTCGGC-CGATCTGGCATC-3' [SEQ ID NO: 8].

5. The method of claim 1, wherein the length range of the amplified telomere products can be determined by using a time-controlled extension time in the PCR reaction.

6. The method of claim 1, further comprising co-amplifying a control sequence.

7. The method of claim 6, wherein the control sequence comprises a plurality of non-telomeric repeat sequences.

8. A method for determining short telomere abundance comprising:
   a) providing a sample comprising double-stranded chromosomal DNA comprising a 3' overhang from a subject;
   b) producing a length-limited amplification product from the double-stranded chromosomal DNA using the method of claim 1; and
   c) determining short telomere abundance from the length-limited amplified product.

9. The method of claim 8, further comprising:
   d) comparing the short telomere abundance with a measure of total telomere abundance from the sample.

10. The method of claim 9, wherein step d) comprises determining short telomere abundance as a function of total telomere abundance.

11. The method of claim 8, wherein determining short telomere abundance is performed using qPCR.

12. The method of claim 11, wherein qPCR is performed using a first and a second primer,
   i) wherein said first primer hybridizes to at least one repetitive unit of said first strand and said second primer hybridizes to at least one repetitive unit of said second strand,
   ii) wherein said hybridized primers are capable of primer extension when hybridized to their respective strands, and wherein at least one nucleotide of said first primer produces an internal base pair mismatch between said first primer and a nucleotide of said repetitive unit when said first primer is hybridized to at least one repetitive unit of said first strand,
   iii) wherein said first primer also produces a mismatch with the 3' terminal nucleotide of said second primer when first and second primers hybridize to each other,
   iv) wherein at least one nucleotide of said second primer produces an internal base pair mismatch between said second primer and a nucleotide of said repetitive unit when said second primer is hybridized to at least one repetitive unit of said second strand.

13. The method of claim 8, wherein determining short telomere abundance comprises measuring average telomere length in the sample by Southern blot, dot blot, slot blot, immunochemistry, nucleic acid sequencing, or digital PCR.

14. The method of claim 8, wherein the short telomere abundance is a measure of relative abundance.

15. The method of claim 9, wherein the total telomere abundance is measured relative to abundance of a genomic reference sequence.

16. The method of claim 15, wherein the genomic reference sequence comprises a single copy reference nucleotide sequence or a non-telomere repetitive DNA sequence.

17. The method of claim 16, wherein the single copy reference nucleotide sequence is human beta-globin.

18. A method comprising:
   a) obtaining a sample from a subject;
   b) determining short telomere abundance using the method of claim 8; and
   c) correlating short telomere abundance with a condition or disease.

19. The method of claim 18, wherein the measure of short telomere abundance is determined by comparing short telomere abundance with total telomere abundance from the sample.

20. The method of claim 18, wherein the condition or disease is mortality risk.

21. The method of claim 18, wherein the telomere abundance is absolute abundance.

22. The method of claim 21, wherein the absolute abundance is measured as length of telomeric sequences.

23. The method of claim 18, wherein the condition is a risk of disease.

24. The method of claim 23, wherein the risk of disease is an age-associated disease.

25. The method of claim 24, wherein the age-associated disease is cardiovascular disease; and wherein a measure lower than average in a population correlates with increased risk of cardiovascular disease.

26. The method of claim 18, further comprising providing the subject with a diagnosis or a prognosis based on the correlation.

27. The method of claim 18, further comprising treating the subject based on the correlation.

28. A method comprising:
    a) obtaining a plurality of samples from a subject; wherein the samples are taken over a period of time; and wherein each sample is obtained at a different time;
    b) determining short telomere abundance in each of the plurality of samples using the method of claim 8;
    c) determining a rate of change in the measures of short telomere abundance; and
    d) correlating the rate of change with: (1) a measure of health; (2) a risk of a pathological condition; (3) a telomeric disease or (4) drug responsiveness.

29. The method of claim 28, wherein the short telomere abundance is determined by comparing the short telomere abundance with total telomere abundance from the sample.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 1
gttgtctcag ggtcctagtg                                          20
```

<210> SEQ ID NO 2
<211> LENGTH: 27
<212> TYPE: DNA
<213> ORGANISM: Artificial Sequence
<220> FEATURE:
<223> OTHER INFORMATION: synthetic construct; primer

<400> SEQUENCE: 2
gatggatcct gagggtgagg gtgaggg                                        27

<210> SEQ ID NO 3
<211> LENGTH: 37
<212> TYPE: DNA
<213> ORGANISM: Artificial Sequence
<220> FEATURE:
<223> OTHER INFORMATION: synthetic construct; primer

<400> SEQUENCE: 3 ggttttgag ggtgagggtg agggtgaggg tgagggt                              37

<210> SEQ ID NO 4
<211> LENGTH: 39
<212> TYPE: DNA
<213> ORGANISM: Artificial Sequence
<220> FEATURE:
<223> OTHER INFORMATION: synthetic construct; primer

<400> SEQUENCE: 4
tcccgactat ccctatccct atccctatcc ctatcccta                           39

<210> SEQ ID NO 5
<211> LENGTH: 39
<212> TYPE: DNA
<213> ORGANISM: Artificial Sequence
<220> FEATURE:
<223> OTHER INFORMATION: synthetic construct; primer

<400> SEQUENCE: 5
cggtttgttt gggtttgggt tgggtttgg gtttgggtt                            39

<210> SEQ ID NO 6
<211> LENGTH: 39
<212> TYPE: DNA
<213> ORGANISM: Artificial Sequence
<220> FEATURE:
<223> OTHER INFORMATION: synthetic construct; primer

<400> SEQUENCE: 6
ggcttgcctt acccttaccc ttaccttac ccttaccct                            39

<210> SEQ ID NO 7
<211> LENGTH: 27
<212> TYPE: DNA
<213> ORGANISM: Artificial Sequence
<220> FEATURE:
<223> OTHER INFORMATION: synthetic construct; primer

<400> SEQUENCE: 7
tgctcggccg atctggcatc cctaacc                                        27

<210> SEQ ID NO 8
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 8
tgctcggccg atctggcatc                                         20

<210> SEQ ID NO 9
<211> LENGTH: 24
<212> TYPE: DNA
<213> ORGANISM: Artificial Sequence
<220> FEATURE:
<223> OTHER INFORMATION: synthetic construct; primer

<400> SEQUENCE: 9
ccctaaccct aaccctaacc ctaa                                    24

<210> SEQ ID NO 10
<211> LENGTH: 23
<212> TYPE: DNA
<213> ORGANISM: Artificial Sequence
<220> FEATURE:
<223> OTHER INFORMATION: synthetic construct; primer

<400> SEQUENCE: 10
cgggccggct gagggtaccg cga                                     23

<210> SEQ ID NO 11
<211> LENGTH: 21
<212> TYPE: DNA
<213> ORGANISM: Artificial Sequence
<220> FEATURE:
<223> OTHER INFORMATION: synthetic construct; primer

<400> SEQUENCE: 11
gctaatgcac tccctcaata c                                       21

<210> SEQ ID NO 12
<211> LENGTH: 24
<212> TYPE: DNA
<213> ORGANISM: Artificial Sequence
<220> FEATURE:
<223> OTHER INFORMATION: synthetic construct; primer

<400> SEQUENCE: 12
cattcctaat gcacacatga tacc                                    24

<210> SEQ ID NO 13
<211> LENGTH: 40
<212> TYPE: DNA
<213> ORGANISM: Artificial Sequence
<220> FEATURE:
<223> OTHER INFORMATION: synthetic construct; primer

<400> SEQUENCE: 13
acactaaggt ttgggtttgg gtttgggttt gggttagtgt                   40

<210> SEQ ID NO 14
<211> LENGTH: 42
<212> TYPE: DNA
<213> ORGANISM: Artificial Sequence
<220> FEATURE:
<223> OTHER INFORMATION: synthetic construct; primer

<400> SEQUENCE: 14
tgttaggtat ccctatccct atccctatcc ctatccctaa ca                42